US007012162B2

(12) United States Patent
Mackewitz et al.

(10) Patent No.: US 7,012,162 B2
(45) Date of Patent: Mar. 14, 2006

(54) PHOSPHACYCLOHEXANES AND THE USE THEREOF IN THE HYDROFORMYLATION OF OLEFINS

(75) Inventors: Thomas Mackewitz, Mannheim (DE); Wolfgang Ahlers, Worms (DE); Edgar Zeller, Mannheim (DE); Michael Röper, Wachenheim (DE); Rocco Paciello, Bad Dürkheim (DE); Rainer Papp, Ludwigshafen (DE); Konrad Knoll, Ludwigshafen (DE); Hartwig Voss, Frankenthal (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 238 days.

(21) Appl. No.: 10/311,584

(22) PCT Filed: Jun. 25, 2001

(86) PCT No.: PCT/EP01/07219

§ 371 (c)(1),
(2), (4) Date: Dec. 18, 2002

(87) PCT Pub. No.: WO02/00669

PCT Pub. Date: Jan. 3, 2002

(65) Prior Publication Data

US 2004/0106512 A1 Jun. 3, 2004

(30) Foreign Application Priority Data

Jun. 26, 2000 (DE) .......................... 100 31 108

(51) Int. Cl.
*C07C 45/50* (2006.01)
*C07F 9/02* (2006.01)
*B01J 31/00* (2006.01)

(52) U.S. Cl. .......................... 568/454; 568/12; 502/162
(58) Field of Classification Search ................. 568/454, 568/12; 502/162
See application file for complete search history.

(56) References Cited

U.S. PATENT DOCUMENTS

| | | | |
|---|---|---|---|
| 3,105,096 A | 9/1963 | Park et al. | 260/606.5 |
| 3,496,204 A | 2/1970 | Morris et al. | 260/439 |
| 5,128,297 A | 7/1992 | Takahashi et al. | 502/159 |
| 5,177,044 A | 1/1993 | vanDoorn et al. | 502/162 |
| 6,252,117 B1 | 6/2001 | Mackewitz et al. | 568/12 |

FOREIGN PATENT DOCUMENTS

| | | |
|---|---|---|
| WO | 00/026220 | 5/2000 |
| WO | 00/52017 | 9/2000 |

OTHER PUBLICATIONS

J. Falbe, New Syntheses with Carbon Monoxide, 1980, p. 55f.
J. Falbe, New Syntheses with Carbon Monoxide, 1980, p. 95f.
J. of Organometallic Chem. 585 (1999) 315–325, Dahlenburg et al.
XP–001027653, Tetrahedron, vol. 27, 5645 to 5648.
XP–001027625, Quin et al., Tetrahedron Ltr.vol. 28, No. 47,5783–5786, 1987.
J.Chem.Soc.Perkin Trans 1,2000,4451–4455.
XP–001027619, Macdonell et al., Am.CHem.Soc,1978, 4535–4540.
XP–001027615, Featherman et al., J.Org.Chem.vol. 39, No. 19,1974, 2899–2904.
XP–001021338, Issleib et al., 113–117.
Tet.Lts.vol., 38,No. 48,8417–8420,1997, AItken et al.
Derwent Abst. DE 19911920–A1.
Abst. DE889591.
Chem.Commun.1999,535–536, Schulz et al.,XP 002188271.
Tetrahedron Ltr. No. 9, 645–648, 1970, Gottfried et al.
Sommer, Anorg.allg. Chem.,376,37, 56–62 (1970).
J.Org.Chem.1984,49,2906–2909, Pastor et al.
J.Org.Chem.1961,26,5138, Rauhut et al.
Tet.Ltr.No. 17,1215–1218, 1971, Maerkl et al.
Angew.Chem.79,Jahrg,1967/No. 1, Maerkl et al. p 59.
J.Poly.Sci, Part A,Polymer CHem.,vol. 27,4205–4226(1989, Bergbreiter et al.
J.Am.Chem.Soc./88:5/Mar. 5, 1966 Price et al.
Pat.Abst.Japan, 61291532.
Organometallics 1999, 18, 4765–4777, vanderVeen et al.
J.Org.Chem.Welcher et al., 1962,27,1824–1827.
Moulijn, An Integrated Approach to Homogeneous . . . 199–248 Catalysis vol. 79, 1993.

*Primary Examiner*—Johann Richter
*Assistant Examiner*—Sikarl A. Witherspoon
(74) *Attorney, Agent, or Firm*—Novak Druce & Quigg

(57) ABSTRACT

The invention relates to phosphacyclohexanes of general formulae I and II, wherein the following designations, among others, apply: R can represent hydrogen, $C_{1-100}$-alkyl, $C_{7-20}$-aralkyl, $C_{7-20}$-alkaryl, and $C_{6-12}$-aryl: $R^1$ to $R^{10}$ can independently represent hydrogen, $C_{1-20}$-alkyl, $C_{7-20}$-aralkyl, $C_{7-20}$-alkaryl, and $C_{6-12}$-aryl: W, W' can independently represent single bonds or bridges comprising 1 to 20 carbon atoms, which can form part of a cyclic or aromatic group and can be interrupted by heteroatoms. Said phosphacyclohexanes are used as ligands in transition metal complexes of transition metals belonging to groups VIII to X of the periodic table.

(I)

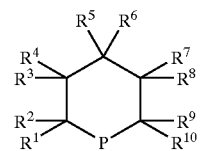

(II)

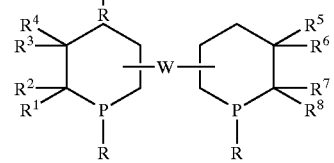

17 Claims, 3 Drawing Sheets

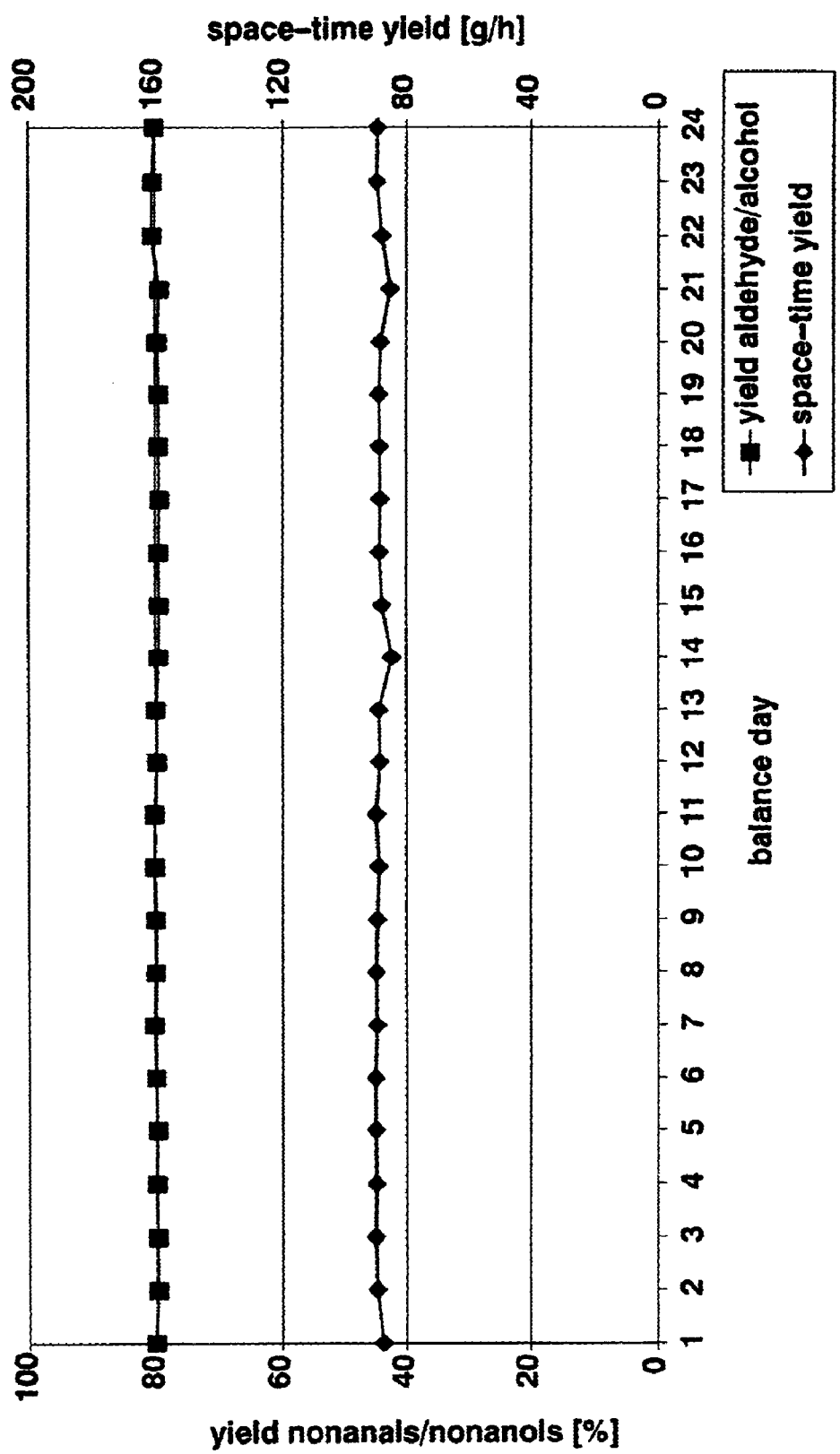

PHOSPHACYCLOHEXANES AND THE USE THEREOF IN THE HYDROFORMYLATION OF OLEFINS

The present invention relates to phosphacyclohexanes, a process for preparing them and their use in complexes of transition metals of transition group VIII of the Periodic Table in the hydroformylation of olefins.

About 7 million metric tons per annum of chemical products are produced worldwide with the aid of the hydroformylation of olefins. For this reason, there is great economic interest in carrying out the reaction with maximum activity and selectivity.

Cobalt catalysts were initially employed for industrial processes. Now, rhodium catalysts have also become established in industry. Such systems generally display higher selectivities than cobalt-containing systems.

To stabilize the rhodium-containing catalyst in the reaction and to avoid decomposition and deposition of metallic rhodium during work-up, phosphorus-containing ligands are generally used for stabilization. The latter also makes it possible to carry out the reaction with sufficient activity even at a reduced synthesis gas pressure.

For lower α-olefins, the use of, in particular, triphenylphosphine and other triarylphosphines as cocatalysts in a homogeneous phase or in a two-phase system has been found to be useful. The reactions are usually carried out, even when using monodentate ligands, so that a maximum proportion of n-aldehydes results. Although lower α-olefins can be hydroformylated very readily using triarylphosphine-modified rhodium catalysts (J. Falbe, New Syntheses With Carbon Monoxide, Springer, Berlin, 1980, p. 55 ff), this catalyst system is relatively unsuitable for internal and internal branched olefins and for higher α-olefins (J. Falbe, New Syntheses With Carbon Monoxide, Springer, Berlin, 1980, p. 95 ff). Thus, internal and internal branched double bonds are hydroformylated only very slowly in the presence of such a catalyst. Furthermore, ligand is also lost in the work-up of the reaction mixture from the hydroformylation of higher olefins by distillation, and this would have to be continually replaced. It is also generally known that triarylphosphines can be degraded in the presence of rhodium and olefin, which leads to increasing deactivation of the catalyst. The deactivation of the catalyst is particularly pronounced in the case of triarylphosphines having electron-donating substituents. The degradation of triarylphosphine ligands is generally initiated by insertion of rhodium metal into the aryl-p bond. Subsequent reactions under hydroformylation conditions then lead to the formation of inactive phosphido-bridged dimeric complexes or to alkyl-diarylphosphines and derivatives of phosphinous acid, which act as catalyst poisons and likewise lead to deactivation.

Phosphite-modified rhodium catalysts have recently been proposed for the hydroformylation of low-boiling olefins, cf. M. Beller, B. Cornils, C. D. Frohning, C. W. Kohlpaintner, J. Mol. Catal. 1995, 104, 17. Both α-olefins and short-chain internal olefins such as 2-butene or methyl 3-pentenoate can be hydroformylated very well using rhodium-containing catalysts modified with chelating phosphite. Particularly high linearities are achieved using chelating ligands having an angle of bite of about 120°. However, this catalyst system is relatively unsuitable for long-chain internal olefins having more than 7 carbon atoms and internal branched olefins. For these olefins, monodentate, sterically hindered monophosphites have experimentally been found to be useful. However, phosphites generally have the disadvantages of hydrolysis sensitivity and the tendency to undergo degradation reactions (in particular at elevated temperatures), which hinders their industrial use.

In contrast to triarylphosphines and phosphites, the far more basic trialkylphosphines have the advantage of not undergoing the abovementioned degradation reactions. Insertion reactions into the alkyl-p bond cannot occur here. In combination with CO as ligands, trialkylphosphines result in very stable complexes, which is attributable to the combination of donor and acceptor ligands, which suppresses ligand dissociation (J. A. Moulijn, P. W. N. M. Leeuwen, R. A. van Santen, Catalysis—An integrated Approach to Homogeneous, Heterogenous and Industrial Catalysis, Elsevier, Amsterdam, 1993, Chapter 6). In the case of bulky phosphines, it is assumed that the active complex bears not two, as in the case of triphenylphosphine, but only one phosphine ligand. However, the catalysts have a lower activity than triarylphosphines and this has to be increased by means of pressure and, in particular, temperature. Rhodium catalysts comprising bulky trialkylphosphines such as tricyclohexylphosphine are also able to hydroformylate internal olefins at relatively high temperatures in the intermediate-pressure range, but are relatively unsuitable for the hydroformylation of internal branched olefins because of their low activity.

The advantage of trialkylphosphines as cocatalysts in hydroformylation is their tremendous thermal stability. However, a disadvantage is the low activity of the resulting catalyst systems which can be compensated only unsatisfactorily by increasing the synthesis gas pressure and the temperature.

WO-A-97/46507 describes a process for hydroformylation in the presence of at least one transition metal catalyst, where phosphorus compounds in which the phosphorus atom has a free electron pair and three bonds to two adjacent atoms are used as ligands. These are specifically substituted phosphabenzenes.

DE-A-19743197 describes a process for preparing phosphabenzene compounds by reacting corresponding pyrylium salts with $PH_3$.

In Chem. Ber. 1961, 94, 113–117, K. Issleib and Siefried Häusler describe cyclic phosphines such as 1-substituted phosphacyclohexanes.

In J. Org. Chem. 1962, 27, 1824–1827, R. P. Welcher and N. E. Day describe 2,6-substituted 1-phosphacyclohexan-4-ones.

In Tetrahedron Letters 1970, No. 9, pp. 645–648, G. Märkl et al. describe, inter alia, 1-substituted 2,6-diphenyl-1-phosphacyclohexan-4-ones.

U.S. Pat. No. 3,105,096 describes phosphacyclohexan-4-ols and a process for preparing them from the corresponding phosphacyclohexan-4-ones.

In Z. anorg. allg. Chem. 376, 37, pp. 56–62 (1970), K. Sommer describes the cleavage of tertiary phosphines and specifically the preparation of 1-phenylphosphacyclohexane by reduction of 1-phenylphosphacyclohexan-4-one and also the preparation of unsubstituted phosphacyclohexane.

In J. Org. Chem. 1984, 49, 2906–2909, S. D. Pastor et al. describe the synthesis of 2,2,6,6-tetramethylphosphacyclohexan-4-ol.

In J. Org. Chem. 1961, 26, 5138, M. M. Rauhut et al. describe the free-radical addition of primary or secondary phosphines onto olefins.

In Tetrahedron Letters, 1971, No. 17, pp. 1215–1218, G. Märkl and A. Merz describe the reaction of 2,4,6-triaryl-substituted phosphabenzenes with organolithium and Grignard compounds.

Hydrogenation of the phosphacyclohexadienes formed as intermediates is not described.

In Angew. Chem., 79, 1967, p. 59, G. Märkl et al. describe the reaction of 2,4,6-triphenylphosphabenzene with lithium alkyls and lithium aryls.

In Tetrahedron Letters 1977, No. 5, pp. 407–410, A. J. Ashe and T. W. Smith describe the reaction of phosphabenzene with methyllithium.

It is known that catalytically active compounds can be bound to polymeric supports in order to avoid catalyst losses in the work-up. WO-A-00/53305 describes polymer-enlarged catalysts which comprise a homopolymer or copolymer of butadiene or isoprene.

In J. Polym. Sci., Part A, Polym. Chem. 1989, 27, pp. 4205–4226, D. E. Bergbreiter et al. describe the anionic polymerization of ethene in the presence of alkyllithium reagents and their subsequent reaction with phosphorus electrophiles.

The reaction of pyrylium salts with primary phosphines is known. Thus, in J. Am. Chem. Soc. 1966, 88, pp. 1034–1037, C. C. Price et al. describe the reaction of 2,4,6-triphenylpyrylium salts with phenylphosphine.

None of the abovementioned documents describes the use of phosphacyclohexanes as ligands in the hydroformylation of catalysts.

WO 00/52017 describes a process for preparing 9-hydrocarbyl-9-phosphabicyclo[3.3.1]nonanes which are suitable as ligands for the cobalt-catalyzed hydroformylation of olefins.

There is a need for catalyst systems which make effective hydroformylation possible even at intermediate and low pressures so as to avoid the expensive apparatus and high operating costs of high-pressure processes.

It is an object of the present invention to develop alkyl-substituted phosphines which are suitable as cocatalysts in the hydroformylation of olefins and have a high stability and preferably a significantly higher activity than systems known hitherto. This gives various advantages: compared to previously known systems, a smaller reaction volume is sufficient for the same amount of product because of the higher space-time yield, which results in lower capital costs. Furthermore, the higher activity enables shorter residence times to be employed, which results in a reduction in the formation of high boilers. The hydrogenation rate should be very low.

We have found that this object is achieved by the use of compounds having at least one unbridged phosphacyclohexane and/or phosphacyclohexene structural element as ligands in complexes of transition metals of transition group VIII of the Periodic Table of the Elements. These complexes are advantageous as catalysts for the hydroformylation of olefins by reaction with CO and $H_2$.

Such "unbridged" structural elements do not include ring systems in which two nonadjacent carbon atoms of the phosphacyclohexane or phosphacyclohexene ring are components of at least two different rings.

Preference is given to the use of phosphacyclohexanes of the formulae I and II

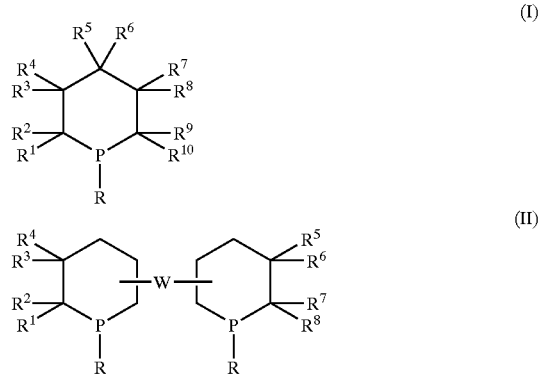

where
R is hydrogen, $C_{1-100}$-alkyl, cycloalkyl, heterocycloalkyl, $C_{7-20}$-aralkyl, $C_{7-20}$-alkaryl, $C_{6-12}$-aryl, hetaryl, W'COO$^-$M$^+$, W'SO$_3^-$M$^+$, W'PO$_3^{2-}$M$^+_2$, W'NR'$_3^+$X$^-$, W'OR', W'NR'$_2$, W'COOR', W'SR', W'(CHR'CH$_2$O)$_x$R', W'(CH$_2$NR')$_x$R', W'(CH$_2$CH$_2$NR')$_x$R', W'((CH$_2$)$_4$O)$_x$R' or W'COR', where the radicals R in the formula II may also, in place of or in addition to the group W, together form a bridge having from 1 to 20 carbon atoms which may be part of a cyclic or aromatic group and may be interrupted by heteroatoms, where the radicals R in the formula II may also, in place of or in addition to the group W, together be a polyoxyalkylene or polyalkylenimine bridge having at least 21 carbon atoms, $R^1$ to $R^{10}$ are each, independently of one another, hydrogen, $C_{1-20}$-alkyl, $C_{7-20}$-aralkyl, $C_{7-20}$-alkaryl, $C_{6-12}$-aryl, where one or more carbon atoms may be replaced by heteroatoms, W'COO$^-$M$^+$, W'SO$_3^-$M$^+$, W'PO$_3^{2-}$M$^+_2$, W'NR'$_3^+$X$^-$, W'OR', W'NR'$_2$, W'COOR', W'SR', W'(CHR'CH$_2$O)$_x$R', W'(CH$_2$NR')$_x$R', W'(CH$_2$CH$_2$NR')$_x$R', W'((CH$_2$)$_4$O)$_x$R', W'halogen, W'NO$_2$, W'COR' or W'CN, where one or more hydrogen atoms in the radicals R and $R^1$ to $R^{10}$ may be replaced by fluorine, W and W' are, independently of one another, single bonds or bridges having from 1 to 20 carbon atoms which may be part of a cyclic or aromatic group and may be interrupted by heteroatoms, where W may also be a polyoxyalkylene or polyalkylenimine bridge having at least 21 carbon atoms, R' is hydrogen, $C_{1-20}$-alkyl, carbonylalkyl, cycloalkyl or aryl, M+ is a cation equivalent, X$^-$ is an anion equivalent, x is from 1 to 240, where two geminal radicals $R^1$ to $R^{10}$ may form an oxo group and one or more of the radicals R and $R^1$ to $R^{10}$ may bear an additional trivalent phosphorus or nitrogen group capable of coordination, where in each case two vicinal radicals may be joined to form fused aliphatic or aromatic rings, where two vicinal radicals $R^1$ to $R^{10}$ may also be a chemical bond, where two or more bridges W may be present in the compounds of the formula II and the atoms of the phosphacyclohexane rings which are not bound to the bridge(s) W may also bear substituents defined as for $R^1$ to $R^{10}$, where one of the radicals R or $R^1$ to $R^{10}$ in the compounds of the formula I and one of the radicals R or $R^1$ to $R^8$ or both radicals R together or a group W in the compounds of the formula II may also be a polymer radical having a number average molecular weight in the range from 500 to 50 000 and made up of repeating units derived from monomers selected from among monoolefins and diolefins, vinylaromatics, esters of α,β-ethylenically unsaturated monocarboxylic and dicarboxylic acids with $C_1$–$C_{30}$-alkanols, N-vinyl amides, N-vinyl lactams, heterocyclic compounds which can be polymerized with ring opening and mixtures thereof, as ligands in complexes of transition metals of transition group VIII of the Periodic Table of the Elements.

For the purposes of the present invention, the expression 'alkyl' encompasses straight-chain and branched alkyl groups. They are preferably straight-chain or branched $C_1$–$C_{100}$-alkyl groups, more preferably $C_1$–$C_{20}$-alkyl groups and particularly preferably $C_1$–$C_{10}$-alkyl groups and very particularly preferably $C_1$–$C_4$-alkyl groups. Examples of alkyl groups are, in particular, methyl, ethyl, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, octyl, nonyl, decyl.

Substituted alkyl radicals preferably have 1, 2, 3, 4 or 5, in particular 1, 2 or 3, substituents. These are selected, for example, from among cycloalkyl, aryl, hetaryl, halogen, $NE^1E^2$, $(NE^1E^2E^3)^+$, carboxyl, carboxylate, —$SO_3H$ and sulfonate.

A cycloalkyl group is preferably a $C_5$–$C_7$-cycloalkyl group such as cyclopentyl, cyclohexyl or cycloheptyl.

A heterocycloalkyl group is preferably a $C_{5-7}$-heterocycloalkyl group. The heterocycloalkyl group preferably has 1, 2, 3 or 4 substituted or unsubstituted heteroatoms. Examples of heterocycles are pyrrolidine, tetrahydrofuran, pyrazolidine, imidazolidine, piperidine, piperazine and morpholine.

If the cycloalkyl group or heterocycloalkyl group is substituted, it preferably has 1, 2, 3, 4 or 5, in particular 1, 2 or 3, substituents selected from among alkyl, alkoxy and halogen.

Aryl is preferably phenyl, tolyl, xylyl, mesityl, naphthyl, anthracenyl, phenanthrenyl, naphthacenyl and in particular phenyl, naphthyl or xylyl.

Substituted aryl radicals preferably have 1, 2, 3, 4 or 5, in particular 1, 2 or 3, substituents selected from among alkyl, alkoxy, carboxyl, carboxylate, trifluoromethyl, —$SO_3H$, sulfonate, $NE^1E^2$, alkylene-$NE^1E^2$, nitro, cyano and halogen.

Hetaryl is preferably pyrrolyl, pyrazolyl, imidazolyl, indolyl, carbazolyl, pyridyl, quinolinyl, acridinyl, pyridazinyl, pyrimidinyl or pyrazinyl.

Substituted hetaryl radicals preferably have 1, 2 or 3 substituents selected from among alkyl, alkoxy, carboxyl, carboxylate, —$SO_3H$, sulfonate, $NE^1E^2$, alkylene-$NE^1E^2$, trifluoromethyl and halogen.

What has been said above regarding alkyl, cycloalkyl and aryl radicals applies analogously to alkoxy, cycloalkyloxy and aryloxy radicals.

$E^1$, $E^2$ and $E^3$ are preferably selected independently from among hydrogen, alkyl and cycloalkyl. The radicals $NE^1E^2$ are preferably N,N-dimethylamino, N,N-diethylamino, N,N-dipropylamino, N,N-diisopropylamino, N,N-di-n-butylamino, N,N-di-tert-butylamino, N,N-dicyclohexylamino or N,N-diphenylamino.

A heteroatom is preferably an oxygen atom, a sulfur atom, a disubstituted silicon atom or a monosubstituted nitrogen atom, here the substituents are each, independently of one another, hydrogen, alkyl, cycloalkyl, heterocycloalkyl, aryl, hetaryl, alkoxy, cycloalkoxy or aryloxy.

Halogen is fluorine, chlorine, bromine or iodine, preferably fluorine, chlorine or bromine.

For the purposes of the present invention, carboxylate and sulfonate are preferably each a derivative of a carboxylic acid function or of a sulfonic acid function, in particular a metal carboxylate or sulfonate, a carboxylic ester or sulfonic ester function or a carboxamide or sulfonamide function. They include, for example, esters of $C_1$–$C_4$-alkanols such as methanol, ethanol, n-propanol, isopropanol, n-butanol, sec-butanol and tert-butanol.

For the purposes of the present invention, polybutadienes always include their partial or full hydrogenation products.

Polyoxyalkylene is preferably a compound comprising repeating units selected from among $+\!(CH_2CH_2O)\!\!\frac{}{x_1}$, $+\!(CH(CH_3)CH_2O)\!\!\frac{}{x_2}$ and $+\!((CH_2)_4O)\!\!\frac{}{x_3}$, where $x_1$, $x_2$ and $x_3$ are each, independently of one another, an integer from 0 to 240, preferably from 0 to 100. The sum of $x_1$, $x_2$ and $x_3$ is an integer from 1 to 240, preferably from 2 to 100. In polyoxyalkylenes comprising two or three different repeating units, the order is immaterial, i.e. the repeating units can be randomly distributed, alternate or be arranged in blocks. What has been said above with regard to the polyoxyalkylenes applies analogously to polyalkylenimines in which the oxygen atom is in each case replaced by a group $NR^i$, where $R^i$ is hydrogen or $C_{1-4}$-alkyl.

$M^+$ is a cation equivalent, i.e. a monovalent cation or the part of a polyvalent cation corresponding to a single positive charge. $M^+$ is preferably an alkali metal cation, e.g. $Li^+$, $Na^+$ or $K^+$, or an alkaline earth metal cation, $NH_4^+$ or a quaternary ammonium compound as is obtainable by protonation or quaternization of amines. Preference is given to alkali metal cations, in particular sodium or potassium ions.

$X^-$ is an anion equivalent, i.e. a monovalent anion or the part of a polyvalent anion corresponding to a single negative charge. $X^-$ is preferably a carbonate, carboxylate or halide, particularly preferably $Cl^-$ or $Br^-$.

x is an integer from 1 to 240, preferably an integer from 1 to 100, in particular from 1 to 50, especially from 3 to 40.

If the radical R is a substituted $C_{1-100}$-alkyl radical, it can, for example, be monosubstituted or polysubstituted by radicals as indicated for $R^1$ to $R^{10}$.

In the radicals R, one or more of the carbon atoms present in the radical can be replaced by heteroatoms.

The radical R is preferably selected from among phenyl and $C_{1-12}$-alkyl radicals, where the alkyl radicals may be linear, branched or cyclic and may also have oxygen atoms present as heteroatoms in the chain, e.g. in the form of alkylene oxide units, in particular ethylene oxide units, which may be terminally alkylated.

The radical R is preferably a $C_{2-14}$-alkyl radical, in particular propyl, n-butyl, sec-butyl, tert-butyl, pentyl, hexyl, heptyl, octyl, 2-ethylhexyl or dodecyl.

A $C_{5-8}$-cycloalkyl radical, in particular cyclohexyl, is also preferred as radical R.

Preference is also given to the radical R being a polyoxyalkylene or polyalkylenimine radical. Suitable polyoxyalkylenes are derived, for example, from formaldehyde (polyoxymethylenes), cyclic ethers such as tetrahydrofuran, alkylene oxides having from 2 to 4 carbon atoms in the alkyl radical and combinations thereof. Suitable alkylene oxides are, for example, ethylene oxide, 1,2-propylene oxide, epichlorohydrin, 1,2- and 2,3-butylene oxide. Suitable polyalkylenimines are derived, for example, from aziridines (alkylenimines) of the formula

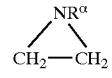

where $R^\alpha$ is hydrogen or alkyl. The number average molecular weight of the polyoxyalkylene or polyalkylenimine radicals is preferably in a range from about 400 to 50 000, particularly preferably from 800 to 20 000, especially from 2 000 to 10 000.

If a substituent bears a plurality of radicals R, these can be identical or different.

The structures of the formulae I and II can represent phosphacyclohexanones if two geminal radicals selected from among $R^1$ to $R^{10}$ together form =O. In this case, preference is given to $R^5$ and $R^6$ in formula I being an oxygen atom bound via a double bond.

In the phosphacyclohexanes of the formulae I and II, it is preferred that at least two or three or four of the radicals $R^1$ to $R^{10}$ are different from hydrogen. Preference is given to at least one, two or three of the radicals R and $R^1$ to $R^{10}$ comprising cyclic structures which may be aliphatic, aromatic or heterocyclic. In the compounds of the formula I, the cyclic structures are, for example, present in the positions 2, 4 and 6. The structures can also, for example, be present in the positions 1, 2 and 6.

The radicals $R^1$ to $R^{10}$ are preferably hydrogen and radicals as defined for R, in particular $C_{1-12}$-alkyl radicals, $C_{7-13}$-aralkyl radicals, $C_{7-13}$-alkaryl radicals and/or $C_{6-12}$-aryl radicals. The alkyl radicals can contain cyclic structures. The aryl groups of the aralkyl radicals, alkaryl radicals and aryl radicals are preferably derived from benzene or naphthalene. Examples of possible radicals are phenyl radicals ($R^1$ to $R^{10}$) and naphthyl radicals. Alkaryl radicals preferably bear one, two or three alkyl substituents, in particular methyl or ethyl radicals.

If R and/or $R^1$ to $R^{10}$ are alkyl and aryl radicals, these may be fluorinated or perfluorinated. A preferred fluorinated alkyl radical is trifluoromethyl.

In a useful embodiment of the invention, at least one of the radicals R or $R^1$ to $R^{10}$ in the compounds of the formula I or II is a polar (hydrophilic) group, which then generally results in water-soluble catalysts. The polar groups are preferably selected from among W'COO$^-$M$^+$, W'SO$_3^-$M$^+$, W'PO$_3^{2-}$M$^+_2$, W'NR'$_3^+$X$^-$, W'OR', W'NR'$_2$, W'COOR', W'SR', W'(CHR'CH$_2$O)$_x$R', W'(CH$_2$NR')$_x$R', W'(CH$_2$CH$_2$NR')$_x$R' or W'((CH$_2$)$_4$O)$_x$R', where W', M$^+$, X$^-$, x and R' are as defined above.

At least one of the substituents R and $R^1$ to $R^{10}$ may bear an additional trivalent phosphorus or nitrogen group capable of coordination, thus forming a bidentate or polydentate ligand. Particular preference is given to phosphine, phosphinite, phosphonite and phosphite groups and also $\eta^5$-phospholyl complexes or phosphabenzene groups.

The radicals $R^1$ to $R^{10}$ are preferably hydrocarbon radicals which contain no further heteroatoms.

The bridges W and W' are, in a preferred embodiment, single bonds or bridges having from 1 to 6 carbon atoms which may be part of a cyclic or aromatic group. They can be either single bonds or lower alkylene groups such as $C_{1-10}$-alkylene.

In the compounds of the formula II, the two radicals R together and/or a group W can be a bridge having from 1 to 20 carbon atoms which may be part of a cyclic or aromatic group and/or may be interrupted by heteroatoms. In a first preferred embodiment, the bridging groups are each a $C_{1-20}$-alkylene chain. Bridging alkylene chains may be substituted by cycloalkyl, heterocycloalkyl, aryl and/or hetaryl, which may bear 1, 2 or 3 of the above-mentioned substituents. Bridging alkylene chains can, depending on the number of carbon atoms in the alkylene chain, have 1, 2, 3 or 4 double bonds and/or be interrupted by from 1 to 10, e.g. 1, 2 or 3, nonadjacent substituted or unsubstituted heteroatoms and/or may be fused with one, two or three cycloalkyl, aryl or hetaryl rings. The alkylene chains preferably have from 1 to 15, particularly preferably from 1 to 10, for example 6 or 3, carbon atoms in the chain.

If the two radicals R together and/or a group W in the compounds of the formula II is/are an aryl-fused alkylene bridge, the fused-on arylene is preferably benzene or naphthalene.

Fused-on benzene rings are preferably unsubstituted or bear one, two or three, in particular one or two, substituents selected from among alkyl, alkoxy, halogen, SO$_3$H, sulfonate, NE$^1$E$^2$, alkylene-NE$^1$E$^2$, trifluoromethyl, nitro, carboxyl, alkoxycarbonyl, acyl and cyano. Fused-on naphthalenes are preferably unsubstituted or have one, two or three, in particular one or two, of the substituents mentioned above in the case of the fused-on benzene rings in the ring which is not fused on and/or in the fused-on ring.

The bridging groups are preferably unsubstituted $C_{2-6}$-alkylene bridges.

Preference is also given to the two radicals R together and/or a group W being a $C_{2-20}$-alkylene bridge which is interrupted by up to 20, in particular up to 10, nonadjacent substituted or unsubstituted heteroatoms. These are preferably selected from among O, S, NR$^\alpha$ and SiR$^\beta$R$^\gamma$, where the radicals R$^\alpha$, R$^\beta$ or R$^\gamma$ are, independently of one another, alkyl, cycloalkyl or aryl. The bridges are preferably oligomeric polyoxyalkylene or polyalkylenimine bridges. These comprise, for example, the above-described repeating units.

In a further embodiment, the two radicals R together and/or a group W in the compounds of the formula II may also form a relatively high molecular weight polyoxyalkylene or polyalkylenimine bridge having at least 21 carbon atoms. The number average molecular weight of the polyoxyalkylene or polyalkylenimine radicals is preferably in a range from about 400 to 50 000, particularly preferably from 800 to 20 000 and especially from 1 000 to 10 000. The bridges are particularly preferably polyethylene oxides, copolymers of ethylene oxide and 1,2-propylene oxide in which the alkylene oxides can be incorporated in any order, alternately or in the form of blocks, and also polyethyleneimines.

In a useful embodiment, it is also possible for one of the radicals R or $R^1$ to $R^{10}$ in the compounds of the formula I and one of the radicals R or $R^1$ to $R^8$ or the two radicals R together or a group W in the compounds of the formula II to be a polymer radical which has a number average molecular weight in the range from about 500 to 50 000 and is different from the above-mentioned definitions for these radicals and groups. The repeating units of these polymer radicals are formally derived from monomers selected from among monoolefins and diolefins, vinylaromatics, esters of α,β-ethylenically unsaturated monocarboxylic and dicarboxylic acids with $C_{1-30}$-alkanols, N-vinyl amides, N-vinyl lactams, heterocyclic compounds which can be polymerized with ring opening and mixtures thereof.

The polymer radicals preferably have a number average molecular weight in the range from 800 to 20 000, particularly preferably from 2 000 to 10 000.

Monoolefins preferred as monomers are $C_{2-8}$-monoolefins such as ethene, propene, n-butene, isobutene and aromatic-substituted monoolefins such as 1,1-diphenylethylene, 1,2-diphenylethylene and mixtures of the abovementioned monoolefins. Diolefins preferred as monomers are conjugated dienes such as butadiene, isoprene, 2,3-dimethylbutadiene, piperylene (1,3-pentadiene) and mixtures thereof. The esters of α,β-ethylenically unsaturated monocarboxylic and dicarboxylic acids are preferably selected from among the esters of acrylic acid, methacrylic acid, maleic acid, fumaric acid, itaconic acid and crotonic acid. Preference is given to the esters with $C_{1-20}$-alkanols. These include, for example, methyl (meth)acrylate, ethyl (meth)acrylate, n-butyl (meth)acrylate, tert-butyl (meth)acrylate, n-hexyl (meth)acrylate, n-octyl (meth)acrylate, ethylhexyl (meth)acrylate, etc. Vinylaromatics suitable as monomers are, for example, styrene, α-methylstyrene, o-chlorostyrene, vinyltoluenes and mixtures thereof. Suitable N-vinyl amides are, for example, N-vinylformamide, N-vinylacetamide, N-vinylpropionamide and mixtures thereof. Suitable N-vinyl lactams are, for example, N-vinylpyrrolidine, N-vinylpiperidone, N-vinylcaprolactam and mixtures thereof. Monomers suitable for ring-opening polymerization are, for example, cyclic ethers such as ethylene oxide and propylene oxide, cyclic amines, cyclic sulfides (ethylene sulfide, thietanes), lactones and lactams. Preference is given to ε-caprolactone and ε-caprolactam.

The abovementioned monomers can be used individually, in the form of mixtures from the one class of monomers or generally as mixtures.

The preparation of the polymers suitable as radicals is carried out by customary polymerization processes known to those skilled in the art. Depending on the monomers to be polymerized, these include free-radical, cationic and anionic polymerization, including cationic and anionic ring-opening polymerization.

If the polymer radicals are prepared by anionic polymerization, for example by means of the appropriate reaction variant described below for preparing the phosphacyclohexanes used according to the present invention, preference is given to using acceptor-activated ethylenically unsaturated compounds and ethene as monomers.

If one of the radicals R or $R^1$ to $R^{10}$ in the compounds of the formula I and one of the radicals R or $R^1$ to $R^8$ or the two radicals R together or a group W in the compounds of the formula II is/are a polymer radical, this is preferably a polyolefin radical (polyalkene) radical. These polyolefins comprise repeating units derived from polymerized monomers which are preferably selected from among $C_{2-6}$-alkenes such as ethene, propene, n-butene, isobutene, olefins having two double bonds such as butadiene, isoprene, 1,3-pentadiene and mixtures thereof. Polyolefins into which conjugated dienes are incorporated can comprise essentially exclusively the 1,2- and 1,4-polymerization products or else mixed forms having any proportions of 1,2- and 1,4-units. Methods of setting the proportions of 1,2- and 1,4-units in the polymerization of conjugated dienes are known to those skilled in the art. These include, for example, the addition of donor solvents, e.g. ethers such as THF or amines, in anionic polymerization. Polyolefins comprising repeating units of 1,2-addition products of conjugated dienes have lateral ethylenically unsaturated groups. Polyolefins comprising repeating units of 1,4-addition products have ethylenically unsaturated groups in the main chain. These can, if desired, be partly or fully hydrogenated. However, the use of phosphacyclohexanes bearing polyolefin radicals having ethylenically unsaturated side chains as ligands in transition metal complexes for hydroformylation is also possible. In this case, at least partial conversion of the ethylenically unsaturated side chains into alcohol groups generally occurs under hydroformylation conditions, i.e. ligands having polar side chains result.

If one of the radicals R or $R^1$ to $R^{10}$ in the compounds of the formula I and one of the radicals R or $R^1$ to $R^8$ or the two radicals R together or a group W in the compounds of the formula II is/are a polyolefin radical, this is preferably a polyethylene or polybutadiene radical.

In addition, the positions of the phosphacyclohexane rings which are not bound to the bridge W in structure II may be one of the radicals R or $R^1$ to $R^{10}$.

The radical R' is preferably hydrogen or a $C_{1-6}$-alkyl radical such as a methyl or ethyl radical. If a substituent bears a plurality of radicals R', these can be identical or different.

It is preferred that at most one substituent different from hydrogen is present on each ring carbon of the phosphacyclohexane, apart from C=O in the 4 position and $C(CH_3)_2$ in the 2 and/or 6 position. For example, substituents can be present in the 2 and 6 positions, the 2, 4 and 6 positions or the 2, 3, 5 and 6 positions. Particular preference is given to substituents, especially aryl, in the 2 and 6 positions.

Preference is given to using, as ligands, phosphacyclohexanes selected from among compounds of the formula III

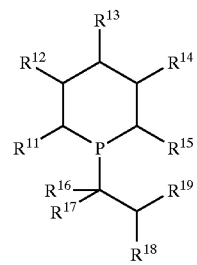

(III)

where:

$R^{11}$ to $R^{19}$ are each, independently of one another, hydrogen, $C_{1-20}$-alkyl, $C_{7-20}$-aralkyl, $C_{7-20}$-alkaryl, $C_{6-12}$-aryl, where one or more carbon atoms may be replaced by heteroatoms, $W'COO^-M^+$, $W'SO_3^-M^+$, $W'PO_3^{2-}M^+_2$, $W'NR'_3{}^+X^-$, $W'OR'$, $WNR'_2$, $W'COOR'$, $W'SR'$, $W'(CHR'CH_2O)_xR'$, $W'(CH_2NR')_xR'$, $W'(CH_2CH_2NR')_xR'$, where in each case two vicinal radicals $R^{11}$ to $R^{15}$ and/or $R^{17}$ and $R^{18}$ and/or $R^{16}$ and $R^{17}$ and/or $R^{16}$ and $R^{19}$ and/or $R^{18}$ and $R^{19}$ may be joined to form rings, W' is a single bond or a bridge having from 1 to 20 carbon atoms which may be part of a cyclic or aromatic group, R' is hydrogen or $C_{1-6}$-alkyl, M+ is a cation, $X^-$ is an anion, x is from 1 to 240, where one or more of the radicals $R^{11}$ to $R^{19}$ may bear an additional trivalent phosphorus or nitrogen group capable of coordination, and $R^{18}$ may also be $-W'-CR^{20}=CR^{21}R^{22}$, where $R^{20}$, $R^{21}$, $R^{22}$ are as defined above for $R^{11}$ to $R^{19}$.

Particular preference is given to using, as ligands, phosphacyclohexanes selected from among compounds of the formulae I.a to I.g and II.a

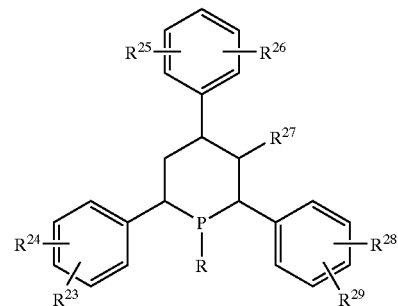

(I.a)

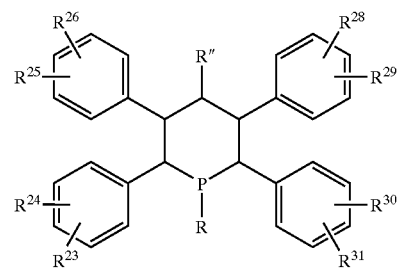

(I.b)

-continued

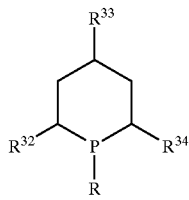
(I.c)

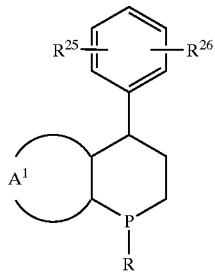
(I.d)

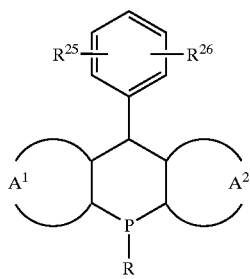
(I.e)

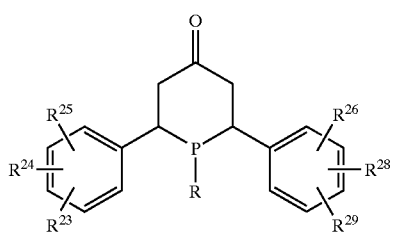
(I.f)

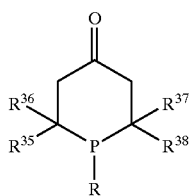
(I.g)

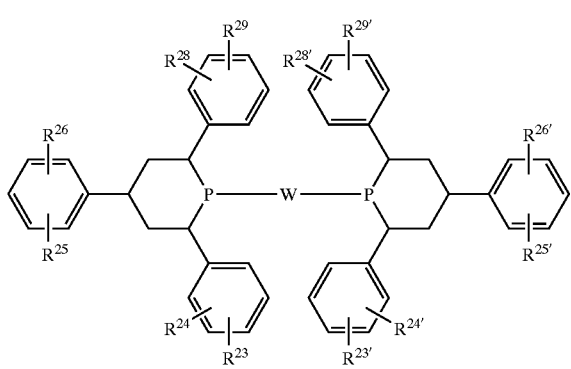
(II.a)

where
R is $C_{1-20}$-alkyl, cycloalkyl, $C_{6-12}$-aryl, W'(CHR'CH$_2$O)$_x$R', W'((CH$_2$)$_4$O)$_x$R' or a polymer radical having a number average molecular weight in the range from 500 to 50 000 and made up of ethylene and/or butadiene, where W' is a single bond or $C_{1-4}$-alkylene,
R' is hydrogen or $C_{1-20}$-alkyl,
x is an integer from 1 to 240,
$R^{23}$, $R^{23'}$, $R^{24}$, $R^{24'}$, $R^{25}$, $R^{25'}$, $R^{26}$, $R^{26'}$, $R^{28}$, $R^{28'}$, and $R^{31}$ are each, independently of one another, hydrogen, alkyl, alkoxy, carboxyl, carboxylate, trifluoromethyl, —SO$_3$H, sulfonate, NE$^1$E$^2$ or alkylene-NE$^1$E$^2$ where E$^1$ and E$^2$ are each, independently of one another, hydrogen, alkyl or cycloalkyl,
$R^{27}$ is hydrogen, alkyl, cycloalkyl, aryl or aralkyl,
$R^{32}$, $R^{33}$, $R^{34}$, $R^{35}$, $R^{36}$, $R^{37}$ and $R^{38}$ are each, independently of one another, alkyl or cycloalkyl,
R" is hydrogen or phenyl,
$A^1$ and $A^2$ together with the adjacent carbon atoms of the phosphacyclohexane to which they are bound form a fused-on ring system having in each case 1 or 2 further rings,
W is a bridge having from 1 to 20 carbon atoms which may be interrupted by heteroatoms.

In the compounds of the formulae I.a to I.f and II.a, the radicals $R^{23}$, $R^{23'}$, $R^{24}$, $R^{24'}$, $R^{25}$, $R^{25'}$, $R^{26}$, $R^{26'}$, $R^{28}$, $R^{28'}$, $R^{29}$, $R^{29'}$, $R^{30}$ and $R^{31}$ are each preferably, independently of one another, hydrogen, $C_{1-4}$-alkyl, preferably methyl, ethyl, isopropyl, tert-butyl, or $C_{1-4}$-alkoxy, preferably methoxy.

$R^{27}$ is preferably aralkyl, in particular benzyl.

$R^{32}$, $R^{33}$ and $R^{34}$ are each preferably, independently of one another, $C_{1-4}$-alkyl, particularly preferably tert-butyl.

$R^{35}$, $R^{36}$, $R^{37}$ and $R^{38}$ are each preferably, independently of one another, $C_{1-4}$-alkyl, particularly preferably methyl.

The rings of the fused-on ring systems $A^1$ and $A^2$ are preferably 5- to 7-membered rings. Preference is given to ring systems which are derived from benzene, naphthalene and their partial hydrogenation products or perhydrogenation products. Fused-on rings are preferably unsubstituted or have 1, 2 or 3, in particular 1 or 2, substituents per ring, with the substituents being selected from among alkyl, alkoxy, halogen, SO$_3$H, sulfonate, NE$^1$E$^2$, alkylene-NE$^1$E$^2$, trifluoromethyl, nitro, carboxyl, alkoxycarbonyl, acyl and cyano.

In the formula II.a, the radical W is preferably a $C_{1-10}$-alkylene group, for example a $C_2$–$C_8$-alkylene group. Preference is also given to the group W being a bridge having from 1 to 20 carbon atoms which may be interrupted by up to 10 nonadjacent oxygen atoms. The bridge is then a low molecular weight polyoxyalkylene group comprising repeating units derived from ethylene oxide, propylene oxide, tetrahydrofuran and any combinations thereof. The group W can also be a polyoxyalkylene group having more than 21 carbon atoms.

Preference is given to compounds of the formula I.a in which $R^{23}$, $R^{24}$, $R^{25}$, $R^{26}$, $R^{27}$, $R^{28}$, and $R^{29}$ are each hydrogen, Preference is also given to compounds of the formula I.a in which $R^{25}$, $R^{26}$ and $R^{27}$ are each hydrogen and $R^{23}$, $R^{24}$, $R^{28}$ and $R^{29}$ are each $C_{1-4}$-alkyl, particularly preferably methyl. Preference is also given to compounds of the formula I.a in which $R^{23}$ and $R^{28}$ are each $C_{1-4}$-alkyl, particularly preferably methyl, and $R^{24}$, $R^{25}$, $R^{26}$, $R^{27}$ and $R^{29}$ are each hydrogen. The phenyl radicals in the 2 and 6 positions of the phosphacyclohexane ring of the compounds of the formula I.a preferably each have an alkyl radical in the 2 position or two alkyl radicals in the 2 and 4 positions. The radical R in the compounds of the formula I.a (and likewise I.b to I.f and II.a) is preferably $C_{1-14}$-alkyl such as propyl, n-butyl, sec-butyl, isobutyl, n-octyl, 2-ethylhexyl, dodecyl, or cyclohexyl, methoxyethoxyethyl or a polymer radical, for example a polyethylene or polybutadiene radical.

In the compounds of the formula I.b, the radicals $R^{23}$, $R^{24}$, $R^{25}$, $R^{26}$, $R^{28}$, $R^{29}$, $R^{30}$ and $R^{31}$ are preferably selected from among hydrogen and $C_{1-4}$-alkyl, particularly preferably hydrogen.

In the compounds of the formula I.c, the radicals $R^{32}$, $R^{33}$ and $R^{34}$ are each particularly preferably tert-butyl.

The compound of the formula I.e is particularly preferably a 1,2,7,8-dibenzo-3,4,5,6-tetrahydro-9-phosphaanthracene skeleton.

In the compounds of the formula I.f, the radicals $R^{23}$, $R^{24}$, $R^{25}$, $R^{26}$, $R^{28}$ and $R^{29}$ are particularly preferably selected from among hydrogen and $C_{1-4}$-alkyl, particularly preferably methyl. The phenyl radicals of the phosphacyclohexanones of the formula I.f preferably have a substituent different from hydrogen in the 2 position, two substituents different from hydrogen in the 2 and 4 positions or three substituents different from hydrogen in the 2, 4 and 6 positions.

Particular preference is given to compounds of the formula I.g in which $R^{35}$, $R^{36}$, $R^{37}$ and $R^{38}$ are each $C_{1-4}$-alkyl, in particular methyl.

As regards preferred substituents of the compounds of the formula II.a, what has been said above for compounds of the formula I.a applies. The bridging group W is preferably a $C_{1-10}$-alkylene group, for example a $C_2$–$C_8$-alkylene group.

Examples of preferred compounds are the following phosphacyclohexanes:

1 [a-i]

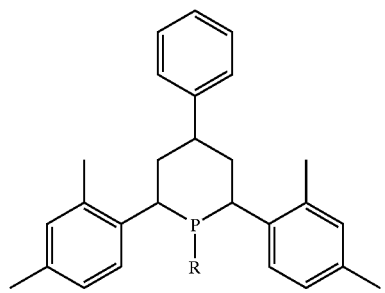

a: R = $C_2H_5$
b: R = $C_3H_7$
c: R = $C_4H_9$
d: R = $C_6H_{11}$
e: R = cyclo-$C_6H_{11}$
f: R = $C_8H_{17}$ 2 [a-i]

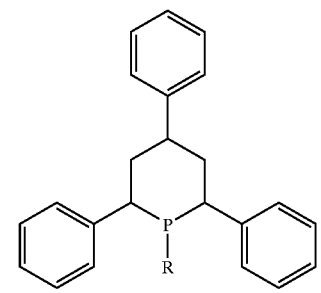

g: R = $CH_2CH_2O[CH_2CH_2O]_nCH_3$ where n = 0 to 100
h: R = polyethylene, $M_n$ = 500–50 000
i: R = polybutadiene, $M_n$ = 500–50 000
   (partially hydrogenated or fully hydrogenated)
k: R = polyisobutene, $M_n$ = 500–50 000

3 [a-i]

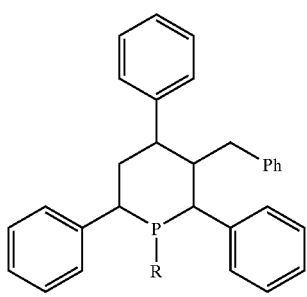

4 [a-i]

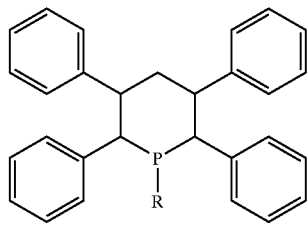

5 [a-i]

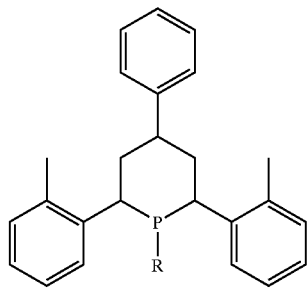

6 [a-i]

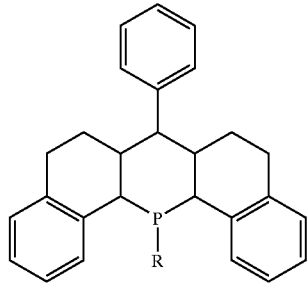

7 [a-i]

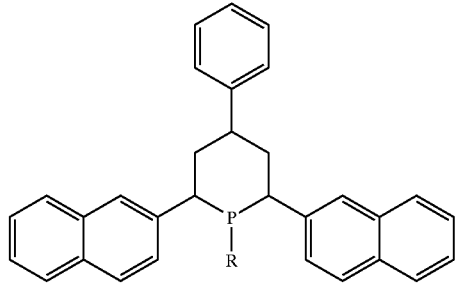

8

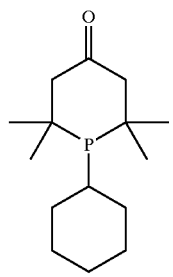

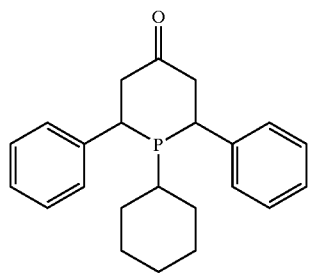
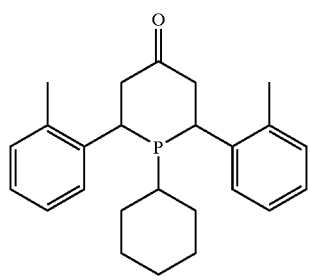
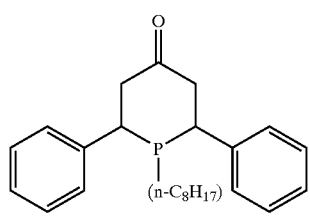
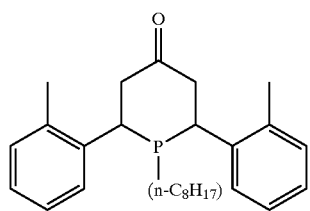
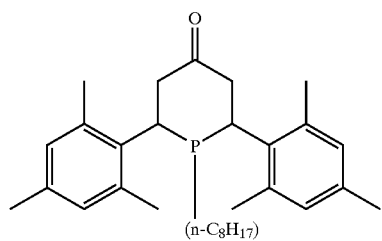
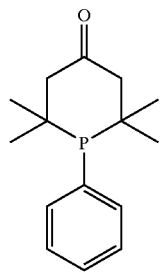
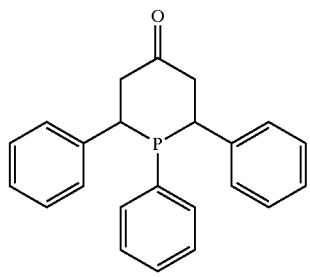
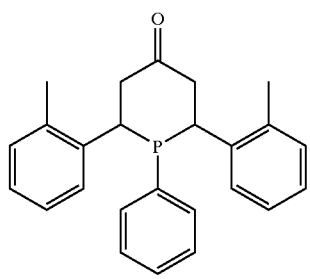
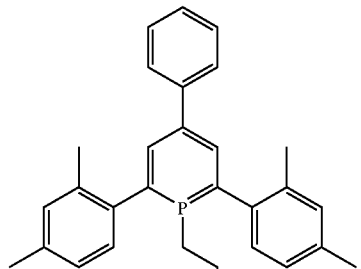
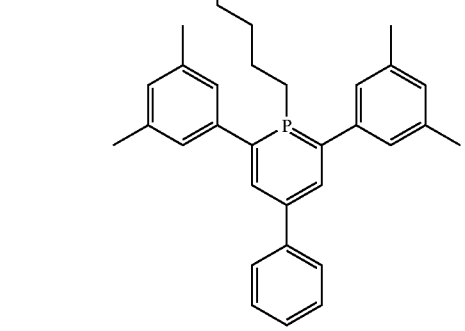

-continued

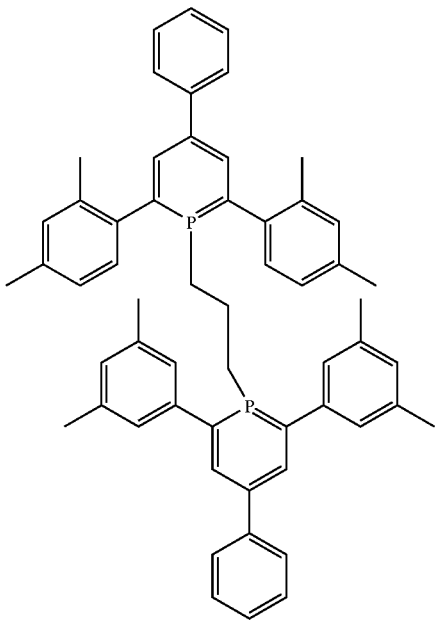

18

Particular preference is given to the structures 1.

The invention further provides phosphacyclohexanes of the formulae I, II and III as described above and mixtures thereof, with the exception of:
compounds of the formula I in which $R^1$ to $R^{10}$ are each hydrogen and R is selected from among hydrogen, ethyl, cyclohexyl and phenyl and
compounds of the formula I in which $R^5$ and $R^6$ together form an oxo group or one of the radicals $R^5$ or $R^6$ is hydroxyl and the other is hydrogen.

For useful and preferred embodiments, what has been said above with regard to the phosphacyclohexanes described for use as ligands applies.

Various previously published methods are available for preparing the phosphacyclohexanes used according to the present invention as cocatalysts. Methods which may be mentioned by way of example are the following, which are hereby fully incorporated by reference:

1-substituted phosphacyclohexanes can, according to Chem. Ber. 1961, 94, 113–117 be prepared by condensation of alkali metal phosphides of the type $Li_2RP$ with 1,5-dihaloalkanes.

According to J. Org. Chem. 1962, 27, 1824–1827, 2,6-substituted 1-phosphacyclohexan-4-ones can be prepared by condensation of phorones or phorone derivatives with secondary alkylphosphines and arylphosphines. The phosphacyclohexanones obtained can be converted into 2,6-substituted phosphacyclohexanes by a subsequent Wolff-Kishner reduction.

According to Tetrahedron Letters 1970, 645–648, 1-substituted 2,6-diphenyl-1-phosphacyclohexan-4-ones can be obtained by condensation of bis(hydroxymethyl) phosphine with dibenzylideneacetone in boiling pyridine.

Phosphacyclohexanols and a process for preparing such compounds from phosphacyclohexanones are described in U.S. Pat. No. 3,105,096.

However, the number of phosphacyclohexanes which can be prepared by the above methods is restricted to specific substitution patterns. Bulky phosphacyclohexanes, in particular, can be obtained only with difficulty, if at all, by the above methods.

A further object of the present invention is therefore to develop a synthetically simple and advantageous route to phosphacyclohexanes and phosphacyclohexenes, in particular phosphacyclohexanes of the formula III.

The invention further provides a process for preparing at least one phosphacyclohexene and/or phosphacyclohexane of the formulae V.a to V.c

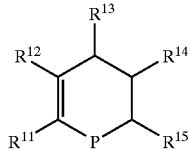
(V.a)

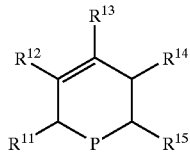
(V.b)

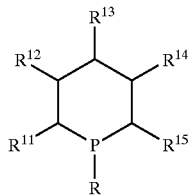
(V.c)

where
R is hydrogen, $C_{1-100}$-alkyl, cycloalkyl, heterocycloalkyl, $C_{7-20}$-aralkyl, $C_{7-20}$-alkaryl, $C_{6-12}$-aryl, hetaryl, W'COO$^-$M$^+$, W'SO$_3^-$M$^+$, W'PO$_3^{2-}$M$^+_2$, W'NR'$_3^+$X$^-$, W'OR', W'NR'$_2$, W'COOR', W'SR', W'(CHR'CH$_2$O)$_x$R', W'(CH$_2$NR')$_x$R', W'(CH$_2$CH$_2$NR')$_x$R', W'((CH$_2$)$_4$O)$_x$R' or W'COR',
where the radical R or one of the radicals $R^{11}$ to $R^{15}$ in each of two identical or different units V.a, V.b or V.c may also together form a bridging group W which covalently joins these units to one another,
$R^{11}$ to $R^{15}$ are each, independently of one another, hydrogen, $C_{1-20}$-alkyl, $C_{7-20}$-aralkyl, $C_{7-20}$-alkaryl, $C_{6-12}$-aryl, where one or more carbon atoms may be replaced by heteroatoms, W'COO$^-$M$^+$, W'SO$_3^-$M$^+$, W'PO$_3^{2-}$M$^+_2$, W'NR'$_3^+$X$^-$, W'OR', W'NR'$_2$, W'COOR', W'SR', W'(CHR'CH$_2$O)$_x$R', W'(CH$_2$NR')$_x$R', W'(CH$_2$CH$_2$NR')$_x$R', W'((CH$_2$)$_4$O)$_x$R', W'halogen, W'NO$_2$, W'COR' or W'CN,
where one or more hydrogen atoms in the radicals R and $R^{11}$ to $R^{15}$ may be replaced by fluorine,
W and W' are, independently of one another, single bonds or bridges having from 1 to 20 carbon atoms which may be part of a cyclic or aromatic group and may be interrupted by heteroatoms, where W may also be a polyoxyalkylene or polyalkylenimine bridge having at least 21 carbon atoms,
R' is hydrogen, $C_{1-20}$-alkyl, carbonylalkyl, cycloalkyl or aryl,
M+ is a cation equivalent,
X$^-$ is an anion equivalent and
x is an integer from 1 to 240,
where one or more of the radicals R and $R^{11}$ to $R^{15}$ may bear an additional trivalent phosphorus or nitrogen group capable of coordination
where one of the radicals R or $R^{11}$ to $R^{15}$ or, if present, a group W in the compounds of the formulae V.a, V.b and V.c may also be a polymer radical having a number average molecular weight in the range from 500 to 50 000 and made up of repeating units derived from monomers selected from among monoolefins and diolefins, vinylaromatics, esters of α,β-ethylenically unsaturated monocarboxylic and dicarboxylic acids with $C_{1-30}$-alkanols, N-vinyl amides, N-vinyl lactams, heterocyclic compounds which can be polymerized with ring opening and mixtures thereof,
which comprises
a) hydrogenating at least one phosphabenzene of the formula IV

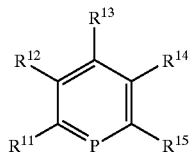

(IV)

where $R^{11}$, $R^{12}$, $R^{13}$, $R^{14}$ and $R^{15}$ are as defined above, by means of hydrogen in the presence of a hydrogenation catalyst to give at least one phosphacyclohexene and/or phosphacyclohexane of the formulae V.a to V.c in which the radical R is hydrogen, and, if desired,
b1) reacting the hydrogenation product(s) obtained in step a)
with at least one ethylenically unsaturated compound
in the presence of at least one free-radical former, or
in the presence of at least one acid or at least one base or at least one transition metal compound, or
at an elevated temperature in the range from 100 to 250° C., or
b2) reacting the hydrogenation product(s) obtained in step a) with at least one compound of the formula R—X or X-W-Y, where X and Y are nucleophilically displaceable groups and R and W are as defined above, with the exception of R=hydrogen.
Step a) Hydrogenation of the Phosphabenzene
In principle, the hydrogenation can be carried out using customary phosphabenzenes and bisphosphabenzenes whose benzene rings bear substituents corresponding to the above-described compounds of the formula I or II.
Preferred starting materials are phosphabenzene compounds of the formula IV.a

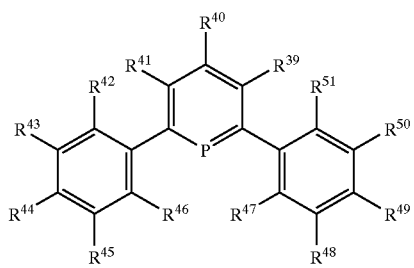

(IV.a)

where the radicals $R^{39}$ to $R^{51}$ are each, independently of one another, hydrogen, W'COOM, W'SO$_3$M, W'NR$_3$X, W'NR$_2$, W'OR, W'COOR or W'SR (where M=hydrogen, NH$_4$ or an alkali metal, X=an anion, R=hydrogen or $C_{1-6}$-alkyl), or $C_{1-12}$-alkyl, $C_{6-12}$-aryl, $C_{7-12}$-aralkyl, $C_{7-12}$-alkaryl or a $C_{3-6}$-heteroaromatic, where the alkyl, aryl, alkaryl and aralkyl radicals may be substituted by the abovementioned radicals or two or more of the radicals may be joined to form fused-on aliphatic or aromatic rings.
It is preferred that at least one of the radicals $R^{42}$ and $R^{46}$ and at least one of the radicals $R^{47}$ and $R^{51}$ are, independently of one another, $C_{1-12}$-alkyl, $C_{6-12}$-aryl, $C_{7-12}$-aralkyl or $C_{7-12}$-alkaryl, or $R^{42}$ and $R^{41}$ and/or $R^{51}$ and $R^{39}$ form a $C_{2-4}$-alkylene radical.

It is particularly preferred that at least one of the radicals $R^{42}$ and $R^{46}$ and at least one of the radicals $R^{47}$ and $R^{51}$ is $C_{1-6}$-alkyl, or ($R^{42}$ and $R^{41}$) and ($R^{51}$ and $R^{39}$) in each case form a $C_{2-3}$-alkylene radical.

$R^{40}$ is preferably a phenyl radical.

It is preferred that the radicals $R^{39}$ and $R^{41}$ are hydrogen and in each case not more than three of the radicals $R^{42}$ to $R^{46}$ and $R^{47}$ to $R^{51}$ are different from hydrogen. The radicals $R^{42}$ to $R^{46}$ and $R^{47}$ to $R^{51}$ in each case particularly preferably contain not more than 6, in particular not more than 3, carbon atoms.

In the compounds of the formula (IV.a), there are preferably from 3 to 5, in particular 3, further aromatic units present in addition to the phosphabenzene ring. The number of alkyl radicals in the compounds of the formula (IV.a) is preferably 0 in the case of purely cyclic structures, otherwise preferably from 2 to 7, in particular from 2 to 6. The alkyl radicals can be linear or branched. Preference is given to only linear alkyl radicals being present. The same applies analogously to bridging alkylene groups.

The following phosphabenzenes may be mentioned by way of example:

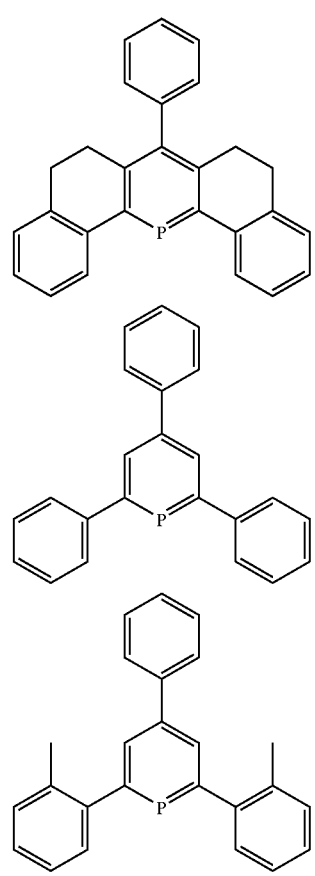

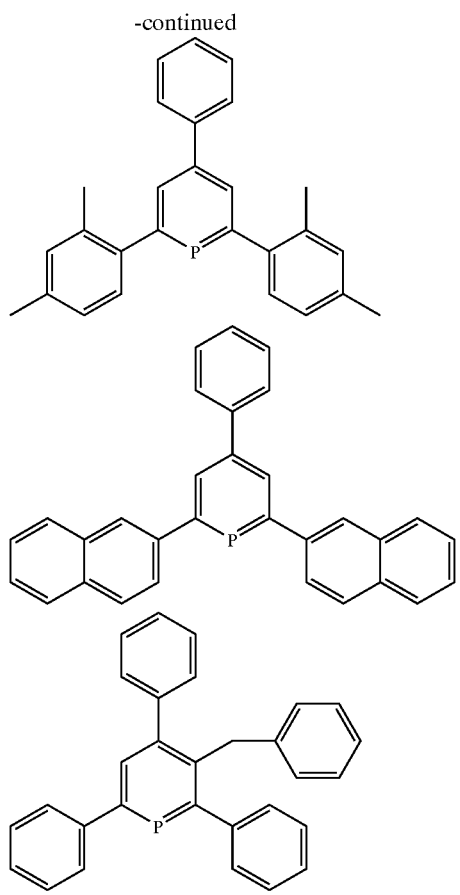

Suitable phosphabenzenes apart from the above-described compounds are, in particular, 2,4,6-triarylphosphabenzenes, 2,3,5,6-tetraarylphosphabenzenes and 2,3,4,5,6-pentaarylphosphabenzenes. Particular preference is given to 2,4,6-triarylphosphabenzenes. Phosphacyclohexanes and phosphacyclohexenes which are unsubstituted in the 1 position are generally of lower catalytic activity than corresponding compounds substituted in the 1 position.

The phosphabenzenes can be prepared by generally known methods, for example those described in G. Märkl in Multiple Bonds and Low Coordination in Phosphorus Chemistry (editors: M. Regitz, O. J. Scherer), Thieme, Stuttgart, 1990, p. 220 ff (and references cited therein). A particularly simple process for preparing phosphabenzene compounds from pyrylium salts by reaction with phosphine is described in WO 97/46507, DE-A-196 21 967 and also DE-A-197 43 197. The phosphabenzenes and bisphosphabenzenes described in these documents are hereby incorporated by reference.

Examples of suitable bisphosphabenzenes are the following compounds:

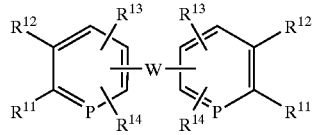

where
$R^{11}$ to $R^{14}$ and W are as defined above.

As catalysts for the hydrogenation of phosphabenzenes to phosphacyclohexanes and/or phosphacyclohexenes which are unsubstituted in the 1 position, it is generally possible to use all homogeneous or heterogeneous catalysts which are customarily employed in the hydrogenation of aromatic rings. These include catalysts based on noble metals such as Pt, Pd, Ru and Rh or transition metals such as Mo, W, Cr, Fe, Co and Ni, which can be used individually or in a mixture and/or may be applied to supports such as activated carbon, aluminum oxide, kieselguhr, etc. to increase the activity and/or stability. Examples of suitable catalysts are Raney nickel, Pd on activated carbon, metallic Pt, platinum oxide and zinc oxide, etc.

In a preferred embodiment, step a) is carried out using hydrogenation catalysts which are based on ruthenium and which enable an advantageous hydrogenation of the starting phosphabenzenes to phosphacyclohexanes and possibly phosphacyclohexenes which are unsubstituted in the 1 position (i.e. on the P atom).

In a further useful embodiment, the reaction step a) is carried out using hydrogenation catalysts which also catalyze or at least do not adversely affect a subsequent reaction which may follow in the reaction steps b1) and b2). In this case, removal of the hydrogenation catalyst after the hydrogenation may be able to be dispensed with. Particular preference is given to using a hydrogenation catalyst based on a transition metal which is capable of forming complexes or compounds which are active as hydroformylation catalysts with the resulting phosphacyclohexenes and/or cyclohexanes, if appropriate after a subsequent reaction in steps b1) or b2). These are preferably hydrogenation catalysts based on rhodium. Preference is given to rhodium carboxylates such as rhodium acetate, rhodium ethylhexanoate and dicarbonylrhodium acetylacetonate. The preparation of the hydroformylation catalyst can then advantageously be carried out in situ, i.e. the reaction mixture obtained after hydrogenation and, if applicable, a subsequent reaction can be used directly for the hydroformylation.

The temperature in the hydrogenation is preferably in a range from 20 to 250° C., particularly preferably from 50 to 180° C. and in particular from 80 to 160° C. It is generally dependent on the transition metal used. The reaction pressure is preferably in the range from ambient pressure to 600 bar, particularly preferably from 5 to 100 bar and in particular from 10 to 80 bar. A person skilled in the art can control the proportion of phosphacyclohexenes and phosphacyclohexanes in the product mixture by appropriate choice of the reaction temperatures and/or pressures.

The hydrogenation in reaction step a) can be carried out in the presence of pure hydrogen or in the presence of hydrogen-containing gas mixtures, for example synthesis gas.

The hydrogenation of phosphabenzenes in reaction step a) results in phosphacyclohexanes and/or phosphacyclohexenes selected from among the compounds of the formulae V.a to V.c (V.a)

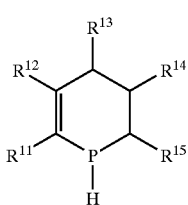

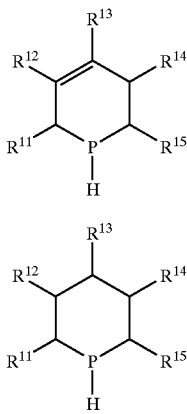

(V.b)

(V.c)

where $R^{11}$, $R^{12}$, $R^{13}$, $R^{14}$ and $R^{15}$ are as defined above, and mixtures thereof. In general, the reaction forms predominantly phosphacyclohexanes or mixtures with phosphacyclohexenes comprising predominantly, i.e. at least 80% by weight, preferably at least 90% by weight, of phosphacyclohexanes. Such mixtures can generally be used for subsequent reactions without prior work-ups.

If desired, the reaction mixture obtained in the hydrogenation step a) can be subjected to a work-up before a subsequent reaction. This may involve, for example, the removal of unreacted phosphabenzene, e.g. by fractional distillation or by crystallization of the phosphacyclohexenes and/or phosphacyclohexanes.

The compounds V.a, V.b and/or V.c are also suitable as ligands for transition metal catalysts to be used in hydroformylation. However, the catalytic activity of the resulting hydroformylation catalysts is generally lower than that of the subsequent products which are substituted in the 1 position. The compounds V.a to V.c are also valuable intermediates in the preparation of the ligands of the invention and ligands used according to the invention. It is generally possible to use both individual compounds which are unsubstituted in the 1 position and also product mixtures.

Step b1)

A first embodiment of the process of the invention for preparing phosphacyclohexenes and/or phosphacyclohexanes which are substituted in the 1 position comprises the reaction steps a) hydrogenation of at least one phosphabenzene and b1) reaction of the hydrogenation product(s) with at least one ethylenically unsaturated compound. The reaction step b1) is carried out according to one of the following three reaction variants:

I) in the presence of at least one free-radical former,
II) in the presence of at least one acid or at least one base or at least one transition metal compound,
III) at an elevated temperature in the range from 100 to 250° C.

Compounds suitable for the reaction in reaction step b1) are in principle all compounds which contain one or more ethylenically unsaturated double bonds. These include, for example, olefins such as α-olefins, internal straight-chain and internal branched olefins, functionalized olefins, oligomeric and polymeric compounds which contain at least one ethylenically unsaturated double bond etc.

The reaction step b1) can, if desired, be carried out in the presence of a solvent. Suitable solvents include aromatics such as benzene, toluene and xylenes, cycloalkanes such as cyclohexane, aliphatic hydrocarbons, etc. In a useful embodiment, the reaction is carried out in the olefin to be reacted as solvent; this olefin is generally used in a large molar excess over the phosphacyclohexene or phosphacyclohexane.

Preference is given to a process for preparing phosphacyloyexanes of the formula III by
a) hydrogenation of phosphabenzenes of the formula IV,

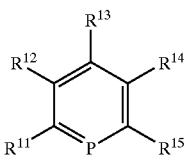

(IV)

and
b1) reaction with olefins of the formula $R^{16}R^{17}C=CR^{18}R^{19}$.

In this embodiment, 1-alkylphosphacyclohexanes can be obtained by a simple route according to the following reaction scheme by a) hydrogenation of phosphabenzenes and subsequent addition b1) of an olefin onto the PH function formed. Phosphacyclohexenes may also be formed to some extent in this way. They too are catalytically active.

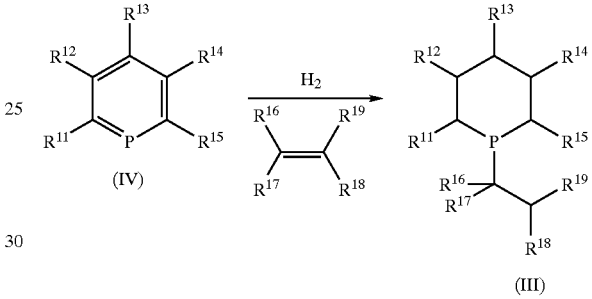

In these formulae,
$R^{11}$ to $R^{19}$ are each, independently of one another, hydrogen, $C_{1-20}$-alkyl, $C_{7-20}$-aralkyl, $C_{7-20}$-alkaryl, $C_{6-12}$-aryl, where one or more carbon atoms may be replaced by heteroatoms, $W'COO^-M^+$, $W'SO_3^-M^+$, $W'PO_3^{2-}M^+{}_2$, $W'NR'_3{}^+X^-$, $W'OR'$, $WNR'_2$, $W'COOR'$, $W'SR'$, $W'(CHR'CH_2O)_xR'$, $W'(CH_2NR')_xR'$, $W'(CH_2CH_2NR')_x R'$, where in each case two vicinal radicals $R^{11}$ to $R^{15}$ and/or $R^{17}$ and $R^{18}$ and/or $R^{16}$ and $R^{17}$ and/or $R^{16}$ and $R^{19}$ and/or $R^{18}$ and $R^{19}$ may be joined to form fused-on aliphatic or aromatic rings, W' is a single bond or a bridge having from 1 to 20 carbon atoms which may be part of a cyclic or aromatic group,
R' is hydrogen or $C_{1-6}$-alkyl,
M+ is a cation,
X− is an anion,
x is from 1 to 240, where one or more radicals $R^{11}$ to $R^{19}$ may bear an additional trivalent phosphorus or nitrogen group capable of coordination, and $R^{18}$ may also be $-W'-CR^{20}=CR^{21}R^{22}$, where $R^{20}$, $R^{21}$, $R^{22}$ are as defined above for $R^{11}$ to $R^{19}$. In this case, one or both double bonds may undergo an addition reaction.

Particularly preferred phosphabenzene compounds for preparing the compounds of the formula III are those of the formula IV.a, as described above.

As olefins $R^{16}R^{17}C=CR^{18}R^{19}$, it is possible to use any olefins as indicated above, for example α-olefins, internal and internal branched olefins having from, for example, 2 to 24 carbon atoms. Preference is given to α-olefins in which $R^{16}$ and $R^{17}$ or $R^{18}$ and $R^{19}$ are hydrogen. Particularly useful olefins are ethene, propene, isobutene, 1-hexene, 1-octene, 1-decene, 1-dodecene and cyclohexene. Also suitable are polyisobutenes which still contain at least one ethylenically unsaturated double bond. Functionalized olefins can also be used. These include polyalkylene glycols having at least one terminal vinyl group, e.g. vinylpolyethylene glycol monomethyl ether and vinylpolytetrahydrofuran. Further suitable olefins are divinyl compounds, which then result in phosphacyclohexanes and/or phosphacyclohexenes bridged via the P atoms.

In the case of the in-situ preparation of the compounds of the formula III, it is advantageous to use the olefin which is also used in the hydroformylation process employed according to the present invention. Particular preference is given to α-olefins or internal, linear olefins or mixtures comprising these olefins.

Suitable phosphabenzenes apart from the above-described compounds are, in particular, 2,4,6-triarylphosphabenzenes, 2,3,5,6-tetraarylphosphabenzenes and 2,3,4,5,6-pentaarylphosphabenzenes. Particular preference is given to 2,4,6-triarylphosphabenzenes. As mentioned above, phosphacyclohexanes and phosphacyclohexenes which are unsubstituted in the 1 position and may be present in traces are generally of lower catalytic activity. Treatment of the crude rhodium/phosphacyclohexane catalyst mixture with an olefin or olefin mixture in the presence of synthesis gas enables such compounds to be converted into a still more active catalyst system. This results in more active catalyst mixtures, as comparison of various hydroformylation experiments shows.

The hydrogenation of phosphabenzenes to form phosphacyclohexanes is carried out at the abovementioned temperatures and pressures. It can be carried out in the presence of pure hydrogen or hydrogen-containing gas mixtures such as synthesis gases.

The phosphabenzene/catalyst metal ratio in a batch process is in the range from 1 to 1 000, preferably in the range from 2 to 100 and in particular in the range from 2 to 20. The olefin/phosphabenzene ratio is in the range from 1 to 500, preferably in the range from 5 to 200 and in particular in the range from 10 to 80. In a continuous process, the ratio is in the range from 1 to 5 000, preferably from 10 to 2 000, in particular from 20 to 1 500.

It is possible to introduce the olefin a little at a time during the reaction. Preference is given to a continuous process.

Particularly when using rhodium as catalyst metal in a homogeneous phase, the crude reaction product can be used directly in the hydroformylation without isolation of the cocatalyst. It is particularly advantageous to prepare the rhodium/phosphacyclohexane-containing hydroformylation catalyst in situ under hydrogenation conditions from the corresponding phosphabenzene or from another phosphacyclohexane precursor and a rhodium salt or a rhodium complex in the presence of the appropriate olefin, preferably in the same reactor which is later used for carrying out the hydroformylation. Particular preference is given to carrying out the hydrogenation first and the hydroformylation subsequently.

The conversion of the phosphabenzene IV into the phosphacyclohexane III according to the above-described preferred embodiment can be carried out stepwise or in a single stage (see reaction variant III). For example, the hydrogenation of the phosphabenzene IV to the corresponding 1-unsubstituted phosphacyclohexane can be carried out first, followed by the addition, if appropriate initiated by free-radical initiators, of an olefin onto the PH function of the intermediate to form the cocatalyst III.

Variant I)

In a preferred embodiment, the process of the present invention comprises two separate reaction steps a) and b1), with the reaction step b1) being carried out in the presence of at least one free-radical former.

Suitable free-radical formers are the customary polymerization initiators known to those skilled in the art, as are used for free-radical polymerization. Examples of such compounds are organic peroxides, for example peresters of carboxylic acids, e.g. tert-amyl perpivalate, tert-butyl perpivalate, tert-butyl perneohexanoate, tert-butyl perisobutyrate, tert-butyl per-2-ethylhexanoate, tert-butyl perisononanoate, tert-butyl permaleate, tert-butyl perbenzoate, percarbonates such as di(2-ethylhexyl) peroxodicarbonate, dicyclohexyl peroxodicarbonate, di(4-tert-butylcyclohexyl) peroxodicarbonate, ketone peroxides such as acetylacetone peroxide, methyl ethyl ketone peroxide, hydroperoxides such as tert-butyl hydroperoxide and cumene hydroperoxide, and azo initiators such as 2,2'-azobis(amidinopropane) dihydrochloride, 2,2'-azobis-(N,N'-dimethylene)isobutyramidine dihydrochloride, 2(carbamoylazo)isobutyronitrile, 2,2-azobisisobutyronitrile, 2,2-azobisisovaleronitrile, or 4,4'-azobis(4-cyanovaleric acid). These include, for example, the Vazo® products from DuPont, e.g. Vazo 52, 67 and 88, where the number indicates the temperature at which the initiator has a half-life of 10 hours.

The free-radical former is preferably used in an amount of from 0.001 to 10% by weight, particularly preferably from 0.01 to 5% by weight, based on the total amount of ethylenically unsaturated compounds.

When the reaction step b1) is carried out in the presence of at least one free-radical former, the reaction temperature is preferably from 20 to 200° C., particularly preferably from 50 to 150° C. A person skilled in the art will choose the appropriate reaction temperature on the basis of the decomposition temperature, i.e. the corresponding half-life of the initiator at this temperature.

Variant II)

In a further useful embodiment, the above-described process comprises two separate reaction steps a) and b1), with the step b1) being carried out in the presence of at least one acid or at least one base or at least one transition metal compound. Examples of suitable acids are mineral acids such as hydrochloric acid and sulfuric acid. Preference is given to using carboxylic acids such as acetic acid. Suitable bases are alkali metal bases such as sodium hydroxide, potassium hydroxide, sodium carbonate, sodium hydrogen carbonate, potassium carbonate and potassium hydrogen carbonate and alkaline earth metal bases such as calcium hydroxide, calcium oxide, magnesium hydroxide and magnesium carbonate and also ammonia and amines. Preference is given to using amines such as trimethyamine, triethylamine, triisopropylamine, etc. Suitable transition metal compounds are compounds and complexes of noble metals or transition metals as are customarily also used in the abovementioned hydrogenation catalysts. Preference is given to rhodium compounds and complexes. The latter make it possible, in an advantageous manner, to prepare the ligands of the present invention and ligands used according to the present invention and the hydroformylation catalysts based on them in situ.

Variant III)

In a further preferred embodiment, the process of the present invention comprises two separate reaction steps a) and b1), with the reaction step b1) being carried out at a temperature in a range from about 100 to 250° C. Thus, a purely thermal reaction of the phosphacyclohexenes and/or phosphacyclohexanes with ethylenically unsaturated compounds is generally also possible.

The reaction of variant III can be carried out in a plurality of stages, with the hydrogenation being carried out first (in the absence of ethylenically unsaturated compounds) and the reaction of the reaction product(s) with at least one ethylenically unsaturated compound being carried out subsequently. The reaction can also be carried out in a single stage in which the hydrogenation occurs in the presence of the ethylenically unsaturated compound or compounds. A catalyst based on rhodium is preferably used in the single-stage reaction.

Step b2)

A second embodiment of the process of the present invention for preparing phosphacyclohexenes and/or phosphacyclohexanes which are substituted in the 1 position comprises the reaction steps a) hydrogenation of at least one phosphabenzene to form phosphacyclohexanes and/or phosphacyclohexenes which are unsubstituted in the 1 position and b2) reaction of the hydrogenation product(s) with at least one compound of the formula R—X or X-W-Y, where X and Y are each a nucleophilically displaceable group (leaving group) and R and W are as defined above.

The nucleophilically displaceable groups (leaving groups) X and Y of the compounds of the formulae R—X and X-W-Y are the leaving groups known to those skilled in the art from nucleophilic substitution. Preference is given to the anions of strong acids, e.g. halides such as —Cl, —Br and —I or groups such as OH, p-CH$_3$C$_6$H$_4$—SO$_3$-(tosylates), p-BrC$_6$H$_4$SO$_3$-(brosylates) and F$_3$C—SO$_3$-(triflates).

The groups R and W can generally have all the above-mentioned meanings. Useful and preferred embodiments are as described above.

This process variant is advantageous for preparing phosphacyclohexenes and phosphacyclohexanes which are substituted in the 1 position and are unobtainable, or obtainable only with difficulty, by the above-described addition of ethylenically unsaturated compounds. The use of compounds of the formula X-W-Y results in bicyclic phosphacyclohexenes or physphacyclohexanes which are bridged in the 1 position, with bridges having any number of carbon atoms being possible. This method thus also makes possible, in particular, the preparation of bicyclic compounds having bridges in which an odd number of bridge atoms is present.

In a useful embodiment, the process comprises the steps a) and b2), with the hydrogenation products obtained in step a) being metallated on the phosphorus atom before reaction with at least one compound R—X or X-W-Y. Here, the term "metallation" refers to the formal replacement of the hydrogen atom by a metal atom. Reagents suitable for the metallation are quite generally strong bases, e.g. alkali metal hydrides and alkaline earth metal hydrides and also organometallic compounds of Li, Mg, Al, Sn and Zn. Preference is given to organoaluminum and organolithium compounds. These include, for example, n-butyllithium, sec-butyllithium, tert-butyllithium, phenyllithium, etc. Further suitable metallation reagents are 2,2,6,6-tetramethylpiperidinelithium, hexamethyldisilazanelithium, lithium dicyclohexylamide and lithium diisopropylamide.

The above-described process comprising the reaction steps a) and b2) is advantageous for preparing the following compounds:

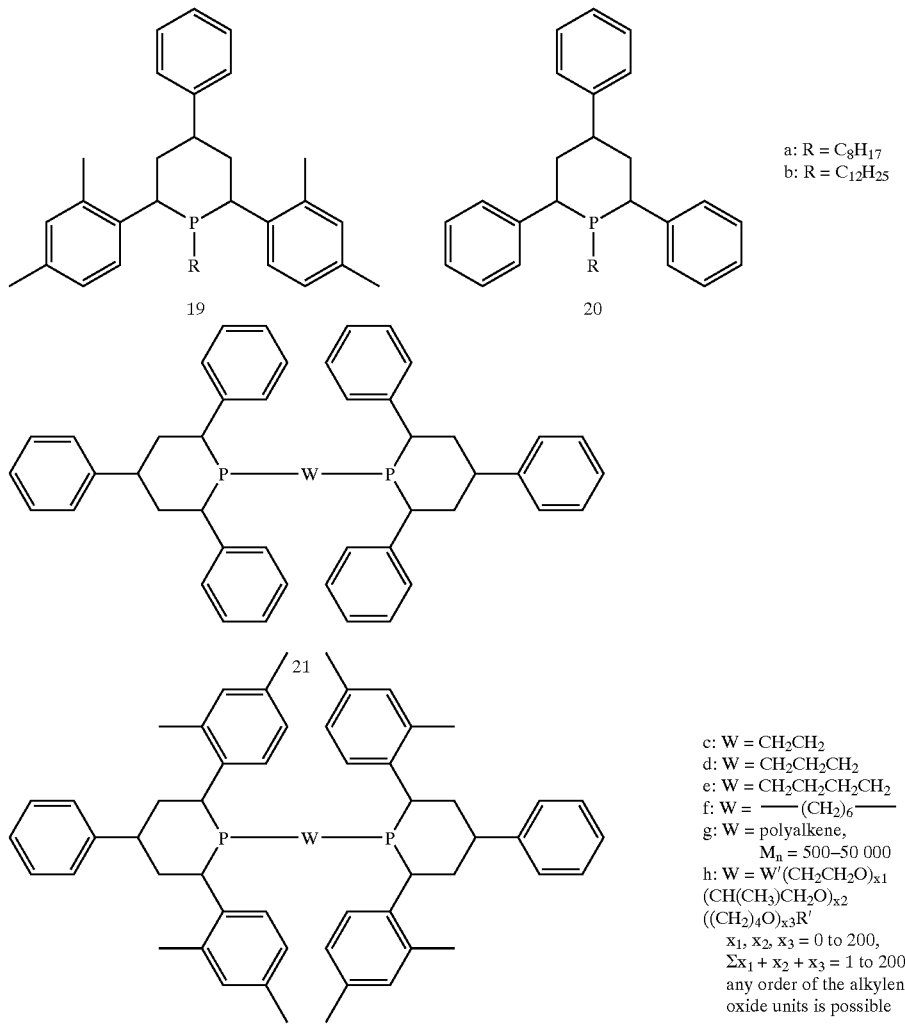

The invention further provides a process for preparing at least one phosphacyclohexane of the formulae VI.a and/or VI.b

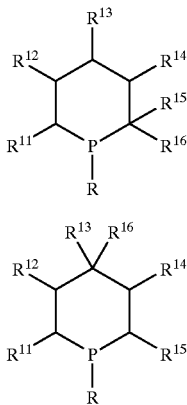

where
R is $C_{1-100}$-alkyl, cycloalkyl, heterocycloalkyl, $C_{7-20}$-aralkyl, $C_{7-20}$-alkaryl, $C_{6-12}$-aryl, hetaryl, W'COO$^-$M$^+$, W'SO$_3^-$M$^+$, W'PO$_3^{2-}$M$^+_2$, W'NR'$_3^+$X$^-$, W'OR', W'NR'$_2$, W'COOR', W'SR', W'(CHR'CH$_2$O)$_x$R', W'(CH$_2$NR')$_x$R', W'(CH$_2$CH$_2$NR')$_x$R', W'((CH$_2$)$_4$O)$_x$R' or W'COR', where two radicals R may also together form a bridging group W which covalently joins two identical or different units VI.a or VI.b to one another, $R^{11}$ to $R^{16}$ are each, independently of one another, hydrogen, $C_{1-20}$-alkyl, $C_{7-20}$-aralkyl, $C_{7-20}$-alkaryl, $C_{6-12}$-aryl, where one or more carbon atoms may be replaced by heteroatoms, W'COO$^-$M$^+$, W'SO$_3^-$M$^+$, W'PO$_3^{2-}$M$^+_2$, W'NR'$_3^+$X$^-$, W'OR', W'NR$_2$, W'COOR', W'SR', W'(CHR'CH$_2$O)$_x$R', W'(CH$_2$NR')$_x$R', W'(CH$_2$CH$_2$NR')$_x$R', W'((CH$_2$)$_4$O)$_x$R', W'halogen, W'NO$_2$, W'COR' or W'CN, where one or more hydrogen atoms in the radicals $R^{11}$ to $R^{16}$ may be replaced by fluorine, where two radicals $R^{16}$ may also together form a bridging group W which covalently joins two identical or different units VI.a or VI.b to one another, W and W' are, independently of one another, single bonds or bridges having from 1 to 20 carbon atoms which may be part of a cyclic or aromatic group and may be interrupted by heteroatoms, where W may also be a polyoxyalkylene or polyalkylenimine bridge having at least 21 carbon atoms, R' is hydrogen, $C_{1-20}$-alkyl, carbonylalkyl, cycloalkyl or aryl, M+ is a cation equivalent, X$^-$ is an anion equivalent and x is an integer from 1 to 240, where one or more of the radicals $R^{11}$ to $R^{16}$ may bear an additional trivalent phosphorus or nitrogen group capable of coordination, where one of the radicals R or $R^{11}$ to $R^{16}$ or, if present, a group W in the compounds of the formula VI.a or VI.b may also be a polymer radical having a number average molecular weight in the range from 500 to 50 000, and made up of repeating units derived from monomers selected from among monoolefins and diolefins, vinylaromatics, esters of α,β-ethylenically unsaturated monocarboxylic and dicarboxylic acids with $C_1$–$C_{30}$-alkanols, N-vinyl amides, N-vinyl lactams, heterocyclic compounds which can be polymerized with ring opening and mixtures thereof, which comprises A) reacting at least one phosphabenzene of the formula IV

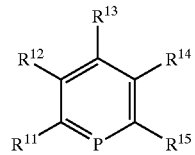

where $R^{11}$, $R^{12}$, $R^{13}$, $R^{14}$ and $R^{15}$ are as defined above, with an organometallic compound R-Me or Me-W-Me', where R and W are as defined above and Me and Me' are each a metal atom or a group containing a metal atom, and subsequently with at least one compound of the formula $R^{16}$—X or X-W-Y, where X and Y are nucleophilically displaceable groups and $R^{16}$ and W are as defined above, and B) hydrogenating the reaction product(s) obtained in step A) by means of hydrogen in the presence of a hydrogenation catalyst.

As regards useful and preferred radicals R, $R^{11}$ to $R^{16}$, W and W', what has been said above applies.

Step A)

Phosphabenzene compounds of the formula IV which are useful and preferred as starting materials are those mentioned above.

In the compounds R-Me and Me-W-Me', Me and Me' are each a metal atom or a group containing a metal atom. If Me is a metal atom, it is preferably a monovalent metal, in particular Li. Suitable compounds R-Me in which Me is a monovalent metal are the organolithium compounds mentioned above as reagents for the metallation, e.g. n-butyllithium, sec-butyllithium, tert-butyllithium and phenyllithium.

Suitable compounds R-Me can also be obtained by transmetallation, i.e. replacement of the metal atoms. If, for example, the metal-containing products of an anionic polymerization (as described below) are used for the transmetallation, this results in compounds R-Me in which R is a polymer radical. In this way, it is possible to provide phosphacyclohexanes which bear a polymer radical in the 1 position.

If Me or Me' in the compounds R-Me and Me-W-Me' is a group containing a metal atom, this is a divalent or polyvalent metal atom which additionally bears at least one further radical R or a radical different from R. This can be, for example, a halide. Preferred compounds R-Me and Me-W-Me' in which Me and/or Me' is a group containing a metal atom are Grignard compounds (organometallic compounds of magnesium). Grignard compounds and methods of preparing them are known to those skilled in the art. Preference is given to n-$C_4H_9$—Mg—Cl and $C_8H_{17}$—Mg—Cl. Use of compounds of the formula Me-W-Me' results in bicyclic phosphacyclohexanes which are bridged in the 1 position in each ring.

Suitable compounds of the formula $R^{16}$—X and X-W-Y are the abovementioned compounds of the formula R—X or X-W-Y, where X and Y are each a nucleophilically displaceable group (leaving group). Suitable leaving groups are those mentioned above. Suitable compounds of the formula $R^{16}$—X are water and alcohols. Use of compounds of the formula X-W-Y results in bicyclic 2,2'-, 2,4'- and 4,4'-linked phosphacyclohexadienes. In this way, this process makes it possible, in particular, to prepare bicyclic compounds which are bridged via positions other than the 1 position.

In a preferred embodiment, the organometallic compound used in step a) is a compound of the formula R-Me in which R is a radical comprising repeating units derived from anionically polymerizable monomers.

Processes for the anionic oligomerization and polymerization of monomers in the presence of an organometallic compound are known in principle.

In Anionic Polymerisation, Principles and Practical Applications, Marcel Dekker-Verlag (1996), chapter II, 5, pp. 93–116, H. L. Hsieh and R. P. Quirk describe suitable monomers and general aspects of anionic polymerization. The polymerization of styrene-butadiene is described in chapter III, pp. 131–258, the preparation of block copolymers is described in chaper IV, pp. 261–368, telechelic polymers are described in chapter V, 22, pp. 621–638, and (meth)acrylates are described in chapter VI, 23, pp. 641–684. Chapter VI, 24, pp. 685–710, describes ring-opening anionic polymerization. The abovementioned literature references are hereby incorporated by reference into the present application.

Ethylenically unsaturated compounds suitable for anionic polymerization are ethene and preferably acceptor-substituted ethylenically unsaturated compounds. These include, for example, vinylaromatics such as styrene, aromatic-substituted monoolefins such as 1,1-diphenylethylene, 1,2-diphenylethylene and mixtures thereof. Also suitable are conjugated dienes such as butadiene, isoprene, 2,3-dimethylbutadiene, 1,3-pentadiene and mixtures thereof. Suitable anionically polymerizable monomers are the abovementioned esters of α,β-ethylenically unsaturated monocarboxylic and dicarboxylic acids with $C_{1-30}$-alkanols. Heterocyclic compounds which can be polymerized with ring opening represent further suitable anionically polymerizable monomers. These include, preferably, the abovementioned alkylene oxides such as ethylene oxide and 1,2-propylene oxide, aziridines, lactones such as e-caprolactone and lactams such as ε-caprolactam. When using monomers having a lower reactivity, the polymerization can be carried out in the presence of at least one ether or amine, in particular an amine which has no amine hydrogens. Preference is given to amines which have two or more amino groups which bear no amine hydrogens. Preference is given, for example, to tetramethylethylenediamine (TMEDA).

When using conjugated dienes, for example butadiene, the proportion of 1,2 and 1,4 repeating units in the resulting polymer can be adjusted by customary methods known to those skilled in the art, e.g. by addition of donor solvents such as ethers, e.g. THF or dimethoxyethane, or amines. This makes it possible to prepare polymers having a variable degree of crystallinity ranging from highly crystalline to noncrystalline (generally >40% by weight of 1,2-vinyl units). Anionic polymerization is advantageous for the preparation of ethene-propene copolymers by hydrogenation of the corresponding 1,4-polyisoprenes. It is also advantageous for preparing block copolymers which are otherwise difficult to obtain, e.g. styrene-butadiene, styrene-isoprene, butadiene-(meth)acrylate or styrene-(meth)acrylate block copolymers. It is also advantageous for preparing random copolymers such as styrene-butadiene copolymers, in which case the polymerization may then be carried out in the presence of randomizers such as the above-mentioned donor solvents or alkali metal or alkaline earth metal salts, e.g. KOR or $Ba(OR)_2$.

Use of dienes such as butadiene for the anionic polymerization results in phosphacyclohexadienes whose 1 position is occupied by a polyalkylene radical which still has unsaturated side chains (1,2 product) or has double bonds in the main chain (1,4 product). These are completely or virtually completely converted into the corresponding alkyl radicals in the subsequent hydrogenation step b).

The reaction product obtained in step A) comprises at least one phosphacyclohexadiene of the formula VII.a or VII.b

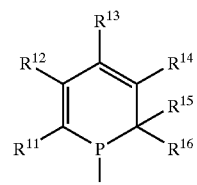

(VII.a)

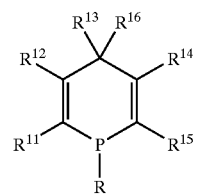

(VII.b)

or an isomer mixture thereof, where R and $R^{11}$ to $R^{16}$ are as defined above.

Step B)

Catalysts suitable for the hydrogenation of phosphacyclohexadienes to form phosphacyclohexadienes are the homogeneous or heterogeneous catalysts mentioned above for the hydrogenation of phosphabenzenes. Preference is given to using catalysts based on ruthenium or rhodium, in particular rhodium.

The temperature in the hydrogenation is preferably in a range from 20 to 250° C., particularly preferably from 50 to 180° C. and in particular from 80 to 160° C. In a preferred embodiment, the hydrogenation is firstly carried out at a temperature in the range from about 60 to 120° C. until virtually no cyclohexadienes are present in the reaction mixture, since these tend to aromatize. This results in hydrogenation products comprising predominantly or consisting of phosphacyclohexenes. Such hydrogenation products are preferably prepared using a catalyst based on rhodium. Like the phosphacyclohexanes, phosphacyclohexenes are, if appropriate after a subsequent reaction, suitable as ligands for transition metal catalysts for hydroformylation. If essentially complete hydrogenation is desired, the temperature is subsequently increased to 250° C. in order to complete the hydrogenation. The reaction pressure is preferably in the range from ambient pressure to 600 bar, particularly preferably from 5 to 100 bar and in particular from 10 to 80 bar.

If desired, at least one olefin can be added to the hydrogenation so as to convert any unreacted phosphabenzene still present in the reaction mixture into catalytically active species, as described above.

The invention further provides a process for preparing at least one phosphacyclohexane of the formula V

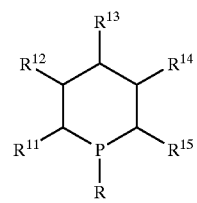

(V)

in which

R is hydrogen, $C_{1-100}$-alkyl, cycloalkyl, heterocycloalkyl, $C_{7-20}$-aralkyl, $C_{7-20}$-alkaryl, $C_{6-12}$-aryl, hetaryl, W'COO$^-$M$^+$, W'SO$_3^-$M$^+$, W'PO$_3^{2-}$M$^+_2$, W'NR'$_3^+$X$^-$, W'OR', W'NR'$_2$, W'COOR', W'SR', W'(CHR'CH$_2$O)$_x$R', W'(CH$_2$NR')$_x$R', W'(CH$_2$CH$_2$NR')$_x$R', W'((CH$_2$)$_4$O)$_x$R' or W'COR', where the radicals R or one of the radicals $R^{11}$ to $R^{15}$ in each of two identical or different units V may together be a bridging group W which covalently joins these units to one another, $R^{11}$ to $R^{15}$ are each, independently of one another, hydrogen, $C_{1-20}$-alkyl, $C_{7-20}$-aralkyl, $C_{7-20}$-alkaryl, $C_{6-12}$-aryl, where one or more carbon atoms may be replaced by heteroatoms, W'COO$^-$M$^+$, W'SO$_3^-$M$^+$, W'PO$_3^{2-}$M$^+_2$, W'NR'$_3^+$X$^-$, W'OR', W'NR'$_2$, W'COOR', W'SR', W'(CHR'CH$_2$O)$_x$R', W'(CH$_2$NR')$_x$R', W'(CH$_2$CH$_2$NR')$_x$R', W'((CH$_2$)$_4$O)$_x$R', W'halogen, W'NO$_2$, W'COR' or W'CN, where one or more hydrogen atoms in the radicals R and $R^{11}$ to $R^{15}$ may be replaced by fluorine, W and W' are, independently of one another, single bonds or bridges having from 1 to 20 carbon atoms which may be part of a cyclic or aromatic group and may be interrupted by heteroatoms, where W may also be a polyoxyalkylene or polyalkylenimine bridge having at least 21 carbon atoms, R' is hydrogen, $C_{1-20}$-alkyl, carbonylalkyl, cycloalkyl or aryl, M+ is a cation equivalent, X$^-$ is an anion equivalent and x is an integer from 1 to 240, where one or more of the radicals R and $R^{11}$ to $R^{15}$ may bear an additional trivalent phosphorus or nitrogen group capable of coordination, where one of the radicals R or $R^{11}$ to $R^{15}$ or, if present, a group W in the compounds of the formula V may also be a polymer radical having a number average molecular weight in the range from 500 to 50 000 and made up of repeating units derived from monomers selected from among monoolefins and diolefins, vinylaromatics, esters of α,β-ethylenically unsaturated monocarboxylic and dicarboxylic acids with $C_{1-30}$-alkanols, N-vinyl amides, N-vinyl lactams, heterocyclic compounds which can be polymerized with ring opening and mixtures thereof, which comprises α) reacting at least one pyrylium salt of the formula IX

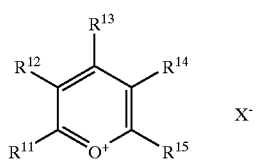

(IX)

where $R^{11}$, $R^{12}$, $R^{13}$, $R^{14}$ and $R^{15}$ are as defined above and X$^-$ is an anion equivalent, with a compound of the formula R—PH$_2$ or H$_2$P-W-PH$_2$, where R and W are as defined above, β) hydrogenating the reaction product(s) obtained in step α) by means of hydrogen in the presence of a hydrogenation catalyst, and γ) reacting the hydrogenation product(s) from step β) with at least one reducing agent, where the steps β) and γ) may be carried out in any order.

Processes for preparing suitable pyrylium salts are described, for example, in Houben-Weyl, Hetarene II, Part 2, editor: R. Kreher, Volume E7b, p. 755 ff, Thieme-Verlag, Stuttgart. Suitable pyrylium salts and processes for preparing them are also described in DE-A-197 43 197, which is hereby fully incorporated by reference.

Suitable anion equivalents of the pyrylium salts are selected from among ferrates, zincates, chlorides, borates which may be substituted by a $C_{1-6}$-alkyl radical, triflates, trifluoroacetates, tetrafluoroborates, perchlorates, hydrogensulfates, bromides, iodides or mixtures thereof. Preference is given to using tetrafluoroborates. The radicals $R^{11}$ to $R^{15}$ in the pyrylium salts correspond to the suitable and preferred radicals $R^{11}$ to $R^{15}$ indicated above.

As regards suitable and preferred radicals R and W in the monovalent phosphines R—PH$_2$ and divalent phosphines H$_2$P-W-PH$_2$, what has been said above applies. The use of compounds of the formula H$_2$P-W-PH$_2$ results in bicyclic phosphacyclohexanes which may be bridged in the 1 position.

The radical R is preferably $C_{1-20}$-alkyl, for example methyl, ethyl, n-propyl, n-butyl, pentyl, hexyl, heptyl, octyl, etc., or $C_{5-8}$-cycloalkyl, e.g. cyclohexyl. Preference is also given to R being a polymer radical as described above, particularly preferably a polyalkene radical such as a polyethylene radical or polyisobutene radical.

The reaction temperature in step α) is preferably from about 50 to 150° C., particularly preferably from 60 to 140° C.

The reaction may be carried out in the presence of a solvent or diluent. Suitable solvents or diluents are, for example, $C_{1-6}$-alkanols such as methanol, ethanol, n-propanol, isopropanol, n-butanol, isobutanol, tert-butanol, etc.

Step β)

Suitable catalysts for the hydrogenation of the reaction products obtained in step α) are generally all homogeneous or heterogeneous hydrogenation catalysts as have been described above for the hydrogenation of phosphabenzenes to form phosphacyclohexenes and/or phosphacyclohexanes. Preference is given to using ruthenium-containing catalysts, which may be used in the form of salts or complexes. These include, for example, ruthenium(III) acetylacetonate. Preference is also given to heterogeneous catalysts such as Pd on activated carbon.

The temperature in the hydrogenation is preferably in a range from 20 to 250° C., particularly preferably from 50 to 180° C. and in particular from 60 to 160° C. The reaction pressure is preferably in the range from ambient pressure to 600 bar, particularly preferably from 5 to 100 bar and in particular from 10 to 80 bar.

The hydrogenation in reaction step β) can be carried out in the presence of pure hydrogen or in the presence of hydrogen-containing gas mixtures such as synthesis gas.

Step γ)

Suitable reducing agents are the customary reducing agents known to those skilled in the art for the reduction of phosphine oxides to phosphines. These include, preferably, chlorosilanes such as trichlorosilane and complex hydrides such as LiAlH$_4$, BH$_3$/DMS (dimethyl sulfide), LiAlH$_4$/Cer (III).

The reaction steps β) and γ), i.e. the hydrogenation and the reduction, can be carried out in any order.

The ligand can be isolated by, for example, direct fractional distillation or crystallization.

The invention also provides a process for the hydroformylation of olefins by means of CO/H$_2$ in the presence of complexes of transition metals of transition group VIII of the Periodic Table at from 20 to 250° C. and pressures of from 1 to 600 bar, in which catalysts comprising phosphacyclohexanes I and II capable of complex formation as ligands are used.

The invention further provides a catalyst comprising at least one complex of a metal of transition group VIII with at least one phosphacyclohexane and/or phosphacyclohexene ligand, as defined above. The catalysts may further comprise at least one additional ligand selected from among halides, amines, carboxylates, acetylacetonates, arylsulfonates and alkylsulfonates, hydride, CO, olefins, dienes, cycloolefins, nitriles, N-containing heterocycles, aromatics and heteroaromatics, ethers, PF$_3$, phospholes, phosphabenzenes and monodentate, bidentate and polydentate phosphine, phosphinite, phosphonite, phosphoramidite and phosphite ligands.

The metal of transition group VIII is preferably selected from among cobalt, ruthenium, iridium, rhodium, nickel or palladium.

The catalysts which are active in the hydroformylation are generally transition metal complexes of the formula $ML_n(CO)_m$, where M is an element of transition group VIII of the Periodic Table, L is at least one monodentate or polydentate phosphacyclohexane ligand capable of complex formation and n and m are integers from 1 to 3. Further radicals such as hydrido, alkyl or acyl radicals can also be present as ligands in the transition metal complex. Particular preference is given to using rhodium as transition metal.

The active carbonyl complex is generally formed in situ from a transition metal salt, preferably a rhodium salt, or a transition metal complex, preferably a rhodium complex, the ligand, hydrogen and carbon monoxide; however, it can also be prepared and used separately.

If the catalyst complexes are generated in situ, particular preference is given to using precursor complexes such as dicarbonylrhodium acetylacetonate, rhodium 2-ethylhexanoate or rhodium acetate in the presence of the corresponding phosphacyclohexane ligands. As an alternative, the precursor complexes can also be used in the presence of suitable phosphacyclohexane precursors, so that the actual cocatalyst is also formed under the reaction conditions.

The composition of the synthesis gas $CO/H_2$ used in the hydroformylation process of the present invention can vary within a wide range. For example, synthesis gas having $CO/H_2$ molar ratios of from 5:95 to 90:10 can be used successfully; preference is given to using synthesis gas having $CO/H_2$ ratios of from 40:60 to 70:30, in particular about 1:1.

The hydroformylation is carried out in a known manner at from 50 to 250° C., preferably from 70 to 180° C., and at pressures of from 5 to 600 bar, preferably from 10 to 100 bar. However, the optimum temperature and the optimum pressure depend on the olefin used.

Owing to the higher reactivity, α-olefins are particularly preferably hydroformylated at from 80 to 120° C. and pressures of from 10 to 40 bar. 1-Alkenes are preferably hydroformylated at from 80 to 120° C. The pressure is preferably in a range from 10 to 40 bar. Olefins having a vinylidene double bond are preferably hydroformylated at from 100 to 150° C. Here too, the pressure is preferably from 10 to 40 bar. A reaction at higher temperatures and higher pressures than those indicated above is not ruled out.

Owing to their lower reactivity, internal olefins and internal olefins which are branched on the double bond are particularly preferably hydroformylated at from 120 to 180° C. and pressures of from 40 to 100 bar.

The hydroformylation is generally carried out in the presence of a 1- to 1 000-fold molar excess, preferably a 2- to 100-fold excess, of the ligand, based on the amount of transition metal used.

Possible substrates for the hydroformylation process of the present invention are in principle all compounds which contain one or more ethylenically unsaturated double bonds. These include olefins such as α-olefins, internal straight-chain olefins or internal branched olefins having any number of carbon atoms, but in particular those having from 2 to 14 carbon atoms and those having internal and internal branched double bonds. Examples of olefins which may be mentioned are the following: ethene, propene, 1-butene, 1-hexene, 1-octene, α-$C_{5-20}$-olefins, 2-butene, linear internal $C_{5-20}$-olefins and isobutene.

Suitable branched, internal olefins are, preferably, $C_{4-20}$-olefins such as 2-methyl-2-butene, 2-methyl-2-pentene, 3-methyl-2-pentene, branched, internal heptene mixtures, branched, internal octene mixtures, branched, internal nonene mixtures, branched, internal decene mixtures, branched, internal undecene mixtures, branched, internal dodecene mixtures, etc.

Further olefins suitable for the hydroformylation are $C_{5-8}$-cycloalkenes such as cyclopentene, cyclohexene, cycloheptene, cyclooctene and their derivatives, e.g. their $C_{1-20}$-alkyl derivatives having from 1 to 5 alkyl substituents. Additional olefins suitable for hydroformylation are vinylaromatics such as styrene, α-methylstyrene, 4-isobutylstyrene, etc.

Further olefins suitable for hydroformylation are ethylenically unsaturated polypropene and polyisobutene.

Functional groups are also possible. Examples are the following olefins: 3-pentenenitrile, 4-pentenenitrile, 3-pentenoic esters, 4-pentenoic esters, acrylic esters, vinyl glycol diacetate and butenediol diacetate. Dienes and polyenes having isolated or conjugated double bonds are also suitable substrates. The following olefins may be mentioned by way of example: 1,3-butadiene, 1,5-hexadiene, vinylcyclohexene, dicyclopentadiene, 1,5,9-cyclooctatriene, butadiene homopolymers and copolymers.

The unsaturated compound used for the hydroformylation is preferably selected from among internal linear olefins and olefin mixtures comprising at least one internal linear olefin. Preferred linear (straight-chain) internal olefins are $C_{4-20}$-olefins such as 2-butene, 2-pentene, 2-hexene, 3-hexene, 2-heptene, 3-heptene, 2-octene, 3-octene, 4-octene, etc., and mixtures thereof.

The hydroformylation process of the present invention is preferably carried out using an industrially available olefin mixture which comprises, in particular, at least one internal linear olefin. Such mixtures include, for example, the Ziegler olefins obtained by targeted ethene oligomerization in the presence of alkylaluminum catalysts. These are essentially unbranched olefins having a terminal double bond and an even number of carbon atoms. Suitable mixtures also include the olefins obtained by ethene oligomerization in the presence of various catalyst systems, e.g. the predominantly linear α-olefins obtained in the presence of alkylaluminum chloride/titanium tetrachloride catalysts and the α-olefins obtained in the presence of nickel-phosphine complexes as catalysts in the Shell Higher Olefin Process (SHOP). Suitable industrially available olefin mixtures are also obtained in paraffin dehydrogenation of appropriate petroleum fractions, e.g. kerosene or diesel oil fractions. The conversion of paraffins, predominantly n-paraffins, into olefins is carried out using essentially three processes:

thermal cracking (steam cracking)

catalytic dehydrogenation and chemical dehydrogenation by means of chlorination and dehydrochlorination.

Thermal cracking leads predominantly to α-olefins, while the other variants give olefin mixtures which generally have larger proportions of olefins having an internal double bond. Further suitable olefin mixtures are the olefins obtained in metathesis and telomerization reactions. These include, for example, the olefins from the Phillips triolefin process, a modified SHOP process comprising ethylene oligomerization, double bond isomerization and subsequent metathesis (ethenolysis).

Further industrial olefin mixtures which can be used in the hydroformylation process of the present invention may be selected from among dibutenes, tributenes, tetrabutenes, dipropenes, tripropenes, tetrapropenes, mixtures of butene isomers, in particular raffinate II, dihexenes, dimers and oligomers from the Dimersol® process of IFP, the Octol® process of Hüls, the Polygas process, etc.

1-Butene-containing hydrocarbon mixtures such as raffinate II are also preferred. Suitable 1-butene-containing hydrocarbon mixtures may contain a proportion of saturated hydrocarbons. Mixtures having a low proportion of high-boiling components are advantageous.

The reaction can be carried out in the presence of a solvent. Suitable solvents are, for example, ones selected from the group consisting of ethers, supercritical $CO_2$, fluorinated hydrocarbons and alkylaromatics such as toluene and xylene. However, the solvent can also be a polar solvent, for example a solvent selected from the group consisting of alcohols, dimethylacetamide, dimethylformamide or N-methylpyrrolidone. It is likewise possible to carry out the reaction in the presence of a high-boiling condensation product, e.g. an oligomeric aldehyde, in particular in the presence of an oligomer of the aldehyde to be prepared, which also functions as solvent here. The reaction can also be carried out in a two-phase mixture.

Since the catalysts used according to the present invention are frequently not only active in hydroformylation but also display some activity in the hydrogenation of aldehydes, the alcohols corresponding to the aldehydes can also be formed as products of value in addition to the aldehydes.

The output from the hydroformylation stage is depressurized prior to its work-up by distillation. This liberates unreacted synthesis gas which can be returned to the hydroformylation. The same applies for the unreacted olefin which has gone over into the gas phase in the depressurization and can, optionally after removal of inert hydrocarbons present therein by distillation, likewise be returned to the hydroformylation. The distillation of the depressurized hydroformylation mixture is generally carried out at pressures of from 0.1 to 1 000 mbar absolute, preferably from 1 to 500 mbar and particularly preferably from 10 to 400 mbar.

The temperature and the pressure which have to be set in the distillation are dependent on the type of hydroformylation product and the distillation apparatus used. For the process of the present invention, it is generally possible to use any distillation apparatuses. However, preference is given to using apparatuses which incur low capital costs and, especially for higher olefins, allow a low distillation temperature, e.g. thin film evaporators, wiped film evaporators or falling film evaporators, since the aldehydes present in the reactor output can undergo subsequent reactions such as aldol condensations at elevated temperatures. Since this distillation serves essentially to separate the hydroformylation products aldehyde and alcohol and any low boilers still present, e.g. unreacted olefin and inerts, from high-boiling condensation products of the aldehydes, known as high boilers, and the catalyst and excess ligand, it may be advantageous to subject the hydroformylation products and any olefins and inerts which have been separated off to further purification by distillation, which can be carried out in a conventional manner. This is intended, in particular, to avoid accumulation of high boilers still present.

An advantage of the process of the present invention is the opportunity of recirculating the catalyst complex and the excess ligand from the distillation residue from the reaction mixture. Alternative possibilities are a) the entire distillation bottoms in which the catalyst and excess ligand are present are recirculated, or
b) the catalyst and excess ligand are precipitated using a solvent in which the catalyst and the excess ligand are insoluble or virtually insoluble and only the precipitation product is recirculated, or
c) the high boilers present in the distillation bottoms are separated from the catalyst and excess ligand by means of steam distillation and only the distillation bottoms comprising catalyst and excess ligands obtained after the steam distillation are recirculated to the hydroformylation reaction, or
d) the catalyst and excess ligand are recovered by ultrafiltration of the distillation bottoms and the retentate is recirculated, or
e) the catalyst and excess ligand are recovered by extraction of the distillation bottoms, with a combination of at least two of the methods a) to e) being possible so as to avoid, for example, accumulation of high boilers in the circuit.

As an alternative, accumulation of high boilers in the reaction mixture of the hydroformylation can also be avoided by discharging part of the distillation bottoms from the process from time to time and passing this to further work-up for recovering the transition metal of transition group VIII of the Periodic Table and, if desired, the ligand used. In such a procedure, an amount of transition metal of transition group VIII of the Periodic Table and ligand or a suitable ligand precursor which forms the actual ligand under the reaction conditions of the hydroformylation corresponding to the amount of these compounds discharged should be replaced by introduction of these compounds into the hydroformylation reaction.

Method a)

Among the ligands which can be used according to the present invention, preference is given to those which have a boiling point sufficiently high for all the ligand-transition metal complex and all or at least the major part of ligand not required for complex formation to remain in the bottoms from the distillation of the reactor output and for the bottoms from this distillation to be able to be recirculated together with fresh olefin to the reaction.

This method surprisingly leads to excellent results in hydroformylation employing work-up of the reaction mixture by distillation, since the ligands used are very good stabilizers for the thermolabile catalyst and themselves have a high thermal stability. Losses of the ligand and the transition metal component of the catalyst can largely be avoided, even when a very inexpensive distillation with a low number of theoretical plates, e.g. thin film evaporator or falling film evaporator, is employed.

Since all high-boiling by-products are returned to the reaction in this variant of the process, some accumulation of high boilers occurs and it may be necessary to discharge high boilers continuously or periodically. This can be done, for example, by carrying out a separation of the catalyst complex and the excess ligand from the distillation bottoms according to the variants b) or c) described in more detail below and discharging the residue which comprises predominantly high boilers.

Method b)

In this method in which the catalyst complex and the excess ligand are precipitated, it is advantageous to use a solvent which is miscible over a wide range with the organic constituents of the distillation bottoms from the reactor output and in which the catalyst complex and the ligand are nevertheless insoluble or virtually insoluble, so that it is possible, by selection of type and amount of the solvent, to precipitate the catalyst complex and the ligand and, after they have been separated off by decantation or filtration, to return them to the hydroformylation.

As solvents, it is possible to use a large number of polar solvents, especially those containing hydroxyl, carbonyl, carboxamide or ether groups, i.e. alcohols, ketones, amides or ethers, and also mixtures of these solvents or mixtures of these solvents with water.

The type and amount of solvent to be employed can be specifically determined by a person skilled in the art by means of a few simple tests. In general, the amount of solvent is kept as small as possible so that the recovery is made as easy as possible. Accordingly, the amount required is generally from 1 to 50 times, preferably from 3 to 15 times, the volume of the distillation bottoms.

Method c)

A further method of discharging high-boiling condensation products of the aldehydes is to separate them from the distillation bottoms by means of steam distillation. The steam distillation of the distillation bottoms can be carried out batchwise or continuously, either in the distillation apparatus itself or in a separate apparatus for steam distillation. For example, in the batch method, the distillation bottoms can be freed of all or some of the high-boiling condensation products by passing steam through them before they are returned to the hydroformylation, or the distillation bottoms can, depending on the amount of high boilers formed, be subjected from time to time to steam distillation in a separate apparatus.

The method can be carried out continuously by, for example, continuously feeding the distillation bottoms or part of the distillation bottoms to a steam distillation apparatus and freeing them of all or part of the high boilers before the bottoms are returned to the hydroformylation. It is likewise possible to carry out the work-up by distillation of the output from the hydroformylation continuously from the start in the presence of steam in order to separate not only the aldehyde and the alcohol but also the high boilers simultaneously from the catalyst and the excess ligand. It is self-evident that in the case of such a procedure, the products of value have to be separated from high boilers and, if necessary, from water in a subsequent fractionation and distillation apparatus.

The steam distillation is generally carried out in a conventional manner by passing steam into the distillation bottoms comprising high boilers and subsequently condensing the steam distillate. The steam is advantageously passed through the distillation bottoms so that it does not condense in the distillation bottoms. This can be achieved by selection of the pressure and/or temperature conditions under which the steam distillation is carried out. For this purpose, it is possible to employ either reduced pressure or, when superheated steam is used, superatmospheric pressure. In general, the steam distillation is carried out at from 80 to 200° C. and a pressure of from 1 mbar to 10 bar, preferably from 5 mbar to 5 bar. The weight ratio of steam passed through the distillation bottoms to the high-boiling condensation products of aldehydes present in the bottoms (high boilers) is generally from 10:1 to 1:10. After the steam distillation is complete, the distillation bottoms which comprise catalyst and excess ligand and have been completely or partly freed of high boilers in this way can be returned to the hydroformylation.

As has already been mentioned above, it can be advantageous to combine the methods a) and b) or a) and c).

Method d)

Owing to the difference between the molecular weights of the catalyst complexes and excess ligands and the molecular weights of the high boilers remaining in the distillation bottoms, it is also possible to separate catalyst complexes and ligands from the high boilers by ultrafiltration. For this purpose, the mean molecular weight of the ligand is preferably more than 500 dalton, particularly preferably more than 1 000 dalton.

The process can be carried out continuously or batchwise. Embodiments of such processes are described in WO 99/36382, which is hereby incorporated by reference.

In a suitable continuous mode of operation, the starting materials are reacted in the presence of catalyst and ligands in a reactor. The output from the reactor is distilled in a distillation apparatus to separate it into a distillate stream comprising the oxo products and a residue. The catalyst-containing residue is fed continuously to a membrane filtration. Here, the residue comprising high boilers (or a mixture of high boilers, starting materials and oxo products), catalyst and ligands is worked up. The high boilers (and, if present, starting materials and oxo products) permeate through the membrane. The retentate stream which is depleted in high boilers (and, if present, starting materials and oxo products) and enriched in catalyst and ligands is recirculated to the hydroformylation.

In a suitable batchwise procedure, the starting materials are reacted in the presence of the catalyst and ligands in a reactor. At the end of the reactor, the crude reaction product is distilled in a distillation apparatus to separate it into a distillate stream comprising the oxo products and a residue stream. This catalyst-containing residue from the distillation is worked up in a membrane filtration. At the end of the ultrafiltration, the distillation residue which is depleted in high boilers (and, if present, starting materials and oxo products) and enriched in catalyst and ligands is returned to the reactor for the next hydroformylation batch.

The ultrafiltration can be carried out in one or more stages (preferably in two stages). In each stage, the feed solution is brought to filtration pressure, for example by means of a pump; flow over the membrane, i.e. wetting of the membrane, can be ensured by recirculating part of the retentate stream via a second pump. To avoid formation of an appreciable covering layer of catalyst on the membrane surface (concentration polarization), which can lead to a decrease in the permeate flux, a relative velocity between membrane and the catalyst-containing solution in the range from 0.1 to 10 m/s is preferably maintained. Further suitable measures for avoiding formation of a covering layer are, for example, mechanical agitation of the membrane or the use of stirrers between the membranes. In the multistage variant, the permeate stream from one stage is fed to the next stage and the retentate stream of this next stage is fed back to the previous stage. This work-up of the permeate enables better retention of the catalyst and the ligand to be achieved.

In the case of a multistage ultrafiltration, the various stages can be equipped with the same membranes or with different membranes.

The optimum transmembrane pressures between retentate and permeate are dependent on the diameter of the membrane pores and the mechanical stability of the membrane at the operating temperature and are essentially, depending on the type of membrane, in the range from 0.5 to 100 bar, preferably from 10 to 60 bar, at a temperature of up to 200° C. Higher transmembrane pressures and higher temperatures lead to higher permeate fluxes. The flow velocity over the membrane in the module is generally from 1 to 10 m/s, preferably from 1 to 4 m/s. The catalyst concentration in the feed solution to the membrane is preferably from 5 to 2 000 ppm.

Possible membranes for the ultrafiltration are all those which are stable in the reaction system. The separation limits of the membranes is from about 200 to 20 000 dalton, preferably from 500 to 5 000 dalton. The separation layers can comprise organic polymers, ceramic, metal or carbon and have to be stable in the reaction medium and at the process temperature. For mechanical reasons, the separation layers are generally supported on a monolayer or multilayer porous support structure made of the same material as the separation layer or of a plurality of different materials. Examples are:

| Separation layer | Support structure (coarser than separation layer) |
| --- | --- |
| Metal | Metal |
| Ceramic | Metal, ceramic or carbon |
| Polymer | Polymer, metal, ceramic or ceramic on metal |
| Carbon | Carbon, metal or ceramic |
| Ceramic: | e.g. $\alpha$-$Al_2O_3$, $\gamma$-$Al_2O_3$, $ZrO_2$, $TiO_2$, SiC, mixed ceramic materials |
| Polymer: | e.g. PTFE, PVDF, polysulfone, polyether sulfone, polyether ether ketone |

The membranes can be used in flat, tubular, multichannel element, capillary or wound geometries for which appropriate pressure housings which allow separation between retentate (catalyst-containing) and the permeate (catalyst-free filtrate) are available.

The following tables show examples of such membranes.

| Designation | Material | Separation limit | Manufacturer |
|---|---|---|---|
| MPF-U20-S | Polysulfone | 20 000 dalton | Membran Products Kiryat Weizmar |
| K00X1040 | TiO$_2$ on Al$_2$O$_3$—TiO$_2$ | 15 000 dalton | Tech-Sep |
| | TiO$_2$ | 500 to 10 000 dalton | Inocermic Gesellschaft für Innovative Keramik mbH |
| | TiO$_2$ | 5 000 dalton | Société des Céramiques Techniques |
| | TiO$_2$ on stainless steel | | Graver Chemical Company |

| Manufacturer | Membrane | Separation limit (kD) Pore diameter (nm) |
|---|---|---|
| Atech innovations GmbH | UF/TiO$_2$ on α-Al$_2$O$_3$ | 20 kD |
| Rhodia/Orelis | NF/ZrO$_2$ on ceramic | 1 kD |
| | UF/ZrO$_2$ or TiO$_2$ on ceramic | 15, 50, 150 kD |
| | UF/ZrO$_2$ on carbon | 15, 50, 150 kD |
| USF Filtration & Separation | NF/TiO$_2$ on ceramic | 1–5 kD |
| | UF/ZrO$_2$ on ceramic | 20 nm |
| Graver Technologies | UF/ceramic on steel | 20 kD |
| Inocermic GmbH | UF/ZrO$_2$ on ceramic | 3 nm |
| | UF/TiO$_2$ on ceramic | 5 nm |
| | NF/TiO$_2$ on ceramic | 0.9 nm/ 0.5 kD |
| Osmonics/Desal | UF/PVDF | 10 kD |
| NADIR Filtrations GmbH | UF/Polyether sulfone | 5–150 kD |

Method e)

As a further variant, the aldehydes/alcohols can be separated off first by distillation, after which the catalyst-containing bottoms are treated with a polar extractant, e.g. water. Here, the catalyst goes over into the polar phase, while high boilers remain in the organic phase. In this variant, preference is given to using catalysts bearing water-soluble (hydrophilic) ligands or ligands which can be converted into a water-soluble form. The catalyst can be recovered by reextraction or can be recirculated directly as such. As an alternative, the catalyst can be extracted by means of a nonpolar solvent, after which the high boilers are separated off.

As an alternative to work-up by distillation, the crude reaction product can also be worked up by extraction. For this purpose, a polar or nonpolar solvent, depending on the type of catalyst used, which is essentially immiscible with the crude reaction product or with at least one of the solvents which may be present in the crude reaction product is added to the crude reaction product. If desired, a two-phase mixture of at least one polar solvent and at least one nonpolar solvent can be added to the crude reaction product for the extraction. In the case of a two-phase reaction, the addition of a further solvent can generally be dispensed with. Phase separation in a suitable apparatus gives one phase comprising the hydroformylation products and higher-boiling condensation products and another phase comprising the catalyst. Particularly useful polar phases are water and ionic liquids, i.e. salts which have a low melting point. In such a hydroformylation process, preference is given to using phosphacyclohexane ligands containing ionic or polar groups so that a high solubility of the catalyst in the polar phase results and leaching of the catalyst into the organic phase is prevented or at least largely suppressed. Suitable substituents are, for example, W'COO$^-$M$^+$, W'SO$_3^-$M$^+$, W'PO$_3^{2-}$M$^{2+}$, W'NR'$_3$$^+$X$^-$, W'OR', WNR'$_2$, W'COOR', W'SR', W'(CHR'CH$_2$O)$_x$R', W'(CH$_2$NR')$_x$R' und W'(CH$_2$CH$_2$NR')$_x$R', where X–, M$^+$, R', W' and x are as defined above.

Phosphacyclohexanes bearing nonpolar radicals can also be removed by phase separation using a nonpolar solvent. Phosphacyclohexanes having lipophilic radicals are particularly useful. In this way, leaching of the catalyst can be at least largely suppressed.

In a preferred embodiment, the reaction mixture can also be worked up directly by means of ultrafiltration. Here, to separate off the catalyst and obtain a catalyst-free product or high boiler stream, the output from the synthesis is, as described, brought into contact with a membrane under pressure and permeate (filtrate) is taken off on the reverse side of the membrane at a pressure lower than on the feed side. This gives a catalyst concentrate (retentate) and a virtually catalyst-free permeate.

When the output from the synthesis is fed directly to the membrane process at the synthesis pressure, the transmembrane pressure can be adjusted by increasing the permeate pressure.

The essentially catalyst-free permeate obtained can be separated further into products and high boilers by customary methods known to those skilled in the art, for example distillation or crystallization.

When using α-olefins as feed in the hydroformylation process of the present invention, higher proportions of isoaldehydes in the aldehyde mixture can be obtained compared to a corresponding rhodium/triphenylphosphine-catalyzed hydroformylation process. This is advantageous for certain applications, e.g. for preparing neopentyl glycol.

The phosphacyclohexane ligands used according to the present invention have a high stability under hydroformylation conditions. The catalyst can be used in a continuous hydroformylation process for a number of weeks without loss in activity and without further addition of phosphacyclohexane ligand or a corresponding phosphacyclohexane precursor. No degradation of the ligand is observed.

The catalysts used according to the present invention in the hydroformylation reaction display high selectivity to aldehydes and alcohols. Paraffin formation by hydrogenation of alkenes is significantly reduced compared to a rhodium/triphenylphosphine-catalyzed hydroformylation process.

In a continuous hydroformylation process using rhodium/phosphacyclohexanes, it is possible, as an alternative to further addition of the phosphacyclohexane ligand, to add further amounts of the corresponding phosphabenzene or another phosphacyclohexane precursor which are converted under hydroformylation conditions in the presence of olefin into the corresponding phosphacyclohexane. The addition of the appropriate phosphabenzene precursor to a rhodium/phosphacyclohexane-catalyzed hydroformylation has no influence on the activity and the selectivity of the catalysis.

Phosphacyclohexanes and phosphacyclohexenes which are unsubstituted in the 1 position are generally of lower catalytic activity. Such compounds can be eliminated by treatment of the crude rhodium/phosphacyclohexane catalyst mixture with an olefin or olefin mixture in the presence of synthesis gas to give an even more active catalyst system. This results in more active catalyst mixtures, as shown by comparison of various hydroformylation experiments.

Apart from hydroformylation, the catalyst can also be used in other suitable reactions. Examples are hydroacylation, hydrocyanation, hydroamidation, hydroesterification, aminolysis, alcoholysis, hydrocarbonylation, hydroxycarbonylation, carbonylation, isomerization or transfer hydrogenation.

BRIEF DESCRIPTION OF DRAWINGS

FIGS. 2 and 3 show conversions, selectivities and space-time yields which were achieved in the representative continuous hydroformylation reactions The invention is illustrated by the examples below:

EXAMPLES

Example 1

Figure 1:
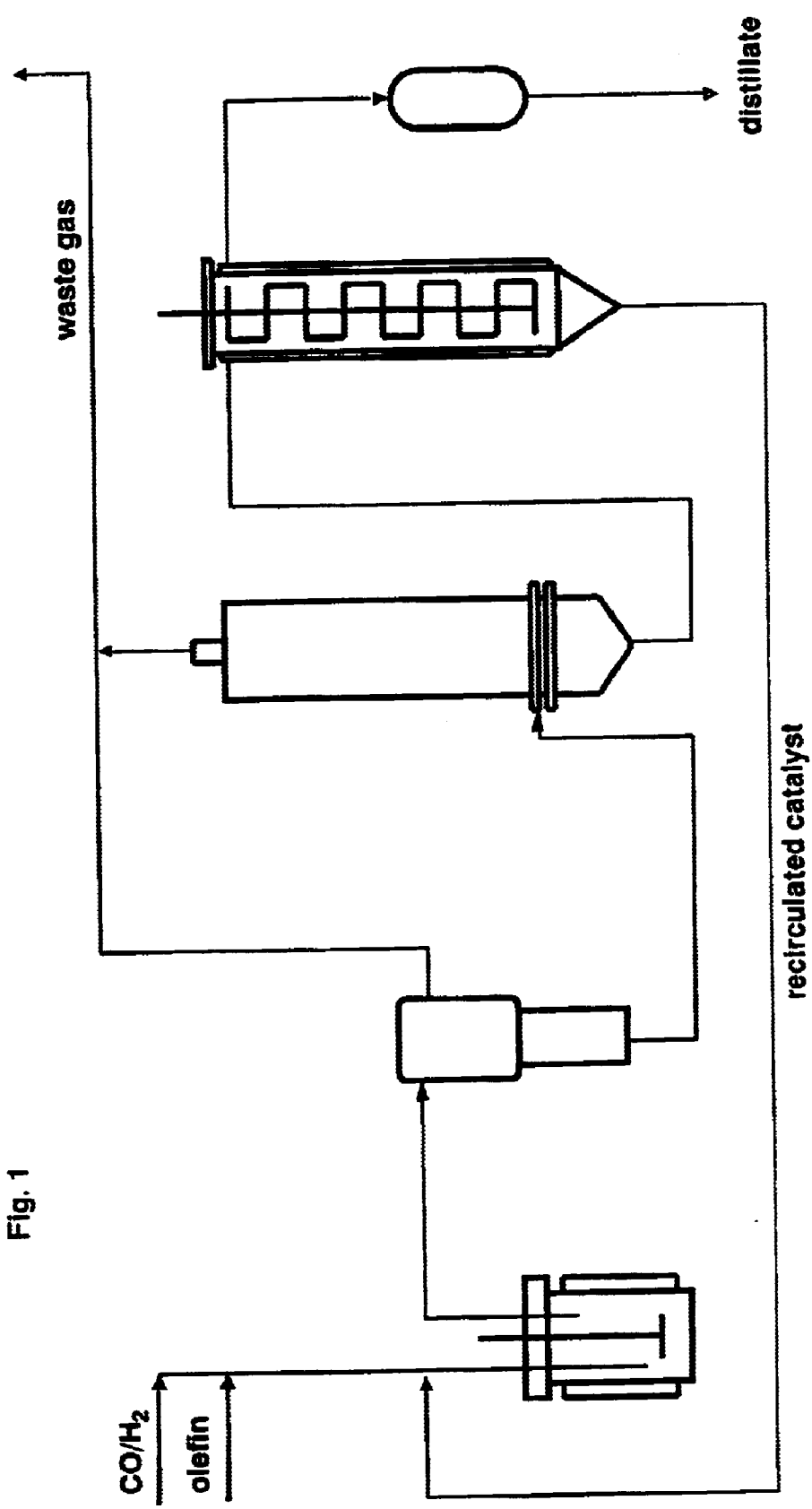
FIG. 1 illustrates a miniplant comprising a cascade of two reactors which was employed for representative continuous hydroformylation reactions conducted in the presence of the catalyst.

Preparation of a rhodium/2,6-bis(2,4-dimethylphenyl)-1-octyl-4-phenylphosphacyclohexane Solution 0.10 g (0.39 mmol) of dicarbonylrhodium acetylacetonate, 1.0 g (2.6 mmol) of 2,6-bis(2,4-dimethylphenyl)-4-phenylphosphabenzene and 10 g (89 mmol) of 1-octene were dissolved in 40 g of toluene under nitrogen in a Schlenk tube. The resulting solution was transferred to a 100 ml autoclave which had been flushed with hydrogen. The autoclave was pressurized with 5 bar of hydrogen. While stirring vigorously with a sparging stirrer, the reaction mixture was heated to 150° C. The hydrogen pressure in the autoclave was increased to 80 bar. The reaction mixture was then stirred at 150° C. for 72 hours. During the reaction, the pressure in the reactor was maintained by introduction of further hydrogen via a pressure regulator. After cooling to room temperature, another 3.0 g (27 mmol) of 1-octene were added to complete the reaction. The reaction was continued as described above at 150° C. and 80 bar hydrogen pressure for a further 24 hours. Cooling to room temperature resulted in a yellowish brown, homogeneous solution. The solution obtained was evaporated completely in a high vacuum and the residue was then taken up in 200 ml of toluene. Analysis of the solution indicated a rhodium content of 190 ppm and a phosphorus content of 400 ppm (P/Rh molar ratio=7). GC analysis (NP detector i.e. a detector sensitive to nitrogen and phosphorus) indicates a phosphabenzene conversion of 97%. The yield of 2,6-bis(2,4-dimethylphenyl)-1-octyl-4-phenylphosphacyclohexane was 81%, the yield of 2,6-bis(2,4-dimethylphenyl)-1-octyl-4-phenylphosphacyclohexenes was 8% and the yield of 2,6-bis(2,4-dimethylphenyl)$_4$-phenylphosphacyclohexane was 0.2%. The compounds could be confirmed by GC-MS analysis and $^{31}$P-NMR spectroscopy.

Example 2

Preparation of a rhodium/2,6-bis(2,4-dimethylphenyl)-1-octyl-4-phenylphosphacyclohexane Solution 0.10 g (0.39 mmol) of dicarbonylrhodium acetylacetonate, 1.0 g (2.6 mmol) of 2,6-bis(2,4-dimethylphenyl)-4-phenylphosphabenzene and 6.0 g (53 mmol) of 1-octene were dissolved in 6.0 g of toluene under nitrogen in a Schlenk tube. The resulting solution was transferred to a 100 ml autoclave which had been flushed with hydrogen. The autoclave was pressurized with 5 bar of hydrogen. While stirring vigorously with a sparging stirrer, the reaction mixture was heated to 150° C. The hydrogen pressure in the autoclave was increased to 80 bar. The reaction mixture was then stirred at 150° C. for 72 hours. During the reaction, the pressure in the reactor was maintained by introduction of further hydrogen via a pressure regulator. After cooling to room temperature, another 6.0 g (53 mmol) of 1-octene were added to complete the reaction. The reaction was continued as described above at 150° C. and 80 bar hydrogen pressure for a further 24 hours. Cooling to room temperature resulted in a yellowish brown, homogeneous solution. The solution obtained was evaporated completely in a high vacuum. The residue which remained was chromatographed over Silica 60 using a hexane/ethyl acetate mixture (4:1) as eluent. The solution obtained was once again evaporated completely in a high vacuum and subsequently chromatographed over Silica 60 using a hexane/ethyl acetate mixture (9:1) as eluent. The solution obtained was evaporated completely in a high vacuum and the residue was then taken up in 50 ml of toluene. Analysis of the solution indicated a rhodium content of 340 ppm and a phosphorus content of 790 ppm (P/Rh molar ratio=8). GC analysis (NP detector) indicates the following composition of the solution: 2% of 2,6-bis(2,4-dimethylphenyl)-4-phenylphosphabenzene, 86% of 2,6-bis(2,4-dimethylphenyl)-1-octyl-4-phenylphosphacyclohexane 10% of 2,6-bis(2,4-dimethylphenyl)-1-octyl-4-phenylphosphacyclohexenes and 2% of 2,6-bis(2,4-dimethylphenyl)-4-phenylphosphacyclohexane. The compounds could be confirmed by GC-MS analysis and $^{31}$P-NMR spectroscopy.

Example 3

Preparation of a rhodium/2,6-bis(2,4-dimethylphenyl)-1-propyl-4-phenylphosphacyclohexane Solution 0.044 g (0.17 mmol) of dicarbonylrhodium acetylacetonate and 1.5 g (3.9 mmol) of 2,6-bis(2,4-dimethylphenyl)$_4$-phenylphosphabenzene were dissolved in 30 g of toluene under nitrogen in a Schlenk tube. The resulting solution was transferred to a 100 ml autoclave which had been flushed with hydrogen. 6.0 g (143 mmol) of propene were then injected via a lock into the autoclave by means of hydrogen pressure. A pressure of 5 bar was then set by means of hydrogen. While stirring vigorously with a sparging stirrer, the reaction mixture was heated to 150° C. The hydrogen pressure in the autoclave was increased to 80 bar. The reaction mixture was then stirred at 150° C. for 72 hours. During the reaction, the pressure in the reactor was maintained by introduction of further hydrogen via a pressure regulator. After cooling to room temperature, the autoclave was depressurized to atmospheric pressure and another 8.0 g (190 mmol) of propene were added to the reaction. The reaction was continued as described above at 150° C. and 80 bar hydrogen pressure for a further 24 hours. After cooling to room temperature, the solution obtained was evaporated completely in a high vacuum and the residue which remained was taken up in 120 ml of toluene. GC analysis (NP detector) indicates a phosphabenzene conversion of 100%. The yield of 2,6-bis(2,4-dimethylphenyl)-1-propyl-4-phenylphosphacyclohexane was 61% and the yield of 2,6-bis(2,4-dimethylphenyl)-4-phenylphosphacyclohexane was 21%. The compounds could be confirmed by GC-MS-analysis and $^{31}$P-NMR spectroscopy.

Example 4

Preparation of a rhodium/2,6-bis(2,4-dimethylphenyl)-1-isobutyl-4-phenylphosphacyclohexane Solution 0.044 g (0.17 mmol) of dicarbonylrhodium acetylacetonate and 1.5 g (3.9 mmol) of 2,6-bis(2,4-dimethylphenyl)-

4-phenylphosphabenzene were dissolved in 30 g of toluene under nitrogen in a Schlenk tube. The resulting solution was transferred to a 100 ml autoclave which had been flushed with hydrogen. 6.0 g (107 mmol) of isobutene were then injected via a lock into the autoclave by means of hydrogen pressure. A pressure of 5 bar was then set by means of hydrogen. While stirring vigorously with a sparging stirrer, the reaction mixture was heated to 150° C. The hydrogen pressure in the autoclave was increased to 80 bar. The reaction mixture was then stirred at 150° C. for 72 hours. During the reaction, the pressure in the reactor was maintained by introduction of further hydrogen via a pressure regulator. After cooling to room temperature, the autoclave was depressurized to atmospheric pressure and another 6.0 g (107 mmol) of isobutene were added to the reaction. The reaction was continued as described above at 150° C. and 80 bar hydrogen pressure for a further 24 hours. Cooling to room temperature resulted in a yellowish brown, homogeneous solution. GC analysis (NP detector) indicates a phosphabenzene conversion of 47%. The yield of 2,6-bis(2,4-dimethylphenyl)-1-isobutyl-4-phenylphosphacyclohexane was 35%, the yield of 2,6-bis(2,4-dimethylphenyl)-1-isobutyl-4-phenylphosphacyclohexenes was 14% and the yield of 2,6-bis(2,4-dimethylphenyl)-4-phenylphosphacyclohexane was 19%. The compounds could be confirmed by GC-MS-analysis and $^{31}$P-NMR spectroscopy.

Example 5

Preparation of a rhodium/1-octyl-2,4,6-triphenylphosphacyclohexane Solution 0.10 g (0.39 mmol) of dicarbonylrhodium acetylacetonate, 1.3 g (4.0 mmol) of 2,4,6-triphenylphosphabenzene and 10 g (89 mmol) of 1-octene were dissolved in 20 g of toluene under nitrogen in a Schlenk tube. The resulting solution was transferred to a 100 ml autoclave which had been flushed with hydrogen. The autoclave was pressurized with 5 bar of hydrogen. While stirring vigorously with a sparging stirrer, the reaction mixture was heated to 150° C. The hydrogen pressure in the autoclave was increased to 80 bar. The reaction mixture was stirred at 150° C. for 24 hours. During the reaction, the pressure in the reactor was maintained by introduction of further hydrogen via a pressure regulator. Cooling to room temperature resulted in a brown, homogeneous solution. The solution obtained was evaporated completely in a high vacuum and the residue was then taken up in 200 ml of toluene. Analysis of the solution indicates a rhodium content of 200 ppm and a phosphorus content of 640 ppm (P/Rh molar ratio=11). GC analysis (NP detector) indicates a phosphabenzene conversion of 98%. The yield of 1-octyl-2,4,6-triphenylphosphacyclohexanes was 76% and the yield of 2,4,6-triphenylphosphacyclohexane was 9%. The compounds could be confirmed by GC-MS analysis and $^{31}$P-NMR spectroscopy.

Example 6

Preparation of a rhodium/2,6-bis(2,4-dimethylphenyl)-1-octyl-4-phenylphosphacyclohexane Solution 0.40 g (1.55 mmol) of dicarbonylrhodium acetylacetonate, 3.1 g (8.1 mmol) of 2,6-bis(2,4-dimethylphenyl)-4-phenylphosphabenzene and 10 g (89 mmol) of 1-octene were dissolved in 10 g of toluene under nitrogen in a Schlenk tube. The resulting solution was transferred to a 100 ml autoclave which had been flushed with hydrogen. The autoclave was pressurized with 5 bar of hydrogen. While stirring vigorously with a sparging stirrer, the reaction mixture was heated to 160° C. The hydrogen pressure in the autoclave was increased to 60 bar. The reaction mixture was then stirred at 160° C. for 24 hours. During the reaction, the pressure in the reactor was maintained by introduction of further hydrogen via a pressure regulator. After cooling to room temperature, another 10 g (89 mmol) of 1-octene were added to complete the reaction. The reaction was continued as described above at 160° C. and 60 bar hydrogen pressure for a further 96 hours. After the reaction time, the autoclave was cooled, vented and emptied. The solution obtained was evaporated completely in a high vacuum and the residue which remained was taken up in 200 g of toluene. Analysis of the solution indicated a rhodium content of 690 ppm and a phosphorus content of 1 100 ppm (P/Rh molar ratio=5). GC analysis (NP detector) indicates a phosphabenzene conversion of 95%. The yield of 2,6-bis(2,4-dimethylphenyl)-1-octyl-4-phenylphosphacyclohexane was 74%, the yield of 2,6-bis(2,4-dimethylphenyl)-1-octyl-4-phenylphosphacyclohexenes was 11% and the yield of 2,6-bis(2,4-dimethylphenyl)-4-phenylphosphacyclohexane was 0.7%. The compounds could be confirmed by GC-MS analysis and $^{31}$P-NMR spectroscopy.

Example 7

Preparation of a rhodium/2,6-bis(2,4-dimethylphenyl)-1-cyclohexyl-4-phenylphosphacyclohexane Solution 0.10 g (0.39 mmol) of dicarbonylrhodium acetylacetonate, 1.5 g (3.9 mmol) of 2,6-bis(2,4-dimethylphenyl)-4-phenylphosphabenzene and 10 g (122 mmol) of cyclohexene were dissolved in 20 g of toluene under nitrogen in a Schlenk tube. The resulting solution was transferred to a 100 ml autoclave which had been flushed with hydrogen. A pressure of 5 bar was then set by means of hydrogen. While stirring vigorously with a sparging stirrer, the reaction mixture was heated to 160° C. The hydrogen pressure in the autoclave was increased to 80 bar. The reaction mixture was then stirred at 160° C. for 24 hours. During the reaction, the pressure in the reactor was maintained by introduction of further hydrogen via a pressure regulator. After cooling to room temperature, the autoclave was depressurized to atmospheric pressure and another 10 g (122 mmol) of cyclohexene were added to the reaction. The reaction was continued as described above at 160° C. and 20 bar hydrogen pressure for a further 24 hours. After cooling to room temperature, the autoclave was depressurized to atmospheric pressure and another 10 g (122 mmol) of cyclohexene and 0.05 g (0.19 mmol) of dicarbonylrhodium acetylacetonate were added to the reaction. The reaction was continued as described above at 160° C. and 20 bar hydrogen pressure for a further 24 hours. GC analysis (NP detector) indicates a phosphabenzene conversion of 72%. The yield of 2,6-bis(2,4-dimethylphenyl)-1-cyclohexyl-4-phenylphosphacyclohexane was 29%, the yield of 2,6-bis(2,4-dimethylphenyl)-4-phenylphosphacyclohexane was 20% and the yield of 2,6-bis(2,4-dimethylphenyl)-4-phenylphosphacyclohexenes was 13%. The compounds could be confirmed by GC-MS analysis and $^{31}$P-NMR spectroscopy.

Example 8

Preparation of a rhodium/2,6-bis(2,4-dimethylphenyl)-1-octyl-4-phenylphosphacyclohexane Solution 0.15 g (0.58 mmol) of dicarbonylrhodium acetylacetonate, 1.5 g (3.9 mmol) of 2,6-bis(2,4- dimethylphenyl)-4-phenylphosphabenzene and 10 g (89 mmol) of 1-octene were dissolved in 20 g of toluene under nitrogen in a Schlenk tube. The resulting solution was transferred to a 100 ml autoclave which had been flushed with hydrogen. The autoclave was pressurized with 5 bar of hydrogen. While stirring vigorously with a sparging stirrer, the reaction mixture was heated to 150° C. The hydrogen pressure in the autoclave was increased to 80 bar. The reaction mixture was then stirred at 150° C. for 72 hours. During the reaction, the pressure in the reactor was maintained by introduction of further hydrogen via a pressure regulator. After cooling to room temperature, the autoclave was depressurized to atmospheric pressure. GC analysis (NP detector) of the reaction solution indicates a phosphabenzene conversion of 97%. The yield of 2,6-bis(2,4-dimethylphenyl)-1-octyl-4-phenylphosphacyclohexane was 53%, the yield of 2,6-bis(2,4-dimethylphenyl)-1-octyl-4-phenylphosphacyclohexenes was 40% and the yield of 2,6-bis(2,4-dimethylphenyl)-4-phenylphosphacyclohexane was 1%. The solution was admixed with another 10 g (89 mmol) of 1-octene. The autoclave was pressurized with 5 bar of $CO/H_2$ (1:1) at room temperature. While stirring vigorously with a sparging stirrer, the reaction mixture was heated to 180°C. The $CO/H_2$ (1:1) pressure in the autoclave was increased to 80 bar. The reaction mixture was then stirred at 180° C. for 24 hours. During the reaction, the pressure in the reactor was maintained by introduction of further $CO/H_2$ (1:1) via a pressure regulator. After the reaction time, the autoclave was cooled, vented and emptied. The solution obtained was completely evaporated in a high vacuum and the residue which remained was taken up in 100 g of toluene. Analysis of the solution indicated a rhodium content of 510 ppm and a phosphorus content of 1 200 ppm (P/Rh molar ratio=8). GC analysis (NP detector) indicates a phosphabenzene conversion of 99%. The yield of 2,6-bis(2,4-dimethylphenyl)-1-octyl-4-phenylphosphacyclohexane was 51% and the yield of 2,6-bis(2,4-dimethylphenyl)-1-octyl-4-phenylphosphacyclohexenes was 42%. The compounds could be confirmed by GC-MS analysis and $^{31}P$-NMR spectroscopy. 2,6-Bis(2,4-dimethylphenyl)-4-phenylphosphacyclohexane could not be detected.

Example 9

Preparation of a rhodium/1-octyl-2,4,6-triphenylphosphacyclo-hexane Solution 0.15 g (0.58 mmol) of dicarbonylrhodium acetylacetonate, 1.5 g (4.6 mmol) of 2,4,6-triphenylphosphabenzene and 10 g (89 mmol) of 1-octene were dissolved in 20 g of toluene under nitrogen in a Schlenk tube. The resulting solution was transferred to a 100 ml autoclave which had been flushed with hydrogen. The autoclave was pressurized with 5 bar of hydrogen. While stirring vigorously with a sparging stirrer, the reaction mixture was heated to 150° C. The hydrogen pressure in the autoclave was increased to 80 bar. The reaction mixture was then stirred at 150° C. for 72 hours. During the reaction, the pressure in the reactor was maintained by introduction of further hydrogen via a pressure regulator. After cooling to room temperature, the autoclave was depressurized to atmospheric pressure. GC analysis (NP detector) of the reaction solution indicates a phosphabenzene conversion of 98%. The yield of 1-octyl-2,4,6-triphenylphosphacyclohexane was 93%, the yield of 2,4,6-triphenylphosphacyclohexenes was 0.2% and the yield of 2,4,6-triphenylphosphacyclohexane was 0.1%. The solution was admixed with another 5 g (45 mmol) of 1-octene. The autoclave was pressurized with 5 bar of $CO/H_2$ (1:1) at room temperature. While stirring vigorously with a sparging stirrer, the reaction mixture was heated to 100° C. The $CO/H_2$ (1:1) pressure in the autoclave was increased to 20 bar. The reaction mixture was then stirred at 100° C. for 12 hours. During the reaction, the pressure in the reactor was maintained by introduction of further $CO/H_2$ (1:1) via a pressure regulator. After the reaction time, the autoclave was cooled, vented and emptied. The solution obtained was evaporated completely in a high vacuum and the residue which remained was taken up in 100 g of toluene. Analysis of the solution indicated a rhodium content of 720 ppm and a phosphorus content of 1 500 ppm (P/Rh molar ratio=7). GC analysis (NP detector) indicates a phosphabenzene conversion of 98%. The yield of 1-octyl-2,4,6-triphenylphosphacyclohexane was 95%. The compounds could be confirmed by GC-MS analysis and $^{31}P$-NMR spectroscopy. 2,4,6-Triphenylphosphacyclohexane and 2,4,6-triphenylphosphacyclohexenes could not be detected.

Example 10

Preparation of a rhodium/3-benzyl-1-octyl-2,4,6-triphenylphosphacyclohexane Solution 0.27 g (1.05 mmol) of dicarbonylrhodium acetylacetonate, 3.0 g (7.2 mmol) of 3-benzyl-2,4,6-triphenylphosphabenzene and 10 g (89 mmol) of 1-octene were dissolved in 10 g of toluene under nitrogen in a Schlenk tube. The resulting solution was transferred to a 100 ml autoclave which had been flushed with hydrogen. The autoclave was pressurized with 5 bar of hydrogen. While stirring vigorously with a sparging stirrer, the reaction mixture was heated to 160° C. The hydrogen pressure in the autoclave was increased to 80 bar. The reaction mixture was then stirred at 160° C. for 72 hours. During the reaction, the pressure in the reactor was maintained by introduction of further hydrogen via a pressure regulator. After cooling to room temperature, the autoclave was depressurized to atmospheric pressure. GC analysis (NP detector) of the reaction solution indicates a phosphabenzene conversion of 96%. The yield of 3-benzyl-1-octyl-2,4,6-triphenylphosphacyclohexane was 86% and the yield of 3-benzyl-1-octyl-2,4,6-triphenylphosphacyclohexenes was 8%. The solution was admixed with another 5 g (45 mmol) of 1-octene. The autoclave was pressurized with 5 bar of $CO/H_2$ (1:1) at room temperature. While stirring vigorously with a sparging stirrer, the reaction mixture was heated to 100° C. The $CO/H_2$ (1:1) pressure in the autoclave was increased to 20 bar. The reaction mixture was then stirred at 100° C. for 24 hours. During the reaction, the pressure in the reactor was maintained by introduction of further $CO/H_2$ (1:1) via a pressure regulator. After the reaction time, the autoclave was cooled, vented and emptied. The solution obtained was evaporated completely in a high vacuum and the residue which remained was taken up in 50 g of toluene. Analysis of the solution indicated a rhodium content of 1 400 ppm and a phosphorus content of 3 000 ppm (P/Rh molar ratio=7). GC analysis (NP detector) indicates a phosphabenzene conversion of 96%. The yield of 3-benzyl-1-octyl-2,4,6-triphenylphosphacyclohexane was 80% and the yield of 3-benzyl-1-octyl-2,4,6-triphenylphosphacyclohexenes was 10%. The compounds could be confirmed by GC-MS analysis and $^{31}P$-NMR spectroscopy. 3-Benzyl-2,4,6-triphenylphosphacyclohexane and 3-benzyl-2,4,6-triphenylphosphacyclohexenes could not be detected.

Example 11

Preparation of a rhodium/1-octyl-2,3,5,6-tetraphenylphosphacyclohexane Solution 0.27 g (1.05 mmol) of dicarbonylrhodium acetylacetonate, 3.0 g (7.5 mmol) of 2,3,5,6- tetraphenylphosphabenzene and 10 g (89 mmol) of 1-octene were dissolved in 10 g of toluene under nitrogen in a Schlenk tube. The resulting solution was transferred to a 100 ml autoclave which had been flushed with hydrogen. The autoclave was pressurized with 5 bar of hydrogen. While stirring vigorously with a sparging stirrer, the reaction mixture was heated to 160° C. The hydrogen pressure in the autoclave was increased to 80 bar. The reaction mixture was then stirred at 160° C. for 72 hours. During the reaction, the pressure in the reactor was maintained by introduction of further hydrogen via a pressure regulator. After the reaction time, the autoclave was cooled, vented and emptied. The solution obtained was evaporated completely in a high vacuum and the residue which remained was taken up in 50 g of toluene. Analysis of the solution indicated a rhodium content of 285 ppm and a phosphorus content of 590 ppm (P/Rh molar ratio=7). GC analysis (NP detector) of the reaction solution indicates a phosphabenzene conversion of 100%. The yield of 1-octyl-2,3,5,6-tetraphenylphosphacyclohexane was 92% and the yield of 1-octyl-2,3,5,6-tetraphenylphosphacyclohexenes was 3%. The compounds could be confirmed by GC-MS analysis and $^{31}$P-NMR spectroscopy. 2,3,5,6-Tetraphenylphosphacyclohexane and 2,3,5,6-tetraphenylphosphacyclohexenes could not be detected.

General Experimental Procedure for Batchwise Hydroformylation Experiments

Variant A:

Catalyst or catalyst solution and solvent were mixed under nitrogen in a Schlenk tube. The resulting solution was transferred to a 70 ml or 100 ml autoclave which had been flushed with $CO/H_2$ (1:1). The autoclave was pressurized with 2–5 bar of $CO/H_2$ (1:1) at room temperature. While stirring vigorously with a sparging stirrer, the reaction mixture was heated to the desired temperature over a period of 30 minutes. The olefin used was then introduced into the autoclave via a lock by means of $CO/H_2$ pressure. The desired reaction pressure was then set immediately by means of $CO/H_2$ (1:1). During the reaction, the pressure in the reactor was maintained by introduction of further $CO/H_2$ (1:1) via a pressure regulator. After the reaction time, the autoclave was cooled, vented and emptied. Analysis of the reaction mixture was carried out by means of GC using correction factors.

Variant B:

Catalyst or catalyst solution and solvent were mixed under nitrogen in a Schlenk tube. The resulting solution was transferred to a 70 ml or 100 ml autoclave which had been flushed with $CO/H_2$ (1:1). The autoclave was pressurized with 3–5 bar of $CO/H_2$ (1:1) at room temperature. While stirring vigorously with a sparging stirrer, the reaction mixture was heated to the reaction temperature over a period of 30 minutes. After preactivation of the catalyst, the autoclave was cooled and vented. The olefin used was then introduced into the autoclave via a lock by means of $CO/H_2$ pressure. The reaction mixture was once again heated to the desired temperature over a period of 30 minutes. The desired reaction pressure was then set immediately by means of $CO/H_2$ (1:1). During the reaction, the pressure in the reactor was maintained by introduction of further $CO/H_2$ (1:1) via a pressure regulator. After the reaction time, the autoclave was cooled, vented and emptied. Analysis of the reaction mixture was carried out by means of GC using correction factors.

Example 12

5 Low-Pressure Hydroformylation of 1-octene

Use of 15.8 g of catalyst solution from Example 1, 25.4 g (226 mmol) of 1-octene (purity: 95%, remainder: n-octenes having an internal double bond) and 9.2 g of toluene in the general experimental procedure (variant A) at 90° C., 10 bar of $CO/H_2$ for 4 hours gave a 1-octene conversion of 100%. The yield of nonanals was 97%, the selectivity to n-nonanal (proportion of n product) was 61% and the selectivity to n-nonanal and 2-methyloctanal (proportion of α products) was 96%.

Example 13

Low-Pressure Hydroformylation of 1-octene

Use of 8.8 g of catalyst solution from Example 2, 25.4 g (226 mmol) of 1-octene (purity: 95%, remainder: n-octenes having an internal double bond) and 16.2 g of toluene in the general experimental procedure (variant A) at 160° C., 10 bar of $CO/H_2$ for 4 hours gave a 1-octene conversion of 98%. The yield of nonanals was 30%, the selectivity to n-nonanal (proportion of n product) was 48% and the selectivity to n-nonanal and 2-methyloctanal (proportion of α products) was 83%. The yield of nonanols was 1%.

Example 14

Low-Pressure Hydroformylation of 1-octene

Use of 8.8 g of catalyst solution from Example 2, 25.9 g (231 mmol) of 1-octene (purity: 95%, remainder: n-octenes having an internal double bond) and 16.2 g of toluene in the general experimental procedure (variant A) at 90°C., 10 bar of $CO/H_2$ for 4 hours gave a 1-octene conversion of 100%. The yield of nonanals was 92%, the selectivity to n-nonanal (proportion of n product) was 65% and the selectivity to n-nonanal and 2-methyloctanal (proportion of α products) was 99%.

Example 15

Low-Pressure Hydroformylation of 1-octene
(Recycle)

Hydroformylation products and toluene in the reaction mixture from Example 14 were distilled off at 100° C. under reduced pressure. The residue which remained was dissolved in 25.0 g of toluene in the absence of air. The resulting solution was transferred to a 100 ml autoclave which had been flushed with $CO/H_2$ (1:1). The autoclave was pressurized cold with 5 bar of $CO/H_2$ (1:1). While stirring vigorously with a sparging stirrer, the reaction mixture was heated to 90° C. over a period of 30 minutes. 25.3 g (225 mmol) of 1-octene were then introduced into the autoclave via a lock by means of $CO/H_2$ pressure. A reaction pressure of 10 bar was then set immediately by means of $CO/H_2$ (1:1). During the reaction, the pressure in the reactor was maintained by introduction of further $CO/H_2$ (1:1) via a pressure regulator. After a reaction time of 4 hours, the autoclave was cooled, vented and emptied. An analysis was carried out by means of GC using correction factors. The conversion of 1-octene was 98%, the yield of nonanals was 93%, the selectivity to n-nonanal (proportion of n product) was 65% and the selectivity to n-nonanal and 2-methyloctanal (proportion of α products) was 99%.

Example 16

Low-Pressure Hydroformylation of 2-octene

Use of 9.2 g of catalyst solution from Example 1, 15.2 g (135 mmol) of 2-octene (cis:trans ratio=80:20) and 5.4 g of toluene in the general experimental procedure (variant A) at 160° C., 10 bar of $CO/H_2$ for 4 hours gave a 2-octene conversion of 93%. The yield of nonanals was 64%, the selectivity to n-nonanal (proportion of n product) was 35% and the selectivity to n-nonanal and 2-methyloctanal (proportion of α products) was 72%. The yield of nonanols was 14%, the selectivity to n-nonanol (proportion of n product) was 39% and the selectivity to n-nonanol and 2-methyloctanol (proportion of α products) was 72%.

Example 17

Intermediate-Pressure Hydroformylation of 2-octene

Use of 15.8 g of catalyst solution from Example 1, 25.8 g (230 mmol) of 2-octene (cis:trans ratio=80:20) and 9.2 g of toluene in the general experimental procedure (variant A) at 160° C., 60 bar of $CO/H_2$ for 30 minutes gave a 2-octene conversion of 100%. The yield of nonanals was 95%, the selectivity to n-nonanal (proportion of n product) was 24% and the selectivity to n-nonanal and 2-methyloctanal (proportion of α products) was 63%. The yield of nonanols was 4%, the selectivity to n-nonanol (proportion of n product) was 25% and the selectivity to n-nonanol and 2-methyloctanol (proportion of α products) was 71%.

Comparative Example 1

Intermediate-Pressure Hydroformylation of 2-octene

Use of 7.6 mg (0.029 mmol) of dicarbonylrhodium acetylacetonate, 0.155 g (0.59 mmol) of triphenylphosphine, 25.2 g (225 mmol) of 2-octene (cis:trans ratio=75:24) and 25.0 g of toluene in the general experimental procedure (variant A) at 160° C., 60 bar of $CO/H_2$ for 30 minutes gave a 2-octene conversion of 53%. The yield of nonanals was 37%, the selectivity to n-nonanal (proportion of n product) was 18% and the selectivity to n-nonanal and 2-methyloctanal (proportion of α products) was 79%. The yield of nonanols was 0%.

Example 18

Intermediate-Pressure Hydroformylation of Isobutene 4.0 g of catalyst solution from Example 1 were evaporated to dryness at about 80° C. in an oil pump vacuum. Use of the catalyst residue which remained, 5.7 g (102 mmol) of isobutene and 6.0 g of toluene in the general experimental procedure (variant B) at 160° C. and a total pressure of 40 bar (autogenous pressure of the olefin and $CO/H_2$) for 4 hours gave an isobutene conversion of 84%. The yield of 3-methylbutanal was 60% and the yield of 3-methylbutanol was 21%.

Comparative Example 2

Intermediate-Pressure Hydroformylation of Isobutene

Use of 2.1 mg (0.008 mmol) of dicarbonylrhodium acetylacetonate, 37.7 mg (0.144 mmol) of triphenylphosphine, 5.0 g (89 mmol) of isobutene and 6.0 g of toluene in the general experimental procedure (variant B) at 160° C. and a total pressure of 40 bar (autogeneous pressure of the olefin and $CO/H_2$) for 4 hours gave an isobutene conversion of 12%. The yield of 3-methylbutanal was 11% and the yield of 3-methylbutanol was 0%.

Example 19

Intermediate-Pressure Hydroformylation of Butene Dimer 15.8 g of catalyst solution from Example 1 were evaporated to dryness at about 80° C. in an oil pump vacuum. Use of the catalyst residue which remained, 25.8 g (230 mmol) of butene dimer (obtained by nickel-catalyzed dimerization of n-butenes, degree of branching=1.06) and 25.0 g of Texanol® in the general experimental procedure (variant A) at 160° C. and 60 bar of $CO/H_2$ gave the results shown in Table 1.

Example 20

Intermediate-Pressure Hydroformylation of Butene Dimer 16.0 g of catalyst solution from Example 1 were evaporated to dryness at about 80° C. in an oil pump vacuum. Use of the catalyst residue which remained, 24.7 g (220 mmol) of butene dimer (obtained by nickel-catalyzed dimerization of n-butenes, degree of branching=1.06) and 24.7 g of Texanol® in the general experimental procedure (variant A) at 140° C. and 60 bar of $CO/H_2$ gave the results shown in Table 1.

Example 21

Intermediate-Pressure Hydroformylation of Butene Dimer 16.0 g of catalyst solution from Example 1 were evaporated to dryness at about 80° C. in an oil pump vacuum. Use of the catalyst residue which remained, 21.6 g (192 mmol) of butene dimer (obtained by nickel-catalyzed dimerization of n-butenes, degree of branching=1.06) and 24.8 g of Texanol® in the general experimental procedure (variant A) at 120° C. and 60 bar of $CO/H_2$ gave the results shown in Table 1.

Example 22

Low-Pressure Hydroformylation of Butene Dimer 16.0 g of catalyst solution from Example 1 were evaporated to dryness at about 80° C. in an oil pump vacuum. Use of the catalyst residue which remained, 24.4 g (217 mmol) of butene dimer (obtained by nickel-catalyzed dimerization of n-butenes, degree of branching=1.06) and 24.8 g of Texanol® in the general experimental procedure (variant A) at 160° C. and 20 bar of $CO/H_2$ gave the results shown in Table 1.

The following comparative examples using triphenylphosphine which is not according to the present invention and bulky trialkylphosphines which are not according to the present invention as cocatalysts display a significantly lower activity, especially in the hydroformylation of internal branched olefins, than the phosphacyclohexane cocatalysts used according to the present invention:

Comparative Example 3

Intermediate-Pressure Hydroformylation of Butene Dimer

Use of 7.5 mg (0.029 mmol) of dicarbonylrhodium acetylacetonate, 0.157 g (0.60 mmol) of triphenylphosphine, 25.1 g (224 mmol) of butene dimer (obtained by nickel-catalyzed dimerization of n-butenes, degree of branching=1.06) and 25.0 g of Texanol® in the general experimental procedure (Variant A) at 160° C. and 60 bar of $CO/H_2$ gave the results shown in Table 2.

Comparative Example 4

Intermediate-Pressure Hydroformylation of Butene Dimer

Use of 7.8 mg of dicarbonylrhodium acetylacetonate (0.030 mmol), 83.0 mg (0.296 mmol) of tricyclohexylphosphine, 25.0 g (223 mmol) of butene dimer (obtained by nickel-catalyzed dimerization of n-butenes, degree of branching=1.06) and 25.0 g of Texanol® in the general experimental procedure (Variant A) at 160° C. and 60 bar of $CO/H_2$ gave the results shown in Table 2.

Comparative Example 5

Intermediate-Pressure Hydroformylation of Butene Dimer

Use of 8.1 mg of dicarbonylrhodium acetylacetonate (0.031 mmol), 42.9 mg (0.246 mmol) of n-butyldi-n-propylphosphine, 24.6 g (219 mmol) of butene dimer (obtained by nickel-catalyzed dimerization of n-butenes, degree of branching=1.06) and 24.7 g of Texanol® in the general experimental procedure (Variant A) at 160° C. and 60 bar of $CO/H_2$ gave the results shown in Table 2.

Comparative Example 6

Intermediate-Pressure Hydroformylation of Butene Dimer

Use of 8.2 mg of dicarbonylrhodium acetylacetonate (0.032 mmol), 46.0 mg (0.227 mmol) of tri-tert-butylphosphine, 24.6 g (219 mmol) of butene dimer (obtained by nickel-catalyzed dimerization of n-butenes, degree of branching=1.06) and 24.7 g of Texanol® in the general experimental procedure (Variant A) at 160° C. and 60 bar of $CO/H_2$ gave the results shown in Table 2.

Comparative Example 7

Intermediate-Pressure Hydroformylation of Butene Dimer

Use of 7.8 mg of dicarbonylrhodium acetylacetonate (0.030 mmol), 69.2 mg (0.223 mmol) of 9-dodecyl-9-phosphabicyclo[3.3.1]nonane, 26.8 g (239 mmol) of butene dimer (obtained by nickel-catalyzed dimerization of n-butenes, degree of branching=1.06) and 25.0 g of Texanol® in the general experimental procedure (variant A) at 160° C. and 60 bar of $CO/H_2$ gave the results shown in Table 2.

Example 23

Intermediate-pressure hydroformylation of 2-octene

Use of 4.3 g of catalyst solution from Example 6, 25.4 g (226 mmol) of 2-octene (cis:trans ratio=80:20) and 20.7 g of toluene in the general experimental procedure (variant A) at 160° C., 60 bar of $CO/H_2$ for 4 hours gave a 2-octene conversion of 100%. The yield of nonanals was 98% and the selectivity to n-nonanal (proportion of n product) was 4%. The selectivity to n-nonanal and 2-methyloctanal (proportion of α products) was 57%.

Example 24

Intermediate-Pressure Hydroformylation of Butene Dimer 8.8 g of catalyst solution from Example 2 were evaporated to dryness at about 80° C. in an oil pump vacuum. Use of the catalyst residue which remained, 25.6 g (228 mmol) of butene dimer (obtained by nickel-catalyzed dimerization of n-butenes, degree of branching=1.06) and 25.0 g of Texanol® in the general experimental procedure (variant A) at 160° C. and 60 bar of $CO/H_2$ gave a conversion of butene dimer of 71% after 1 hour and 94% after 4 hours. The yield of nonanals was 65% after 1 hour and 75% after 4 hours. The yield of nonanols was 3% after 1 hour and 15% after 4 hours.

Example 25

Intermediate-Pressure Hydroformylation of 1-octene

Use of 5.9 g of catalyst solution from Example 8, 25.1 g (224 mmol) of 1-octene (purity: 95%, remainder: n-octenes having an internal double bond) and 19.1 g of toluene in the general experimental procedure (variant A) at 100° C., 60 bar of $CO/H_2$ for 2 hours gave a 1-octene conversion of 100%. The yield of nonanals was 99%, the selectivity to n-nonanal (proportion of n product) was 62% and the selectivity to n-nonanal and 2-methyloctanal (proportion of α products) was 96%.

Example 26

Intermediate-Pressure Hydroformylation of Butene Dimer 6.0 g of catalyst solution from Example 8 were evaporated to dryness at about 100° C. in an oil pump vacuum. Use of the catalyst residue which remained, 24.0 g (214 mmol) of butene dimer (obtained by nickel-catalyzed dimerization of n-butenes, degree of branching=1.06) and 25.0 g of Texanol® in the general experimental procedure (variant A) at 160° C. and 60 bar of $CO/H_2$ gave a conversion of butene dimer of 89% after 1 hour and 97% after 4 hours. The yield of nonanals was 78% after 1 hour and 61% after 4 hours. The yield of nonanols was 8% after 1 hour and 28% after 4 hours.

Example 27

Intermediate-Pressure Hydroformylation of Butene Dimer 6.0 g of catalyst solution from Example 8 were evaporated to dryness at about 100° C. in an oil pump vacuum. Use of the catalyst residue which remained, 24.0 g (214 mmol) of butene dimer (obtained by nickel-catalyzed dimerization of n-butenes, degree of branching=1.06) and 23.8 g of Texanol® in the general experimental procedure (variant A) at 160° C., 60 bar of $CO/H_2$ for 24 hours gave a conversion of butene dimer of 97%. The yield of nonanals was 30% and the yield of nonanols was 45%.

Example 28

Intermediate-Pressure Hydroformylation of Butene Dimer (Recycle)

Hydroformylation products in the reaction mixture from Example 27 were distilled off at 100° C. under reduced pressure. This left a clear, dark yellow solution comprising active catalyst, Texanol® and high boilers intrinsic to the reaction. 25 g of Texanol® were added thereto in the absence of air. The resulting solution was transferred to a 100 ml autoclave which had been flushed with $CO/H_2$ (1:1). The autoclave was pressurized cold with 5 bar of $CO/H_2$ (1:1). While stirring vigorously with a sparging stirrer, the reaction mixture was heated to 160° C. over a period of 30 minutes. 24.0 g (214 mmol) of butene dimer (obtained by nickel-catalyzed dimerization of n-butenes, degree of branching=1.06) were then introduced into the autoclave via a lock by means of $CO/H_2$ pressure. A reaction pressure of 60 bar was then set immediately by means of $CO/H_2$ (1:1). During the reaction, the pressure in the reactor was maintained by introduction of further $CO/H_2$ (1:1) via a pressure regulator. After the reaction time of 4 hours, the autoclave was cooled, vented and emptied. An analysis was carried out by means of GC using correction factors. The conversion of butene dimer was 77% after 1 hour and 96% after 4 hours. The yield of nonanals was 60% after 1 hour and 60% after 4 hours. The yield of nonanols was 19% after 1 hour and 32% after 4 hours.

Example 29

Intermediate-Pressure Hydroformylation of Butene Dimer 15.0 g of catalyst solution from Example 5 were evaporated to dryness at about 80° C. in an oil pump vacuum. Use of the catalyst residue which remained, 25.4 g (226 mmol) of butene dimer (obtained by nickel-catalyzed dimerization of n-butenes, degree of branching=1.06) and 25.0 g of Texanol® in the general experimental procedure (variant A) at 160° C. and 60 bar of $CO/H_2$ gave a conversion of butene dimer of 52% after 1 hour and 82% after 4 hours. The yield of nonanals was 48% after 1 hour and 78% after 4 hours. The yield of nonanols was 3% after 1 hour and 5% after 4 hours.

Example 30

Intermediate-Pressure Hydroformylation of Butene Dimer 2.8 g of catalyst solution from Example 5 were evaporated to dryness at about 80° C. in an oil pump vacuum. Use of the catalyst residue which remained, 7.4 mg (0.029 mmol) of dicarbonylrhodium acetylacetonate, 25.2 g (225 mmol) of butene dimer (obtained by nickel-catalyzed dimerization of n-butenes, degree of branching 1.06) and 25.0 g of Texanol® in the general experimental procedure (variant A) at 160° C. and 60 bar of $CO/H_2$ gave a conversion of butene dimer of 77% after 1 hour and 87% after 4 hours. The yield of nonanals was 58% after 1 hour and 44% after 4 hours. The yield of nonanols was 15% after 1 hour and 29% after 4 hours.

Example 31

Intermediate-Pressure Hydroformylation of Butene Dimer 4.2 g of catalyst solution from Example 9 were evaporated to dryness at about 80° C. in an oil pump vacuum. Use of the catalyst residue which remained, 23.7 g (225 mmol) of butene dimer (obtained by nickel-catalyzed dimerization of n-butenes, degree of branching=1.06) and 25.0 g of Texanol® in the general experimental procedure (variant A) at 160° C. and 60 bar of $CO/H_2$ gave a conversion of butene dimer of 68% after 1 hour and 92% after 4 hours. The yield of nonanals was 65% after 1 hour and 78% after 4 hours. The yield of nonanols was 2% after 1 hour and 13% after 4 hours.

Example 32

Low-Pressure Hydroformylation of 1-octene

Use of 4.2 g of catalyst solution from Example 9, 25.6 g (226 mmol) of 1-octene (purity: 97%, remainder: n-octenes having an internal double bond) and 25.0 g of toluene in the general experimental procedure (variant A) at 90° C., 10 bar of $CO/H_2$ for 3 hours gave a 1-octene conversion of 100%. The yield of nonanals was 96%, the selectivity to n-nonanal (proportion of n product) was 62% and the selectivity to n-nonanal and 2-methyloctanal (proportion of α products) was 98%.

Example 33

Intermediate-Pressure Hydroformylation of Butene Dimer 4.2 g of catalyst solution from Example 11 were evaporated to dryness at about 80° C. in an oil pump vacuum. Use of the catalyst residue which remained, 23.8 g (212 mmol) of butene dimer (obtained by nickel-catalyzed dimerization of n-butenes, degree of branching=1.06) and 25.0 g of Texanol® in the general experimental procedure (variant A) at 160° C. and 60 bar of $CO/H_2$ gave a conversion of butene dimer of 54% after 1 hour and 83% after 4 hours. The yield of nonanals was 53% after 1 hour and 75% after 4 hours. The yield of nonanols was 1% after 1 hour and 7% after 4 hours.

Example 34

Low-Pressure Hydroformylation of 1-octene

Use of 7.8 mg (0.030 mmol) of dicarbonylrhodium acetylacetonate, 0.145 g (0.57 mmol) of 1-cyclohexyl-2,2,6,6-tetramethylphosphacyclohexan-4-one, 24.8 g (221 mmol) of 1-octene (purity: 95%, remainder: n-octenes having an internal double bond) and 24.8 g of toluene in the general experimental procedure (variant A) at 90° C., 10 bar of $CO/H_2$ for 4 hours gave a 1-octene conversion of 91%. The yield of nonanals was 84%, the selectivity to n-nonanal (proportion of n product) was 55% and the selectivity to n-nonanal and 2-methyloctanal (proportion of α products) was 100%.

Example 35

Intermediate-Pressure Hydroformylation of Butene Dimer

Use of 7.4 mg (0.029 mmol) of dicarbonylrhodium acetylacetonate, 0.080 g (0.31 mmol) of 1-cyclohexyl-2,2,6,6tetramethylphosphacyclohexan-4-one, 20.7 g (184 mmol) of butene dimer (obtained by nickel-catalyzed dimerization of n-butenes, degree of branching=1.06) and 24.7 g of Texanol® in the general experimental procedure (variant A) at 160° C., 60 bar of $CO/H_2$ for 4 hours gave a conversion of butene dimer of 72%. The yield of nonanals was 69% and the yield of nonanols was 3%.

Example 36

Low-Pressure Hydroformylation of 1-octene

Use of 7.4 mg (0.029 mmol) of dicarbonylrhodium acetylacetonate, 0.127 g (0.33 mmol) of 1-octyl-2,6-diphenylphosphacyclohexan-4-one, 25.0 g (223 mmol) of 1-octene (purity: 95%, remainder: n-octenes having an internal double bond) and 24.8 g of toluene in the general experimental procedure (variant A, but preactivation of the catalyst for 180 minutes) at 90° C., 10 bar of $CO/H_2$ for 4 hours gave a 1-octene conversion of 75%. The yield of nonanals was 71%, the selectivity to n-nonanal (proportion of n product) was 66% and the selectivity to n-nonanal and 2-methyloctanal (proportion of α products) was 100%.

Example 37

Intermediate-Pressure Hydroformylation of Butene Dimer

Use of 7.7 mg (0.030 mmol) of dicarbonylrhodium acetylacetonate, 0.112 g (0.29 mmol) of 1-octyl-2,6-diphenylphosphacyclohexan-4-one, 20.7 g (184 mmol) of butene dimer (obtained by nickel-catalyzed dimerization of n-butenes, degree of branching=1.06) and 24.7 g of Texanol® in the general experimental procedure (variant A) at 160° C., 60 bar of $CO/H_2$ for 4 hours gave a conversion of butene dimer of 79%. The yield of nonanals was 73% and the yield of nonanols was 4%.

Example 38

Low-pressure Hydroformylation of 1-octene

Use of 9.8 mg (0.038 mmol) of dicarbonylrhodium acetylacetonate, 0.162 g (0.65 mmol) of 1-phenyl-2,2,6,6- tetramethylphosphacyclohexan-4-one, 25.7 g (229 mmol) of 1-octene (purity: 95%, remainder: n-octenes having an internal double bond) and 25 g of toluene in the general experimental procedure (variant A) at 90° C., 10 bar of CO/H$_2$ for 4 hours gave a 1-octene conversion of 100%. The yield of nonanals was 97%, the selectivity to n-nonanal (proportion of n product) was 58% and the selectivity to n-nonanal and 2-methyloctanal (proportion of a products) was 95%.

Example 39

Continuous Low-Pressure Hydroformylation of Propene

The continuous low-pressure hydroformylation was carried out using a miniplant as shown in FIG. 1.

Synthesis gas and an olefin feed are fed into a pressure reactor. The output from the pressure reactor is conveyed firstly into a pressure separator and subsequently into a flash vessel. The liquid output from the flash vessel is then fed into a wiped film evaporator. In the wiped film evaporator, the product is obtained as distillate. Furthermore, a liquid catalyst-containing stream is taken from the wiped film evaporator and is recirculated to the reactor. A waste gas stream (released gas) is taken off at the top of the pressure separator and the flash vessel and is discharged.

Figure 2:
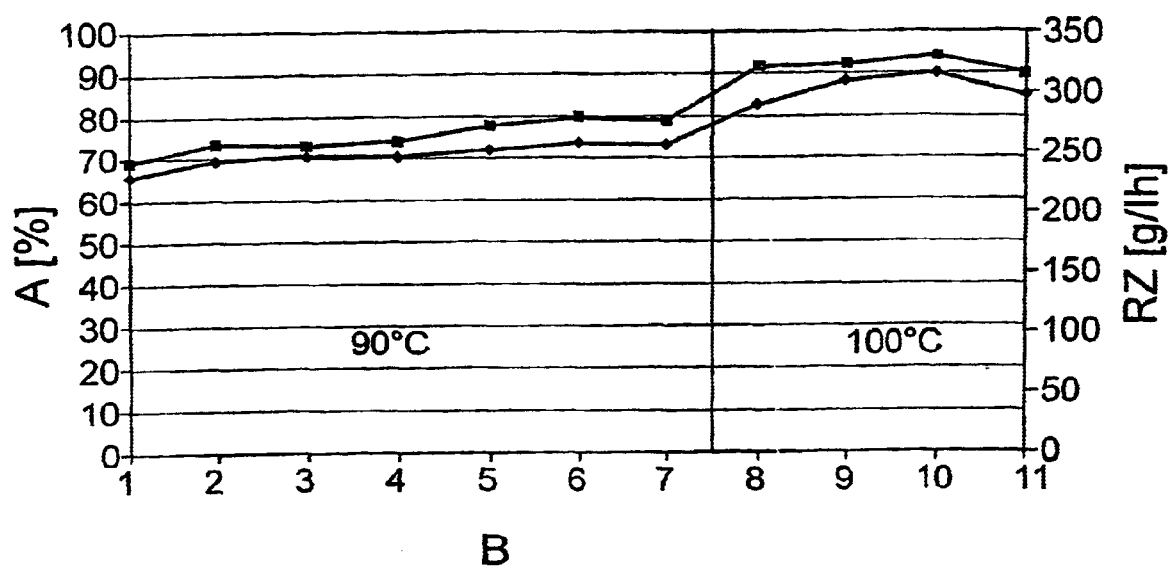

Propene was continuously hydroformylated in the miniplant using the catalyst system rhodium/2,6-bis(2,4-dimethylphenyl)-4-phenyl-1-propylphospacyclohexane. The cocatalyst was prepared in situ from 2,6-bis(2,4-dimethylphenyl)-4-phenylphosphabenzene by continuous operation of the rhodium-catalyzed hydroformylation as described below at a reactor temperature of 84–89° C. and a reactor pressure of 20 bar. 328 g/h of propene were hydroformylated in a reactor at an internal reactor temperature of 82–100° C. and a total pressure of 20 bar in the presence of 80–120 ppm of rhodium and 2,6-bis(2,4-dimethylphenyl)-4-phenyl-1-propylphospacyclohexane generated in situ as cocatalyst [P/Rh ratio=11 (mol:mol)] (the concentration figures are based on the amount of reaction mixture) and 1 kg of Texanol® as solvent. A CO/H$_2$ (1:1) gas mixture was fed to the reactor in such an amount that a constant waste gas flow via a pressure separator of about 120 standard 1/h resulted. The liquid output from the reactor was depressurized in a flash vessel and fractionated in a wiped film evaporator to give butyraldehyde distillate and catalyst-containing bottoms. The catalyst-containing product was returned continuously to the reactor. The conversions, selectivities and space-time yields achieved are shown in Table 3 and FIG. 2. In the figure, A is the aldehyde yield, B are the days on which the balance was carried out, and STY is the space-time yield. The solid squares denote the aldehyde yield, and the diamonds denote the space-time yield.

Table 3: conversions, selectivities and space-time yields in the continuous hydroformylation of propene (20 bar total pressure, L/Rh=11, about 100 ppm of Rh) without taking account of high boiler formation

| Temperature | [° C.] | 90 | 100 |
|---|---|---|---|
| Propene (conversion) | [%] | 75.4 | 92.4 |
| Butyraldehyde (selectivity) | [%] | 99.8 | 99.8 |
| Proportion of n-product (selectivity) | [%] | 58.7 | 58.2 |
| Propane (selectivity) | [%] | 0.1 | 0.1 |
| Butanols (selectivity) | [%] | 0.1 | 0.1 |
| Space-time yield | [g/l · h] | 247 | 304 |

Comparative Example 8

Continuous Low-Pressure Hydroformylation of Propene

Propene was hydroformylated in the miniplant described in Example 39 using the catalyst system rhodium/triphenylphosphine. 328 g/h of propene were hydroformylated in a reactor at an internal reactor temperature of 100° C. and a total pressure of 20 bar in the presence of 100–120 ppm of rhodium and 22 g of triphenylphosphine as cocatalyst [P/Rh ratio=20 (mol:mol)] (the concentrations are based on the amount of reaction mixture) and 1 kg of Texanol® as solvent. A CO/H$_2$ (1:1) gas mixture was fed to the reactor in such an amount that a constant waste gas flow via a pressure separator of about 120 standard 1/h resulted. The liquid output from the reactor was depressurized in a flash vessel and fractionated in a wiped film evaporator to give butyraldehyde distillate and catalyst-containing bottoms. The catalyst-containing product was returned continuously to the reactor. The conversions, selectivities and space-time yields achieved are shown in Table 4.

Table 4: conversions, selectivities and space-time yields in the continuous hydroformylation of propene (20 bar total pressure, L/Rh=20, about 100 ppm of Rh) without taking account of high boiler formation

| Temperature | [° C.] | 100 |
|---|---|---|
| Propene (conversion) | [%] | 71.4 |
| Butyraldehyde (selectivity) | [%] | 97.9 |
| Proportion of n-product (selectivity) | [%] | 68.8 |
| Propane (selectivity) | [%] | 0.8 |
| Butanols (selectivity) | [%] | 1.3 |
| Space-time yield | [g/l · h] | 231 |

TABLE 1

Hydroformylation of butene dimer (obtained by nickel-catalyzed dimerization of n-butenes, degree of branching = 1.06) using phosphacyclohexanes as cocatalysts

| Example | T [° C.] | p [bar] | Reaction time [h] | Butene dimer (conversion) [%] | Nonanals (yield) [%] | Nonanols (yield) [%][1/min] | TOF* (olefin) [1/h] |
|---|---|---|---|---|---|---|---|
| 19 | 160 | 60 | 1 | 89 | 78 | 8 | 6 350 |
|  |  |  | 4 | 97 | 61 | 28 |  |
| 20 | 140 | 60 | 1 | 66 | 65 | 1 | 4 920 |
|  |  |  | 4 | 91 | 86 | 5 |  |
| 21 | 120 | 60 | 1 | 47 | 47 | 0 | 3 720 |
|  |  |  | 4 | 68 | 67 | 1 |  |

TABLE 1-continued

Hydroformylation of butene dimer (obtained by nickel-catalyzed dimerization of n-butenes, degree of branching = 1.06) using phosphacyclohexanes as cocatalysts

| Example | T [° C.] | p [bar] | Reaction time [h] | Butene dimer (conversion) [%] | Nonanals (yield) [%] | Nonanols (yield) [%] | TOF* (olefin) [1/h] |
|---|---|---|---|---|---|---|---|
| 22 | 160 | 20 | 1 | 60 | 54 | 6 | 4 440 |
|  |  |  | 4 | 82 | 59 | 21 |  |
| 31 | 160 | 60 | 1 | 68 | 65 | 2 | 4 860 |
|  |  |  | 4 | 92 | 78 | 13 |  |

*TOF (turnover frequency) = product [mol]/(catalyst [mol] × time [h])

TABLE 2

Hydroformylation of butene dimer (obtained by nickel-catalyzed dimerization of n-butenes, degree of branching = 1.06) using triphenylphosphine and trialkylphosphines as cocatalysts

| Comparative example | T [° C.] | p [bar] | Reaction-time [h] | Butene dimer (conversion) [%] | Nonanals (yield) [%] | Nonanols (yield) [%] | TOF* (olefin) [1/h] |
|---|---|---|---|---|---|---|---|
| 3 | 160 | 60 | 1 | 4 | 3 | 0 | 292 |
|  |  |  | 4 | 9 | 4 | 0 |  |
| 4 | 160 | 60 | 1 | 51 | 50 | 1 | 3 780 |
|  |  |  | 4 | 70 | 66 | 5 |  |
| 5 | 160 | 60 | 1 | 58 | 57 | 1 | 4 020 |
|  |  |  | 4 | 79 | 73 | 6 |  |
| 6 | 160 | 60 | 1 | 63 | 57 | 7 | 4 320 |
|  |  |  | 4 | 91 | 58 | 33 |  |
| 7 | 160 | 60 | 1 | 52 | 47 | 0 | 4 080 |
|  |  |  | 4 | 71 | 68 | 3 |  |

*TOF (turnover frequency) = product [mol]/(catalyst [mol] × time [h])

Example 40

Preparation of a rhodium/2,4,6-tris(4-methylphenyl)-1-octylphosphacyclohexane Solution 0.05 g (0.19 mmol) of dicarbonylrhodium acetylacetonate, 0.5 g (1.4 mmol) of 2,4,6-tris(4-methylphenyl)phosphabenzene and 15 g (134 mmol) of 1-octene were dissolved in 10 g of toluene under nitrogen in a Schlenk tube. The resulting solution was transferred to a 100 ml autoclave which had been flushed with hydrogen. The autoclave was pressurized with 5 bar of hydrogen. While stirring vigorously with a sparging stirrer, the reaction mixture was heated to 160° C. The hydrogen pressure in the autoclave was increased to 80 bar. The reaction mixture was then stirred at 160° C. for 72 hours. During the reaction, the pressure in the reactor was maintained by introduction of further hydrogen via a pressure regulator. The reaction solution was cooled to room temperature and used further as such. Analysis of the solution indicated a rhodium content of 680 ppm and a phosphorus content of 1 500 ppm (P/Rh molar ratio=7). GC analysis (NP detector) indicates a phosphabenzene conversion of 97%. The yield of 2,4,6-tris(4-methylphenyl)-1-octylphosphacyclohexane was 97%. The product could additionally be confirmed by $^{31}$P-NMR spectroscopy.

Example 41

Preparation of a Rhodium/2,6-bis(4-tert-butylphenyl)-1-octyl-4-phenylphosphacyclohexane Solution 0.17 g (0.66 mmol) of dicarbonylrhodium acetylacetonate, 2.0 g (4.6 mmol) of 2,6-bis(4-tert-butylphenyl)-4-phenylphosphabenzene and 20 g (178 mmol) of 1-octene were dissolved in 10 g of toluene under nitrogen in a Schlenk tube. The resulting solution was transferred to a 100 ml autoclave which had been flushed with hydrogen. The autoclave was pressurized with 5 bar of hydrogen. While stirring vigorously with a sparging stirrer, the reaction mixture was heated to 160° C. The hydrogen pressure in the autoclave was increased to 80 bar. The reaction mixture was then stirred at 160° C. for 72 hours. During the reaction, the pressure in the reactor was maintained by introduction of further hydrogen via a pressure regulator. After cooling to room temperature, another 20 ml of 1-octene were added to complete the reaction. The reaction was continued as described above at 160° C. and 80 bar hydrogen pressure for a further 24 hours. The reaction solution was cooled to room temperature, evaporated to about one quarter of its original volume in a high vacuum and subsequently diluted with 20 ml of toluene. Analysis of the solution indicated a rhodium content of 2 100 ppm and a phosphorus content of 4 300 ppm (P/Rh molar ratio=7). GC analysis (NP detector) indicates a phosabenzene conversion of 95%. The yield of 2,6-bis(4-tert-butylphenyl)-1-octyl-4-phenylphosphacyclohexane was 95%. The product could additionally be confirmed by $^{31}$P-NMR spectroscopy.

Example 42

Preparation of a rhodium/2,6-bis(2,4-dimethylphenyl)-1-octyl-4-phenylphosphacyclohexane Solution 0.88 g (3.4 mmol) of dicarbonylrhodium acetylacetonate, 13 g (34 mmol) of 2,6-bis(2,4-dimethylphenyl)-4- phenylphosphabenzene and 85.8 g (765 mmol) of 1-octene were dissolved in 50 ml of xylene under nitrogen in a Schlenk tube. The resulting solution was transferred to a 300 ml autoclave which had been flushed with hydrogen. The autoclave was pressurized with 10 bar of hydrogen. While stirring vigorously with a sparging stirrer, the reaction mixture was heated to 160° C. The hydrogen pressure in the autoclave was increased to 80 bar. The reaction mixture was then stirred at 160° C. for 72 hours. During the reaction, the pressure in the reactor was maintained by introduction of further hydrogen via a pressure regulator. The reaction solution was cooled to room temperature and used further as such. Analysis of the solution indicated a rhodium content of 2 400 ppm and a phosphorus content of 7 200 ppm (P/Rh molar ratio=10). GC analysis (NP detector) indicates a phosphabenzene conversion of 97%. The yield of 2,6-bis(2,4-dimethylphenyl)-1-octyl-4-phenyl-phosphacyclohexanes and -hexenes was 95% and the yield of 2,6-bis(2,4-dimethylphenyl)-4-phenylphosphacyclohexane was 0.3%. The compounds could be confirmed by GC-MS analysis and $^{31}$P-NMR spectroscopy.

Exampe 43

Preparation of a rhodium/2,6-bis(2,4-dimethylphenyl)-1-octyl-4-phenylphosphacyclohexane Solution 0.90 g (3.5 mmol) of dicarbonylrhodium acetylacetonate, 10 g (26 mmol) of 2,6-bis(2,4-dimethylphenyl)-4-phenylphosphabenzene and 85.8 g (765 mmol) of 1-octene were dissolved in 50 ml of toluene under nitrogen in a Schlenk tube. The resulting solution was transferred to a 300 ml autoclave which had been flushed with hydrogen. The autoclave was pressurized with 10 bar of hydrogen. While stirring vigorously with a sparging stirrer, the reaction mixture was heated to 160° C. The hydrogen pressure in the autoclave was increased to 80 bar. The reaction mixture was then stirred at 160° C. for 72 hours. During the reaction, the pressure in the reactor was maintained by introduction of further hydrogen via a pressure regulator. After cooling to room temperature, the solution obtained was evaporated completely in a high vacuum and then taken up in 70 ml of toluene. Analysis of the solution indicated a rhodium content of 3 600 ppm and a phosphorus content of 8 400 ppm (P/Rh molar ratio=8). GC analysis (NP detector) indicates a phosphabenzene conversion of 96%. The yield of 2,6-bis(2,4-dimethylphenyl)-1-octyl-4-phenylphosphacyclohexane was 88%, the yield of 2,6-bis(2,4-dimethylphenyl)-1-octyl-4-phenylphosphacyclohexenes was 6% and the yield of 2,6-bis(2,4-dimethylphenyl)-4-phenylphosphacyclohexane was 0.2%. The compounds could be confirmed by GC-MS analysis and $^{31}$P-NMR spectroscopy.

Example 44

Preparation of a rhodium/4-phenyl-2,6-bis(2-naphthyl)-1-octylphosphacyclohexane Solution 0.26 g (1.0 mmol) of dicarbonylrhodium acetylacetonate, 3.0 g (7.1 mmol) of 4-phenyl-2,6-bis(2-naphthyl)phosphabenzene and 10 g (89 mmol) of 1-octene were dissolved in 10 g of toluene under nitrogen in a Schlenk tube. The resulting solution was transferred to a 100 ml autoclave which had been flushed with hydrogen. The autoclave was pressurized with 5 bar of hydrogen. While stirring vigorously with a sparging stirrer, the reaction mixture was heated to 160° C. The hydrogen pressure in the autoclave was increased to 80 bar. The reaction mixture was then stirred at 160° C. for 96 hours. During the reaction, the pressure in the reactor was maintained by introduction of further hydrogen via a pressure regulator. The reaction solution was cooled to room temperature and used further as such. Analysis of the solution indicated a rhodium content of 2 100 ppm and a phosphorus content of 4 300 ppm (P/Rh molar ratio=7). GC analysis (NP detector) indicates a phosphabenzene conversion of 90%. The yield of 4-phenyl-2,6-bis(2-naphthyl)-1-octylphosphacyclohexane was 89%. The product could additionally be confirmed by $^{31}$P-NMR spectroscopy.

Example 45

Preparation of a rhodium/2,6-bis(2-methylphenyl)-1-octyl-4-phenylphosphacyclohexane Solution 0.14 g (0.54 mmol) of dicarbonylrhodium acetylacetonate, 1.5 g (4.3 mmol) of 2,6-bis(2-methylphenyl)-4-phenylphosphabenzene and 10 g (89 mmol) of 1-octene were dissolved in 10 g of toluene under nitrogen in a Schlenk tube. The resulting solution was transferred to a 100 ml autoclave which had been flushed with hydrogen. The autoclave was pressurized with 5 bar of hydrogen. While stirring vigorously with a sparging stirrer, the reaction mixture was heated to 160° C. The hydrogen pressure in the autoclave was increased to 80 bar. The reaction mixture was then stirred at 160° C. for 72 hours. During the reaction, the pressure in the reactor was maintained by introduction of further hydrogen via a pressure regulator. After cooling to room temperature, another 10 g (89 mmol) of 1-octene were added to complete the reaction. The reaction was continued as described above at 160° C. and 80 bar hydrogen for a further 48 hours. After cooling to room temperature, the autoclave was depressurized to atmospheric pressure. GC analysis (NP detector) of the reaction solution indicates a phosphabenzene conversion of 99%. The yield of 2,6-bis(2-methylphenyl)-1-octyl-4-phenylphosphacyclohexane was 98%. The solution was admixed with another 5 g (45 mmol) of 1-octene. The autoclave was pressurized with 5 bar of CO/H$_2$ (1:1) at room temperature. While stirring vigorously with a sparging stirrer, the reaction mixture was heated to 100° C. The CO/H$_2$ (1:1) pressure in the autoclave was increased to 20 bar. The reaction mixture was then stirred at 100° C. for 12 hours. During the reaction, the pressure in the reactor was maintained by introduction of further CO/H$_2$ (1:1) via a pressure regulator. After the reaction time, the autoclave was cooled, depressurized and emptied. The solution obtained was evaporated completely in a high vacuum and the residue which remained was taken up in 30 ml of toluene. Analysis of the solution indicated a rhodium content of 710 ppm and a phosphorus content of 1 600 ppm (P/Rh molar ratio=7). GC analysis (NP detector) indicates a phosphabenzene conversion of 99%. The yield of 2,6-bis(2-methylphenyl)-1-octyl-4-phenylphosphacyclohexane was 96%. The product could additionally be confirmed by $^{31}$P-NMR spectroscopy.

Example 46

Preparation of a Rhodium/Phosphacyclohexane Solution of a Phosphacyclohexane of the Formula A

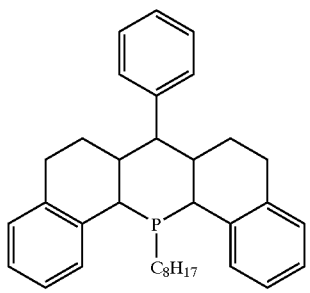

A 0.02 g (0.08 mmol) of dicarbonylrhodium acetylacetonate, 0.20 g (0.53 mmol) of 10-phenyl-1,2,7,8-dibenzo-3,4,5,6-tetrahydro-9-phosphaanthracene and 10 g (89 mmol) of 1-octene were dissolved in 10 g of toluene under nitrogen in a Schlenk tube. The resulting solution was transferred to a 300 ml autoclave which had been flushed with hydrogen. The autoclave was pressurized with 5 bar of hydrogen. While stirring vigorously with a sparging stirrer, the reaction mixture was heated to 160° C. The hydrogen pressure in the autoclave was increased to 80 bar. The reaction mixture was then stirred at 160° C. for 72 hours. During the reaction, the pressure in the reactor was maintained by introduction of further hydrogen via a pressure regulator. After the reaction time, the autoclave was cooled, depressurized and emptied. The solution obtained was evaporated completely in a high vacuum and the residue which remained was taken up in 10 ml of toluene. Analysis of the solution indicated a rhodium content of 165 ppm and a phosphorus content of 920 ppm (P/Rh molar ratio=19). GC analysis (NP detector) indicates a phosphabenzene conversion of 99%. The yield of the phosphacyclohexane of the formula A was 94%. The compound could be confirmed by GC-MS analysis and $^{31}$P-NMR spectroscopy.

Example 47

Preparation of 2,6-bis(2,4-dimethylphenyl)-1-octyl-4-phenylphosphacyclohexane 0.30 g (1.2 mmol) of dicarbonylrhodium acetylacetonate, 3.0 g (7.9 mmol) of 2,6-bis(2,4-dimethylphenyl)-4-phenylphosphabenzene and 10 g (89 mmol) of 1-octene were dissolved in 10 g of toluene under nitrogen in a Schlenk tube. The resulting solution was transferred to a 100 ml autoclave which had been flushed with hydrogen. The autoclave was pressurized with 5 bar of hydrogen. While stirring vigorously with a sparging stirrer, the reaction mixture was heated to 160° C. The hydrogen pressure in the autoclave was increased to 80 bar. The reaction mixture was then stirred at 160° C. for 96 hours. During the reaction, the pressure in the reactor was maintained by introduction of further hydrogen via a pressure regulator. After cooling to room temperature, another 10 g (89 mmol) of 1-octene were added to complete the reaction. The reaction was continued as described above at 160° C. and 80 bar hydrogen for a further 24 hours. After cooling to room temperature, the autoclave was depressurized to atmospheric pressure. The solution was admixed with another 5 g (45 mmol) of 1-octene. The autoclave was pressurized with 5 bar of CO/H$_2$ (1:1) at room temperature. While stirring vigorously with a sparging stirrer, the reaction mixture was heated to 100° C. The CO/H$_2$ (1:1) pressure in the autoclave was increased to 20 bar. The reaction mixture was then stirred at 100° C. for 12 hours. During the reaction, the pressure in the reactor was maintained by introduction of further CO/H$_2$ (1:1) via a pressure regulator. After the reaction time, the autoclave was cooled, depressurized and emptied.

20 g of the catalyst solution obtained were evaporated to dryness at about 80° C. in an oil pump vacuum. The residue which remained was subjected to a bulb tube distillation. At 270–280° C./0.07 mbar, 1.42 g of the product were obtained in the form of a yellow oil. The constitution of the product could be confirmed by GC analysis (NP detector), $^{31}$P-, $^1$H- and $^{13}$C-NMR spectroscopy. The distillate was taken up in 7 g of toluene. Analysis of the solution indicated a phosphorus content of 9 400 ppm.

Example 48

Preparation of 1-octyl-2,4,6-triphenylphosphacyclohexane 0.09 g (0.35 mmol) of dicarbonylrhodium acetylacetonate, 0.95 g (2.9 mmol) of 2,4,6-triphenylphosphabenzene and 10 g (89 mmol) of 1-octene were dissolved in 10 g of toluene under nitrogen in a Schlenk tube. The resulting solution was transferred to a 100 ml autoclave which had been flushed with hydrogen. The autoclave was pressurized with 5 bar of hydrogen. While stirring vigorously with a sparging stirrer, the reaction mixture was heated to 160° C. The hydrogen pressure in the autoclave was increased to 80 bar. The reaction mixture was then stirred at 160° C. for 96 hours. During the reaction, the pressure in the reactor was maintained by introduction of further hydrogen via a pressure regulator.

20 g of the catalyst solution obtained were evaporated to dryness at about 80° C. in an oil pump vacuum. The residue which remained was subjected to a bulb tube distillation. At 270–280° C./0.07 mbar, 0.45 g of the product was obtained in the form of a light-yellow oil which slowly solidified at room temperature. The constitution of the product could be confirmed by GC analysis (NP detector), 31P-, $^1$H- and $^{13}$C-NMR spectroscopy. The distillate was taken up in 7.25 g of toluene. Analysis of the solution indicated a phosphorus content of 4 100 ppm.

Example 49

Preparation of a rhodium/2,6-bis(2,5-dimethylphenyl)-1-octyl-4-phenylphosphacyclohexane Solution 0.045 g (0.17 mmol) of dicarbonylrhodium acetylacetonate, 0.57 g (1.5 mmol) of 2,6-bis(2,5-dimethylphenyl)-4-phenylphosphabenzene and 120 g (766 mmol) of 1-octene were dissolved in 50 ml of xylene under nitrogen in a Schlenk tube. The resulting solution was transferred to a 300 ml autoclave which had been flushed with hydrogen. The autoclave was pressurized with 10 bar of hydrogen. While stirring vigorously with a sparging stirrer, the reaction mixture was heated to 160° C. The hydrogen pressure in the autoclave was increased to 80 bar. The reaction mixture was then stirred at 160° C. for 72 hours. During the reaction, the pressure in the reactor was maintained by introduction of further hydrogen via a pressure regulator. The reaction solution was cooled to room temperature and evaporated to about 50 ml in an oil pump vacuum. Analysis of the solution gave a rhodium content of 480 ppm and a phosphorus content of 1 200 ppm (P/Rh molar ratio=8). GC analysis (NP detector) indicates a phosphabenzene conversion of 100%. The yield of 2,6-bis(2,5-dimethylphenyl)-1-octyl-4-phenylphosphacyclohexane was

Example 50

Preparation of a rhodium/2,6-bis(2,4-dimethylphenyl)-1-dodecyl-4-phenylphosphacyclohexane Solution 0.88 g (3.4 mmol) of dicarbonylrhodium acetylacetonate, 13 g (34 mmol) of 2,6-bis(2,4-dimethylphenyl)-4-phenylphosphabenzene and 91 g (541 mmol) of 1-dodecene were dissolved in 50 ml of xylene under nitrogen in a Schlenk tube. The resulting solution was transferred to a 300 ml autoclave which had been flushed with hydrogen. The autoclave was pressurized with 10 bar of hydrogen. While stirring vigorously with a sparging stirrer, the reaction mixture was heated to 160° C. The hydrogen pressure in the autoclave was increased to 80 bar. The reaction mixture was then stirred at 160° C. for 72 hours. During the reaction, the pressure in the reactor was maintained by introduction of further hydrogen via a pressure regulator. After cooling to room temperature, the autoclave was depressurized to atmospheric pressure, and the reaction solution was subsequently evaporated to about 40 ml in an oil pump vacuum with slight heating. To complete the reaction, the reaction solution was admixed with another 91 g (541 mmol) of 1-dodecene. The reaction was continued as described above at 160° C. and 80 bar of hydrogen pressure for a further 24 hours. The reaction solution was cooled to room temperature and used further as such. Analysis of the solution indicated a rhodium content of 2 500 ppm and a phosphorus content of 7 400 ppm (P/Rh molar ratio=8). GC analysis (NP detector) indicates a phosphabenzene conversion of 89%. The yield of 2,6-bis(2,4-dimethylphenyl)-1-dodecyl-4-phenylphosphacyclohexane was 85%. The compound could be confirmed by GC-MS analysis and $^{31}$P-NMR spectroscopy.

Example 51

Intermediate-Pressure Hydroformylation of Butene Dimer 4.4 g of catalyst solution from Example 40 were evaporated to dryness at about 80° C. in an oil pump vacuum. The use of the catalyst residue which remained, 24.8 g (221 mmol) of butene dimer (obtained by nickel-catalyzed dimerization of n-butenes, degree of branching=1.06) and 25.0 g of Texanol® in the general experimental procedure (variant A) at 140° C. and 80 bar of $CO/H_2$ gave a conversion of butene dimer of 55% after 1 hour and 84% after 4 hours. The yield of nonanals was 55% after 1 hour and 82% after 4 hours. The yield nonanols was 0% after 1 hour and 2% after 4 hours.

Example 52

Intermediate-Pressure Hydroformylation of Butene Dimer 4.4 g of catalyst solution from Example 40 were evaporated to dryness at about 80° C. in an oil pump vacuum. The use of the catalyst residue which remained, 24.8 g (221 mmol) of butene dimer (obtained by nickel-catalyzed dimerization of n-butenes, degree of branching=1.06) and 25.0 g of Texanol® in the general experimental procedure (variant A) at 160° C. and 60 bar of $CO/H_2$ gave a conversion of butene dimer of 82% after 1 hour and 96% after 4 hours. The yield of nonanals was 76% after 1 hour and 69% after 4 hours. The yield of nonanols was 5% after 1 hour and 22% after 4 hours.

Example 53

Intermediate-Pressure Hydroformylation of Butene Dimer 1.4 g of catalyst solution from Example 41 were evaporated to dryness at about 80° C. in an oil pump vacuum. The use of the catalyst residue which remained, 24.8 g (221 mmol) of butene dimer (obtained by nickel-catalyzed dimerization of n-butenes, degree of branching=1.06) and 25.0 g of Texanol® in the general experimental procedure (variant A) at 140° C. and 80 bar of $CO/H_2$ gave a conversion of butene dimer of 45% after 1 hour and 70% after 4 hours. The yield of nonanals was 45% after 1 hour and 70% after 4 hours.

Example 54

Low-Pressure Hydroformylation of Butene Dimer 0.88 g of catalyst solution from Example 42 was evaporated to dryness at about 80° C. in an oil pump vacuum. The use of the catalyst residue which remained, 1.3 mg of dicarbonylrhodium acetylacetonate, 21.5 g (192 mmol) of butene dimer (obtained by nickel-catalyzed dimerization of n-butenes, degree of branching=1.06) and 23.2 g of Texanol® in the general experimental procedure (variant A) at 110° C. and 20 bar of $CO/H_2$ gave a conversion of butene dimer of 29% after 1 hour and 46% after 4 hours. The yield of nonanals was 29% after 1 hour and 46% after 4 hours.

Example 55

Low-pressure Hydroformylation of Butene Dimer 0.89 g of catalyst solution from Example 42 was evaporated to dryness at about 80° C. in an oil pump vacuum. The use of the catalyst residue which remained, 1.7 mg of dicarbonylrhodium acetylacetonate, 24.7 g (220 mmol) of butene dimer (obtained by nickel-catalyzed dimerization of n-butenes, degree of branching=1.06) and 24.7 g of Texanol® in the general experimental procedure (variant A) at 140° C. and 20 bar of $CO/H_2$ gave a conversion of butene dimer of 44% after 1 hour and 70% after 4 hours. The yield of nonanals was 43% after 1 hour and 66% after 4 hours. The yield of nonanols was 1% after 1 hour and 4% after 4 hours.

Example 56

Intermediate-Pressure Hydroformylation of Butene Dimer 0.32 g of catalyst solution from Example 43 was evaporated to dryness at about 80° C. in an oil pump vacuum. The use of the catalyst residue which remained, 4.6 mg of dicarbonylrhodium acetylacetonate, 26.0 g (232 mmol) of butene dimer (obtained by nickel-catalyzed dimerization of n-butenes, degree of branching=1.06) and 25.0 g of Texanol® in the general experimental procedure (variant A) at 140° C. and 80 bar of $CO/H_2$ gave a conversion of butene dimer of 84% after 1 hour and 93% after 4 hours. The yield of nonanals was 82% after 1 hour and 85% after 4 hours. The yield of nonanols was 3% after 1 hour and 12% after 4 hours.

Example 57

Intermediate-Pressure Hydroformylation of Butene Dimer 2.2 g of catalyst solution from Example 10 were evaporated to dryness at about 80° C. in an oil pump vacuum. Use of the catalyst residue which remained, 24.8 g (221 mmol) of butene dimer (obtained by nickel-catalyzed dimerization of n-butenes, degree of branching=1.06) and 25.0 g of Texanol® in the general experimental procedure (variant A) at 160° C. and 60 bar of $CO/H_2$ gave a conversion of butene dimer of 75% after 1 hour and 95% after 4 hours. The yield of nonanals was 70% after 1 hour and 69% after 4 hours. The yield of nonanols was 4% after 1 hour and 21% after 4 hours.

95%. The product could additionally be confirmed by $^{31}$P-NMR spectroscopy.

Example 58

Intermediate-Pressure Hydroformylation of Butene Dimer 1.4 g of catalyst solution from Example 44 were evaporated to dryness at about 80° C. in an oil pump vacuum. Use of the catalyst residue which remained, 25.1 g (224 mmol) of butene dimer (obtained by nickel-catalyzed dimerization of n-butenes, degree of branching=1.06) and 25.0 g of Texanol® in the general experimental procedure (variant A) at 160° C. and 60 bar of $CO/H_2$ gave a conversion of butene dimer of 52% after 1 hour and 88% after 4 hours. The yield of nonanals was 51% after 1 hour and 77% after 4 hours. The yield of nonanols was 1% after 1 hour and 9% after 4 hours.

Example 59

Intermediate-Pressure Hydroformylation of Butene Dimer 4.3 g of catalyst solution from Example 45 were evaporated to dryness at about 80° C. in an oil pump vacuum. Use of the catalyst residue which remained, 25.4 g (226 mmol) of butene dimer (obtained by nickel-catalyzed dimerization of n-butenes, degree of branching=1.06) and 25.0 g of Texanol® in the general experimental procedure (variant A) at 160° C. and 60 bar of $CO/H_2$ gave a conversion of butene dimer of 31% after 1 hour and 53% after 4 hours. The yield of nonanals was 31% after 1 hour and 50% after 4 hours. The yield of nonanols was 0% after 1 hour and 1% after 4 hours.

Example 60

Intermediate-Pressure Hydroformylation of Butene Dimer 6.0 g of catalyst solution from Example 46 were evaporated to dryness at about 80° C. in an oil pump vacuum. Use of the catalyst residue which remained, 8.8 g (78 mmol) of butene dimer (obtained by nickel-catalyzed dimerization of n-butenes, degree of branching=1.06) and 8.3 g of Texanol® in the general experimental procedure (variant A) at 160° C. and 60 bar of $CO/H_2$ gave a conversion of butene dimer of 50% after 1 hour and 97% after 24 hours. The yield of nonanals was 43% after 1 hour and 44% after 24 hours. The yield of nonanols was 1% after 1 hour and 41% after 24 hours.

Example 61

Intermediate-Pressure Hydroformylation of Butene Dimer 0.68 g of ligand solution from Example 47 was evaporated to dryness in an oil pump vacuum. Use of the ligand which remained, 7.5 mg (0.029 mmol) of dicarbonylrhodium acetylacetonate, 26.0 g (232 mmol) of butene dimer (obtained by nickel-catalyzed dimerization of n-butenes, degree of branching=1.06) and 25.0 g of Texanol® in the general experimental procedure (variant A) at 160° C. and 60 bar of $CO/H_2$ gave a conversion of butene dimer of 80% after 1 hour and 96% after 4 hours. The yield of nonanals was 75% after 1 hour and 75% after 4 hours. The yield of nonanols was 4% after 1 hour and 17% after 4 hours.

Example 62

Intermediate-Pressure Hydroformylation of Butene Dimer 0.68 g of ligand solution from Example 47 was evaporated to dryness in an oil pump vacuum. Use of the ligand which remained, 7.4 mg (0.029 mmol) of dicarbonylrhodium acetylacetonate, 25.3 g (225 mmol) of butene dimer (obtained by nickel-catalyzed dimerization of n-butenes, degree of branching=1.06) and 25.0 g of Texanol® in the general experimental procedure (variant A) at 140° C. and 80 bar of $CO/H_2$ gave a conversion of butene dimer of 75% after 1 hour and 95% after 4 hours. The yield of nonanals was 73% after 1 hour and 88% after 4 hours. The yield of nonanols was 1% after 1 hour and 5% after 4 hours.

Example 63

Intermediate-Pressure Hydroformylation of Butene Dimer 1.54 g of ligand solution from Example 48 were evaporated to dryness in an oil pump vacuum. Use of the ligand which remained, 7.4 mg (0.029 mmol) of dicarbonylrhodium acetylacetonate, 25.6 g (228 mmol) of butene dimer (obtained by nickel-catalyzed dimerization of n-butenes, degree of branching=1.06) and 25.0 g of Texanol® in the general experimental procedure (variant A) at 160° C. and 60 bar of $CO/H_2$ gave a conversion of butene dimer of 75% after 1 hour and 95% after 4 hours. The yield of nonanals was 70% after 1 hour and 75% after 4 hours. The yield of nonanols was 4% after 1 hour and 16% after 4 hours.

Example 64

Intermediate-Pressure Hydroformylation of Butene Dimer 1.55 g of ligand solution from Example 48 were evaporated to dryness in an oil pump vacuum. Use of the ligand which remained, 7.5 mg (0.029 mmol) of dicarbonylrhodium acetylacetonate, 25.5 g (227 mmol) of butene dimer (obtained by nickel-catalyzed dimerization of n-butenes, degree of branching=1.06) and 25.0 g of Texanol® in the general experimental procedure (variant A) at 140° C. and 80 bar of $CO/H_2$ gave a conversion of butene dimer of 60% after 1 hour and 87% after 4 hours. The yield of nonanals was 59% after 1 hour and 81% after 4 hours. The yield of nonanols was 1% after 1 hour and 3% after 4 hours.

Example 65

Intermediate-Pressure Hydroformylation of Butene Dimer 6.3 g of catalyst solution from Example 49 were evaporated to dryness at about 80° C. in an oil pump vacuum. Use of the catalyst residue which remained, 25.7 g (229 mmol) of butene dimer (obtained by nickel-catalyzed dimerization of n-butenes, degree of branching=1.06) and 25.1 g of Texanol® in the general experimental procedure (variant A) at 140° C. and 80 bar of $CO/H_2$ gave a conversion of butene dimer of 52% after 1 hour and 83% after 4 hours. The yield of nonanals was 51% after 1 hour and 76% after 4 hours. The yield of nonanols was 0% after 1 hour and 3% after 4 hours.

Example 66

Intermediate-Pressure Hydroformylation of Butene Dimer 0.32 g of catalyst solution from Example 43 was evaporated to dryness at about 80° C. in an oil pump vacuum. Use of the catalyst residue which remained, 4.6 mg (0.018 mmol) of dicarbonylrhodium acetylacetonate, 26.0 g (232 mmol) of butene dimer (obtained by nickel-catalyzed dimerization of n-butenes, degree of branching=1.06) and 25.0 g of Texanol® in the general experimental procedure (variant A) at 140° C. and 80 bar of $CO/H_2$ gave a conversion of butene dimer of 85% after 1 hour and 97% after 4 hours. The yield of nonanals was 82% after 1 hour and 85% after 4 hours. The yield of nonanols was 3% after 1 hour and 12% after 4 hours.

Example 67

Intermediate-Pressure Hydroformylation of Butene Dimer 0.32 g of catalyst solution from Example 43 was evaporated to dryness at about 80° C. in an oil pump vacuum. Use of the catalyst residue which remained, 4.6 mg (0.018 mmol) of dicarbonylrhodium acetylacetonate, 26.0 g (232 mmol) of butene dimer (obtained by nickel-catalyzed dimerization of n-butenes, degree of branching=1.06) and 25.0 g of Texanol® in the general experimental procedure (variant A) at 140° C. and 80 bar of $CO/H_2$ gave a conversion of butene dimer of 85% after 1 hour and 97% after 4 hours. The yield of nonanals was 82% after 1 hour and 85% after 4 hours. The yield of nonanols was 3% after 1 hour and 12% after 4 hours.

Example 68

Intermediate-Pressure Hydroformylation of $C_{12}/C_{14}$-alpha-olefins 0.33 g of catalyst solution from Example 43 was evaporated to dryness at about 80° C. in an oil pump vacuum. Use of the catalyst residue which remained, 4.7 mg (0.018 mmol) of dicarbonylrhodium acetylacetonate, 25.4 g of $C_{12}/C_{14}$-alpha-olefins (molar ratio of $C_{12}$-olefins:$C_{14}$-olefins=70:30; composition: 90% of 1-alkenes, 2% of internal olefins and 8% of vinylidenes) and 25.0 g of toluene in the general experimental procedure (variant A) at 100° C. and 80 bar of $CO/H_2$ gave a conversion of $C_{12}/C_{14}$-alpha-olefins of 93% after 1 hour and 97% after 4 hours. The yield of aldehydes was 93% after 1 hour and 97% after 4 hours.

Example 69

Intermediate-Pressure Hydroformylation of $C_{12}/C_{14}$-alpha-olefins 0.83 g of catalyst solution from Example 43 was evaporated to dryness at about 80° C. in an oil pump vacuum. Use of the catalyst residue which remained, 25.2 g of $C_{12}/C_{14}$-alpha-olefins (molar ratio of $C_{12}$-olefins:$C_{14}$-olefins=70:30; composition: 90% of 1-alkenes, 2% of internal olefins and 8% of vinylidenes) and 25.0 g of toluene in the general experimental procedure (variant A) at 120° C. and 80 bar of $CO/H_2$ gave a conversion of $C_{12}/C_{14}$-alpha-olefins of 98% after 1 hour and 99% after 4 hours. The yield of aldehydes was 97% after 1 hour and 98% after 4 hours. The yield of alcohols was 0% after 1 hour and 1% after 4 hours.

Example 70

Intermediate-Pressure Hydroformylation of $C_{12}/C_{14}$-alpha-olefins 0.84 g of catalyst solution from Example 43 was evaporated to dryness at about 80° C. in an oil pump vacuum. Use of the catalyst residue which remained, 25.5 g of $C_{12}/C_{14}$-alpha-olefins (molar ratio of $C_{12}$-olefins:$C_{14}$-olefins=70:30; composition: 90% of 1-alkenes, 2% of internal olefins and 8% of vinylidenes) and 25.0 g of toluene in the general experimental procedure (variant A) at 140° C. and 80 bar of $CO/H_2$ gave a conversion of $C_{12}/C_{14}$-alpha-olefins of 98% after 1 hour. The yield of aldehydes was 97% after 1 hour. The yield of alcohols was 1% after 1 hour.

Example 71

Low-Pressure Hydroformylation of $C_{12}/C_{14}$-alpha-olefins 0.84 g of catalyst solution from Example 43 was evaporated to dryness at about 80° C. in an oil pump vacuum. Use of the catalyst residue which remained, 24.9 g of $C_{12}/C_{14}$-alpha-olefins (molar ratio of $C_{12}$-olefins:$C_{14}$-olefins=70:30; composition: 90% of 1-alkenes, 2% of internal olefins and 8% of vinylidenes) and 25.1 g of toluene in the general experimental procedure (variant A) at 110° C. and 20 bar of $CO/H_2$ gave a conversion of $C_{12}/C_{14}$-alpha-olefins of 93% after 1 hour and 99% after 4 hours. The yield of aldehydes was 93% after 1 hour and 98% after 4 hours. The yield of alcohols was 0% after 1 hour and 1% after 4 hours.

Example 72

Low-pressure Hydroformylation of 2-octene 0.83 g of catalyst solution from Example 43 was evaporated to dryness at about 80° C. in an oil pump vacuum. The use of the catalyst residue which remained, 25.5 g (227 mmol) of 2-octene (cis:trans ratio=80:20) and 25.1 g of toluene in the general experimental procedure (variant A) at 110° C. and 20 bar of $CO/H_2$ for 3 hours gave a 2-octene conversion of 99%. The yield of nonanals was 97%, the selectivity to n-nonanal (proportion of n product) was 5% and the selectivity to n-nonanal and 2-methyl-octanal (proportion of α products) was 58%.

Example 73

Low-pressure Hydroformylation of $C_{12}/C_{14}$-alpha-olefins 0.83 g of catalyst solution from Example 43 was evaporated to dryness at about 80° C. in an oil pump vacuum. Use of the catalyst residue which remained, 25.1 g of $C_{12}/C_{14}$-alpha-olefins (molar ratio of $C_{12}$-olefins:$C_{14}$-olefins=70:30; composition: 90% of 1-alkenes, 2% of internal olefins and 8% of vinylidenes) and 25.0 g of toluene in the general experimental procedure (variant A) at 140° C. and 20 bar of $CO/H_2$ gave a conversion of $C_{12}/C_{14}$-alpha-olefins of 95% after 1 hour and 98% after 4 hours. The yield of aldehydes was 93% after 1 hour and 87% after 4 hours. The yield of alcohols was 2% after 1 hour and 10% after 4 hours.

Example 74

Low-Pressure Hydroformylation of $C_{12}/C_{14}$-alpha-olefins 0.83 g of catalyst solution from Example 43 was evaporated to dryness at about 80° C. in an oil pump vacuum. Use of the catalyst residue which remained, 26.0 g of $C_{12}/C_{14}$-alpha-olefins (molar ratio of $C_{12}$-olefins:$C_{14}$-olefins=68:32; composition: 84% of 1-alkenes, 4% of internal olefins and 12% of vinylidenes) and 25.1 g of toluene in the general experimental procedure (variant A) at 80° C. and 20 bar of $CO/H_2$ gave a conversion of $C_{12}/C_{14}$-alpha-olefins of 61% after 1 hour and 87% after 4 hours. The yield of aldehydes was 61% after 1 hour and 87% after 4 hours.

Example 75

Low-Pressure Hydroformylation of $C_{12}/C_{14}$-alpha-olefins 0.84 g of catalyst solution from Example 43 was evaporated to dryness at about 80° C. in an oil pump vacuum. Use of the catalyst residue which remained, 24.9 g of $C_{12}/C_{14}$-alpha-olefins (molar ratio of $C_{12}$-olefins:$C_{14}$-olefins=68:32; composition: 84% of 1-alkenes, 4% of internal olefins and 12% of vinylidenes) and 25.0 g of toluene in the general experimental procedure (variant A) at 110° C. and 20 bar of $CO/H_2$ gave a conversion of $C_{12}/C_{14}$-alpha-olefins of 83% after 0.5 hour and 95% after 4 hours. The yield of aldehydes was 83% after 0.5 hour and 95% after 4 hours. The yield of alcohols was 0% after 0.5 hour and 1% after 4 hours.

Example 76

Low-Pressure Hydroformylation of $C_{12}/C_{14}$-alpha-olefins 0.83 g of catalyst solution from Example 43 was evaporated to dryness at about 80° C. in an oil pump vacuum. Use of the catalyst residue which remained, 25.0 g of $C_{12}/C_{14}$-alpha-olefins (molar ratio of $C_{12}$-olefins:$C_{14}$-olefins=68:32; composition: 84% of 1-alkenes, 4% of internal olefins and 12% of vinylidenes) and 25.1 g of toluene in the general experimental procedure (variant A) at 140° C. and 20 bar of $CO/H_2$ gave a conversion of $C_{12}/C_{14}$-alpha-olefins of 89% after 1 hour and 94% after 4 hours. The yield of aldehydes was 87% after 1 hour and 86% after 4 hours. The yield of alcohols was 2% after 1 hour and 8% after 4 hours.

Example 77

Low-pressure Hydroformylation of Diisobutene 0.83 g of catalyst solution from Example 43 was evaporated to dryness at about 80° C. in an oil pump vacuum. Use of the catalyst residue which remained, 25.5 g (227 mmol) of diisobutene (composition: 73% of 2,4,4-trimethyl-1-pentene, 18% of 2,4,4-trimethyl-2-pentene, 9% of internal, branched octenes) and 25.1 g of toluene in the general experimental procedure (variant A) at 110° C. and 20 bar of $CO/H_2$ gave a conversion of diisobutene of 27% after 4 hours and 69% after 24 hours. The yield of nonanals was 24% after 4 hours and 64% after 24 hours. The yield of alcohols was 1% after 4 hours and 4% after 24 hours.

Example 78

Low-Pressure Hydroformylation of $C_{12}/C_{14}$-alpha-olefins 1.22 g of catalyst solution from Example 50 were evaporated to dryness at about 80° C. in an oil pump vacuum. Use of the catalyst residue which remained, 25.1 g of $C_{12}/C_{14}$-alpha-olefins (molar ratio of $C_{12}$-olefins:$C_{14}$-olefins=68:32; composition: 84% of 1-alkenes, 4% of internal olefins and 12% of vinylidenes) and 25.0 g of toluene in the general experimental procedure (variant A) at 110° C. and 20 bar of $CO/H_2$ gave a conversion of $C_{12}/C_{14}$-alpha-olefins of 88% after 1 hour and 95% after 4 hours. The yield of aldehydes was 88% after 1 hour and 94% after 4 hours. The yield of alcohols was 0% after 1 hour and 1% after 4 hours.

Example 79

Intermediate-Pressure Hydroformylation of Butene Dimer 0.37 g of catalyst solution from Example 50 was evaporated to dryness at about 80° C. in an oil pump vacuum. Use of the catalyst residue which remained, 5.6 mg (0.022 mmol) of dicarbonylrhodium acetylacetonate, 25.6 g (228 mmol) of butene dimer (obtained by nickel-catalyzed dimerization of n-butenes, degree of branching=1.06) and 25.0 g of Texanol® in the general experimental procedure (variant A) at 140° C. at 80 bar of $CO/H_2$ gave a conversion of butene dimer of 87% after 1 hour and 96% after 4 hours. The yield of nonanals was 83% after 1 hour and 79% after 4 hours. The yield of nonanols was 3% after 1 hour and 16% after 4 hours.

Example 80

Intermediate-Pressure Hydroformylation of Diisobutene 0.33 g of catalyst solution from Example 43 was evaporated to dryness at about 80° C. in an oil pump vacuum. Use of the catalyst residue which remained, 4.8 mg (0.019 mmol) of dicarbonylrhodium acetylacetonate, 25.4 g (226 mmol) of diisobutene (composition: 73% of 2,4,4-trimethyl-1-pentene, 18% of 2,4,4-trimethyl-2-pentene, 9% of internal, branched octenes) and 24.9 g of toluene in the general experimental procedure (variant A) at 140° C. and 80 bar of $CO/H_2$ gave a conversion of diisobutene of 76% after 1 hour and 99% after 4 hours. The yield of nonanals was 70% after 1 hour and 88% after 4 hours. The yield of alcohols was 4% after 1 hour and 9% after 4 hours.

Example 81

Low-pressure Hydroformylation of Diisobutene 0.84 g of catalyst solution from Example 43 was evaporated to dryness at about 80° C. in an oil pump vacuum. Use of the catalyst residue which remained, 25.6 g (228 mmol) of diisobutene (composition: 73% of 2,4,4-trimethyl-1-pentene, 18% of 2,4,4-trimethyl-2-pentene, 9% of internal, branched octenes) and 25.0 g of toluene in the general experimental procedure (variant A) at 140° C. and 20 bar of $CO/H_2$ gave a conversion of diisobutene of 72% after 4 hours and 97% after 24 hours. The yield of nonanals was 62% after 4 hours and 53% after 24 hours. The yield of alcohols was 7% after 4 hours and 31% after 24 hours.

Example 82

Low-pressure Hydroformylation of 2-ethyl-1-hexene 0.83 g of catalyst solution from Example 43 was evaporated to dryness at about 80° C. in an oil pump vacuum. Use of the catalyst residue which remained, 25.2 g (225 mmol) of 2-ethyl-1-hexene and 25.0 g of toluene in the general experimental procedure (variant A) at 80° C. and 20 bar of $CO/H_2$ gave a 2-ethyl-1-hexene conversion of 87% after 4 hours and 98% after 24 hours. The yield of nonanals was 86% after 4 hours and 93% after 24 hours. The yield of alcohols was 1% after 4 hours and 5% after 24 hours.

Example 83

Low Pressure Hydroformylation of 2-ethyl-1-hexene 1.02 g of catalyst solution from Example 42 were evaporated to dryness at about 80° C. in an oil pump vacuum. Use of the catalyst residue which remained, 20.4 g (182 mmol) of 2-ethyl-1-hexene and 25.0 g of toluene in the general experimental procedure (variant A) at 140° C. and 20 bar of $CO/H_2$ gave a 2-ethyl-1-hexene conversion of 56% after 4 hours and 88% after 24 hours. The yield of nonanals was 52% after 4 hours and 57% after 24 hours. The yield of alcohols was 2% after 4 hours and 21% after 24 hours.

Example 84

Low-Pressure Hydroformylation of 1-octene 1.25 g of catalyst solution from Example 42 were evaporated to dryness at about 80° C. in an oil pump vacuum. Use of the catalyst residue which remained, 25.0 g (223 mmol) of 1-octene and 25.0 g of toluene in the general experimental procedure (variant A) at 110° C. and 20 bar of $CO/H_2$ for 3 hours gave a 1-octene conversion of 99%. The yield of nonanals was 98%, the selectivity to n-nonanal (proportion of n product) was 59% and the selectivity to n-nonanal and 2-methyloctanal (proportion of α products) was 95%.

Example 85

Continuous Intermediate-Pressure Hydroformylation of Butene Dimer

Butene dimer (obtained by nickel-catalyzed dimerization of n-butenes, degree of branching=1.06) was hydroformylated continuously using the catalyst system rhodium/2,6-bis(2,4-dimethylphenyl)-1-octyl-4-phenylphosphacyclohexane in a miniplant as shown in FIG. 1, but using a cascade comprising two reactors.

The catalyst rhodium/2,6-bis(2,4-dimethylphenyl)-1-octyl-4-phenylphosphacyclohexane was prepared by rhodium-catalyzed hydrogenation of 2,6-bis(2,4-dimethylphenyl)-4-phenylphosphabenzene in the presence of butene dimer. The plant was operated continuously as described below for the hydroformylation, except that the temperature was 150° C. in both reactors and a hydrogen pressure of 80 bar was employed.

For the continuous hydroformylation, 300 g/h of butene dimer were hydroformylated at an internal reactor temperature of 140° C. and a $CO/H_2$ pressure of 80 bar in both reactors in the presence of 15–60 ppm of rhodium and the previously prepared 2,6-bis(2,4-dimethylphenyl)-1-octyl-4-phenylphosphacyclohexane as cocatalyst [P/Rh ratio=3–4 (mol:mol)] (the concentration figures are based on the amount of reaction mixture) and 1 kg of Texanol® as solvent. A $CO/H_2$ (1:1) gas mixture was fed to the reactors in such an amount that a constant waste gas flow via a pressure separator of about 75 standard 1/h resulted. The liquid output from the reactor was depressurized in a flash vessel and fractionated in a wiped film evaporator to give a distillate comprising mainly nonanals, nonanols and $C_8$-hydrocarbons and catalyst-containing bottoms. 200 g of the catalyst-containing bottoms were recirculated continuously to the first reactor of the two-stage reaction cascade. The plant was able to be operated stably and without a loss of activity for 24 balance days. Degradation of the ligand was not observed. On the 14th balance day, 500 ml of the catalyst-containing bottoms were discharged, and on the 21st balance day, 760 ml of the catalyst-containing bottoms were discharged. The conversions, selectivities and space-time yields obtained are shown in Table 5 and FIG. 3.

Table 5: Conversions, selectivities and space-time yields in the continuous hydroformylation of butene dimer (80 bar $CO/H_2$ total pressure, L/Rh=3–4, about 15–60 ppm of Rh) without taking account of high boiler formation.

| | | |
|---|---|---|
| Butene dimer (conversion) | [%] | 81.3 |
| Nonanals/nonanols (yield) | [%] | 79.8 |
| Nonanals (yield) | [%] | 76.8 |
| Nonanols (yield) | [%] | 2.9 |
| Space-time yield | [g/l · h] | 89.1 |

The experiments 86 to 95 below were carried out under nitrogen or argon as protective gas.

Example 86

Preparation of 2,6-bis(2,4-dimethylphenyl)-4-phenylphosphacyclohexane from 2,6-bis(2,4-dimethylphenyl)-4-phenylphosphabenzene A solution of 10.0 g (26.3 mmol) of 2,6-bis(2,4-dimethylphenyl)-4-phenylphosphabenzene, 1.0 g (2.5 mmol) of ruthenium(III) acetylacetonate and 5 ml of toluene in 100 ml of cyclohexane was placed in an autoclave which had been flushed with hydrogen. The autoclave was pressurized with 10 bar of hydrogen at room temperature. While stirring with a sparging stirrer, the reaction mixture was heated to 160° C. A reaction pressure of 80 bar was then set by means of hydrogen. During the reaction, the pressure in the autoclave was maintained by introduction of further hydrogen via a pressure regulator. After a reaction time of 4 days, the autoclave was cooled, depressurized and emptied. The white solid in the reaction mixture was isolated by filtration. The reaction solution obtained was then evaporated completely in a high vacuum. The residue was stirred in a little cyclohexane. The white solid which precipitated was filtered off and washed a number of times with a little cyclohexane. A total of 4.0 g (39% of theory) of the product in the form of a white solid could be isolated.

Example 87

Preparation of 2,6-bis(2,4-dimethylphenyl)-1-octyl-4-phenylphosphacyclohexane from 2,6-bis(2,4-dimethylphenyl)-4-phenylphosphacyclohexane A suspension of 0.5 g (1.3 mmol) of 2,6-bis(2,4-dimethylphenyl)-4-phenylphosphacyclohexane in 30 g (267 mmol) of 1-octene is heated at 120° C. under 3 bar nitrogen pressure for 6 hours. GC analysis of the reaction mixture indicates the formation of 2,6-bis(2,4-dimethylphenyl)-1-octyl-4-phenylphosphacyclohexane in a yield of 33%.

Example 88

Preparation of 2,6-bis(2,4-dimethylphenyl)-1-octyl-4-phenylphosphacyclohexane from 2,6-bis(2,4-dimethylphenyl)-4-phenylphosphacyclohexane A solution of 4 mg (0.024 mmol) of 2,2'-azobisisobutyronitrile (Vazo 64) in 0.8 ml of toluene is added dropwise at a temperature of 82° C. to a mixture of 0.5 g (1.3 mmol) of 2,6-bis(2,4-dimethylphenyl)-4-phenylphosphacyclohexane and 0.30 g (2.7 mmol) of 1-octene in 0.8 ml of toluene over a period of 4 hours. This results in a clear, pale yellow solution. GC analysis of the reaction mixture indicates the formation of 2,6-bis(2,4-dimethylphenyl)-1-octyl-4-phenylphosphacyclohexane in a yield of 80%.

Example 89

Preparation of 2,6-bis(2,4-dimethylphenyl)-1-[2-(2-methoxy-ethoxy)ethyl]-4-phenylphosphacyclohexane from 2,6-bis(2,4-dimethylphenyl)-4-phenylphosphacyclohexane A solution of 4 mg (0.024 mmol) of 2,2'-azobisisobutyronitrile (Vazo 64) in 0.8 ml of toluene is added dropwise at a temperature of 82° C. to a mixture of 0.30 g (0.77 mmol) of 2,6-bis(2,4-dimethylphenyl)-4-phenylphosphacyclohexane and 0.096 g (0.94 mmol) of ethylene glycol methyl vinyl ether in 0.8 ml of toluene over a period of 4 hours. This results in a clear, pale red solution. GC analysis of the reaction mixture indicates the formation of 2,6-bis(2,4-dimethylphenyl)-1-[2-(2-methoxy-ethoxy)ethyl]-4-phenylphosphacyclohexane in a yield of 61%.

Example 90

Preparation of 1,3-di[2,6-bis(2,4-dimethylphenyl)-4-phenylphosphacyclohexan-1-yl]propane from 2,6-bis(2,4-dimethylphenyl)-4-phenylphosphacyclohexane A suspension of 3.1 g (7.8 mmol) of 2,6-bis(2,4-dimethylphenyl)-4-phenylphosphacyclohexane (Example 86) and 3.7 ml of a 2.5 molar butyllithium solution in hexane in a solution of 15 ml of hexane and 11 ml of tetrahydrofuran was stirred at about 30° C. for 24 hours. The reaction mixture was subsequently admixed with 0.43 g (3.8 mmol) of 1,3-dichloropropane and subsequently stirred for another 4 hours at room temperature. After filtration of the reaction mixture, the solution obtained was washed a number of times with 50 ml each time of water. The organic phase was evaporated to dryness in a high vacuum with gentle warming and the residue was subsequently chromatographed on a neutral aluminum oxide column using toluene as eluant. Evaporation of the toluene solution in a high vacuum and washing of the residue a number of times with pentane gave 2.2 g (35% of theory) of the product in the form of a white, finely crystalline powder.

Example 91

Preparation of 1-butyl-2,6-bis(2,4-dimethylphenyl)-4-phenylphosphacyclohexane from 2,6-bis(2,4-dimethylphenyl)-4-phenylphosphabenzene 3.9 g of a 15% strength solution of n-butyllithium in n-hexane are slowly added dropwise while stirring to a solution of 3.1 g (8.2 mmol) of 2,6-bis(2,4-dimethylphenyl)-4-phenylphosphabenzene in 100 ml of toluene which has been cooled to about 10° C. The solution is then stirred for another 20 hours at room temperature. To complete the reaction, a further 1.5 g of a 15% strength solution of n-butyllithium in n-hexane were added and the solution was once more stirred for 20 hours at room temperature. The solution obtained was then admixed with 100 ml of water while stirring vigorously. The organic phase was separated off and analyzed. GC analysis (NP detector) and $^{31}$P-NMR spectroscopy ($\delta$=−55 and −40 ppm) indicate the selective formation of isomeric 1-butyl-2,6-bis(2,4-dimethylphenyl)-4-phenylphosphacyclohexadienes. 40 g of the toluene solution obtained were transferred together with 0.10 g (0.25 mmol) of ruthenium(III) acetylacetonate to a 100 ml autoclave which had been flushed with hydrogen and the autoclave was pressurized with 5 bar of hydrogen at room temperature. While stirring vigorously with a sparging stirrer, the reaction mixture was heated to 160° C. over a period of 30 minutes. A reaction pressure of 80 bar was then set by means of hydrogen. During the reaction, the pressure in the autoclave was maintained by introduction of further hydrogen via a pressure regulator. After a reaction time of 24 hours, the autoclave was cooled, depressurized and emptied. GC analysis (NP detector) and $^{31}$P-NMR spectroscopy ($\delta$=−29) of the reaction solution indicate the selective formation of 1-butyl-2,6-bis(2,4-dimethylphenyl)-4-phenylphosphacyclohexane. Removal of the volatile constituents in an oil pump vacuum and bulb tube distillation of the residue at 300° C. and 2 mbar give 0.4 g of the product.

Example 92

Preparation of 1-(2-methylpropyl-2,6-bis(2,4-dimethylphenyl)-4-phenylphosphacyclohexane from 2,6-bis(2,4-dimethylphenyl)-4-phenylphosphabenzene 3.0 ml of a 1.3 M solution of sec-butyllithium in cyclohexane are slowly added dropwise at room temperature to a solution of 0.74 g (2.0 mmol) of 2,6-bis(2,4-dimethylphenyl)-4-phenylphosphabenzene in 50 ml of toluene. The solution is then stirred for another 3 hours at room temperature. To complete the reaction, a further 3.0 ml of a 1.3 M solution of sec-butyllithium in cyclohexane were added and the solution was stirred for another 17 hours at room temperature. The solution obtained was then admixed with 70 ml of water while stirring vigorously. The organic phase was separated off and analyzed. GC analysis (NP detector) indicates the selective formation of isomeric 1-(2-methylpropyl)-2,6-bis(2,4-dimethylphenyl)-4-phenylphosphacyclohexadienes.

40 g of the toluene solution obtained were transferred together with 0.10 g (0.25 mmol) of ruthenium(III) acetylacetonate to a 100 ml autoclave which had been flushed with hydrogen and the autoclave was pressurized with 5 bar of hydrogen at room temperature. While stirring vigorously with a sparging stirrer, the reaction mixture was heated to 160° C. over a period of 30 minutes. A reaction pressure of 70 bar was then set by means of hydrogen. During the reaction, the pressure in the autoclave was maintained by introduction of further hydrogen via a pressure regulator. After a reaction time of 24 hours, the autoclave was cooled, depressurized and emptied. GC analysis (NP detector) and $^{31}$P-NMR spectroscopy ($\delta$=−18 and −14) of the reaction solution indicate the selective formation of isomeric 1-(2-methylpropyl)-2,6-bis(2,4-dimethylphenyl)-4-phenylphosphacyclohexanes. Removal of the volatile constituents in an oil pump vacuum and bulb tube distillation of the residue at 300° C. and 2 mbar gave 0.2 g of the product.

Example 93

Preparation of 1-butyl-2,6-bis(2,4-dimethylphenyl)-4-phenyl-phosphacyclohexane from 2,6-bis(2,4-dimethylphenyl)-4-phenylphosphabenzene A solution of 5.91 g (64 mmol) of butyl chloride in 40 ml of THF (tetrahydrofuran) is slowly added dropwise to 3.1 g (128 mmol) of magnesium turnings in 20 ml of THF. The reaction mixture is subsequently refluxed for 2 hours. 7.0 g of the reaction solution obtained are then added dropwise at room temperature to a solution of 1.65 g (4.3 mmol) of 2,6-bis(2,4-dimethylphenyl)-4-phenylphosphabenzene in 20 ml of THF. The solution is then stirred for another 16 hours at room temperature. To complete the reaction, a further 7.1 g of the Grignard solution were added and the reaction mixture was stirred for another 4 hours at room temperature. The solution obtained is then admixed with 30 ml of water while stirring vigorously. GC analysis (NP detector) and $^{31}$P-NMR spectroscopy ($\delta$=−55 and −40 ppm) indicate the selective formation of isomeric 1-butyl-2,6-bis(2,4-dimethylphenyl)-4-phenylphosphacyclohexadiene.

The reaction mixture obtained was transferred together with 0.17 g (0.43 mmol) of ruthenium(III) acetylacetonate to a 100 ml autoclave which had been flushed with hydrogen and the autoclave was pressurized with 5 bar of hydrogen at room temperature. While stirring vigorously with a sparging stirrer, the reaction mixture was heated to 120° C. over a period of 30 minutes. A reaction pressure of 60 bar was then set by means of hydrogen. During the reaction, the pressure in the autoclave was maintained by introduction of further hydrogen via a pressure regulator. After a reaction time of 24 hours, the autoclave was cooled, depressurized and emptied. The reaction mixture was admixed with 50 ml of toluene. The organic phase was separated off and the aqueous phase was washed twice with toluene. Removal of the volatile constituents of the combined organic phases in an oil pump vacuum and bulb tube distillation of the residue at 250° C. and 0.07 mbar gives 0.62 g of the product. GC analysis (NP detector) and $^{31}$P-NMR spectroscopy ($\delta$=−31) confirm the formation of 1-butyl-2,6-bis(2,4-dimethylphenyl)-4-phenylphosphacylcohexane.

Example 94

Preparation of 1-polyethylene-2,6-bis(2,4-dimethylphenyl)-4-phenylphosphacyclohexadiene from 2,6-bis(2,4-dimethylphenyl)-4-phenylphosphabenzene A solution of 1.38 g (5.0 mmol) of a 2.5 M solution of n-butyl-lithium in hexane and 0.62 g (5.3 mmol) of N,N,N',N'-tetramethylethylenediamine in 30 ml of hexane were placed in an autoclave which had been flushed with inert gas. While stirring the reaction solution vigorously with a sparging stirrer, the autoclave was pressurized with 2 bar of ethene at room temperature. During the reaction, the pressure in the autoclave was maintained by introduction of further ethene via a pressure regulator. After a reaction time of 6 hours, the autoclave was depressurized and flushed with inert gas. A solution of 1.52 g (4.0 mmol) of 2,6-bis(2,4-dimethylphenyl)-4-phenylphosphabenzene in 10 ml of toluene was then added via a lock. The reaction mixture was stirred at 80° C. for 12 hours, subsequently admixed with 50 ml of water and also diluted with 20 ml of toluene. All volatile constituents were then removed in an oil pump vacuum. $^{31}$P-NMR spectroscopy (δ=−50, −40) of the residue obtained indicates the selective formation of isomeric 1-polyethylene-2,6-bis(2,4-dimethylphenyl)-4-phenylphosphacyclohexadienes.

Example 95

Reaction of 2,6-bis(2,4-dimethylphenyl)-4-phenylpyrylium tetrafluoroborate with Octylphosphine, Hydrogenation and Reduction to Form 1-octyl-2,6-bis(2,4-dimethylphenyl)-4-phenylphosphacyclohexane In an autoclave flushed with argon 20 g (44 mmol) of 2,6-bis(2,4-dimethylphenyl)-4-phenylpyrylium tetrafluoroborate were dissolved in 120 ml of butanol, admixed with 10 g (68 mmol) of octylphosphine and subsequently stirred at 120° C. for 6 hours. A further 5 g (34 mmol) of octylphosphine were added and the reaction solution was stirred at 120° C. for another 6 hours. After cooling to room temperature, the insoluble solid, namely unreacted pyrylium salt, was separated off by filtration. The solution obtained was then evaporated to dryness under reduced pressure while being warmed. The residue was dissolved in a mixture of toluene and dichloromethane and the solution was washed with water until the aqueous phase had a pH of 7. The solution obtained was filtered through silica gel and then evaporated to dryness under reduced pressure with gentle warming. The solid obtained was washed a number of times with a little pentane and subsequently dried under reduced pressure. This gave 22 g of a green solid.

6.33 g of the solid obtained were dissolved in 150 ml of toluene, admixed with 1.0 g (2.5 mmol) of ruthenium(III) acetylacetonate and transferred to a 100 ml autoclave which had been flushed with hydrogen. The autoclave was pressurized with 10 bar of hydrogen at room temperature. While stirring with a sparging stirrer, the reaction mixture was heated to 140° C. over a period of 30 minutes. A reaction pressure of 80 bar was then set by means of hydrogen. During the reaction, the pressure in the autoclave was maintained by introduction of further hydrogen via a pressure regulator. After 72 hours, the autoclave was cooled, depressurized and emptied.

Under argon, 30 g of the solution obtained in 200 g of toluene were cooled to about −5° C. 2.0 g (20 mmol) of triethylamine and subsequently 1.3 g (9.8 mmol) of trichlorosilane were slowly added thereto. The reaction mixture was subsequently stirred at room temperature for 24 hours. A further 1.5 g (11.1 mmol) of trichlorosilane were added and the reaction solution was stirred at room temperature for 24 hours. The reaction mixture was then filtered through kieselguhr. The solution obtained was evaporated under reduced pressure to one quarter of its original volume and then admixed with 100 ml of aqueous sodium hydroxide solution. The organic phase was separated off and filtered through a bed of aluminum oxide. Removal of the volatile constituents in an oil pump vacuum and bulb tube distillation of the residue at 300° C. and 0.03 mbar gave 0.12 g of the product. GC analysis (NP detector) and $^{31}$P-NMR spectroscopy confirm the formation of 1-octyl-2,6-bis(2,4-dimethylphenyl)-4-phenylphosphacyclohexane.

Example 96

Preparation of 1-dodecyl-2,6-bis(2,4-dimethylphenyl)-4-phenyl-phosphacyclohexane from 2,6-bis(2,4-dimethylphenyl)-4-phenyl-phosphacyclohexane 13.2 g of a solution of 0.039 g (0.24 mmol) of 2,2'-azo-isobutyronitrile (Vazo 64) in 19.3 g of toluene were added dropwise at a temperature of 92° C. to a mixture of 2.02 g (5.2 mmol) of 2,6-bis(2,4-dimethylphenyl)-4-phenylphosphacyclohexane and 1.20 g (7.1 mmol) of 1-dodecene in 1.5 g of toluene over a period of 10 hours. The mixture is subsequently stirred for another 10 hours at 92° C. This results in a clear, gray solution. The reaction solution obtained was evaporated to dryness in a high vacuum. The solid which remained was suspended in 140 ml of ethanol and then admixed with 60 ml of dichloromethane, resulting in a clear solution. The solution was evaporated in a high vacuum until the product precipitated as a white solid. The precipitated solid was filtered off and dried in a high vacuum. 1.9 g (65.5% of theory) of the product in the form of a white solid could be isolated.

Example 97

Preparation of 2,6-bis(2,4-dimethylphenyl)-4-phenyl-1-[methyl-poly(ethylene glycol)-500] phosphacyclohexane from 2,6-bis(2,4-dimethylphenyl)-4-phenylphosphacyclohexane 9 ml of a solution of 0.035 g (0.21 mmol) of 2,2'-azo-isobutyronitrile (Vazo 64) in 16 ml of toluene are added dropwise at a temperature of 82° C. to a mixture of 0.15 g (0.39 mmol) of 2,6-bis(2,4-dimethylphenyl)-4-phenylphosphacyclohexane and 0.85 g (1.45 mmol) of poly (ethylene glycol)-500 methyl vinyl ether in 1 ml of toluene over a period of 18 hours. This results in a clear, yellow solution. $^{31}$P-NMR spectroscopy indicates the selective formation of isomeric 2,6-bis(2,4-dimethylphenyl)-4-phenyl-1-[methylpoly(ethylene glycol)]phosphacyclohexanes in a yield of about 90%.

Example 98

Preparation of 2,6-bis(2,4-dimethylphenyl)-4-phenyl-1-[methyl-poly(ethylene glycol)-500] phosphacyclohexane from 2,6-bis(2,4-dimethylphenyl)-4-phenylphosphacyclohexane 11.8 ml of a solution of 0.096 g (0.58 mmol) of 2,2'-azobisisobutyronitrile (Vazo 64) in 38 ml of toluene are added dropwise at a temperature of 93° C. to a mixture of 0.15 g (0.39 mmol) of 2,6-bis(2,4-dimethylphenyl)-4-phenylphosphacyclohexane and 0.32 g (0.54 mmol) of poly (ethylene glycol)-500 methyl vinyl ether in 1 ml of toluene over a period of 18 hours. This results in a clear, yellow solution. $^{31}$P-NMR spectroscopy indicates the selective formation of isomeric 2,6-bis(2,4-dimethylphenyl)-4-phenyl-1-[methylpoly(ethylene glycol)]phosphacyclohexanes in a yield of about 66%. The reaction mixture obtained was stirred vigorously with 5 ml of water for 1 hour at room temperature. After phase separation, a phosphorus content of 1 000 ppm was found for the organic phase and a phosphorus content of 80 ppm was found for the aqueous phase.

Example 99

Preparation of 1-dodecyl-2,6-bis(2,4-dimethylphenyl)-4-phenyl-phosphacyclohexane from 2,6-bis(2,4-dimethylphenyl)-4-phenyl-phosphabenzene 50.4 g (202 mmol) of 1-dodecyl bromide are slowly added dropwise to 9.4 g (387 mmol) of magnesium turnings in 100 ml of THF while stirring. After the dropwise addition was complete, the reaction mixture was diluted with a further 100 ml of THF and then refluxed for 2 hours. The gray solution obtained was added dropwise to a solution of 53.2 g of 2,6-bis(2,4-dimethylphenyl)-4-phenylphosphabenzene in 100 ml of THF, resulting in a deep red reaction solution which was stirred for another 16 hours at room temperature and subsequently quenched with 350 ml of water while stirring vigorously. To improve the phase separation, the emulsion was admixed with 200 ml of toluene and 1 500 ml of ethyl acetate and subsequently washed four times with 500 ml each time of an aqueous, saturated ammonium chloride solution. The organic phase obtained was then evaporated to dryness in an oil pump vacuum. The residue obtained was taken up in 150 ml of toluene. $^{31}$P-NMR spectroscopy indicates the selective formation of isomeric 1-dodecyl-2,6-bis(2,4-dimethylphenyl)-4-phenylphosphacyclohexadienes.

125 g of the toluene solution obtained were transferred together with 0.52 g (1.3 mmol) of ruthenium(III) acetylacetonate and 50 ml of 1-octene to a 300 ml autoclave which had been flushed with hydrogen. The autoclave was pressurized with 10 bar of hydrogen at room temperature. While stirring vigorously with a sparging stirrer, the reaction mixture was heated to 110° C. over a period of 30 minutes. A reaction pressure of 80 bar was then set by means of hydrogen. During the reaction, the pressure in the autoclave was maintained by introduction of further hydrogen via a pressure regulator. After a reaction time of 72 hours, the autoclave ws cooled, depressurized and emptied. The solution obtained was filtered through aluminum oxide, subsequently evaporated in an oil pump vacuum and taken up in toluene. $^{31}$P-NMR spectroscopy ($\delta$=–30) of the solution indicates the selective formation of isomeric 1-dodecyl-2,6-bis(2,4-dimethylphenyl)-4-phenylphosphacyclohexanes. Analysis of the solution indicates a ruthenium content of 190 ppm and a phosphorus content of 11 000 ppm (P/Ru molar ratio=192).

Example 100

Preparation of 1-polyethylene-2,6-bis(2,4-dimethylphenyl)-4-phenylphosphacyclohexadiene from 2,6-bis(2,4-dimethylphenyl)-4-phenylphosphabenzene A solution of 2.68 g (9.65 mmol) of a 2.5 M solution of n-butyl-lithium in hexane and 1.22 g (10.5 mmol) N,N,N',N'-tetramethylethylenediamine in 60 ml of cyclohexane which had previously been dried over sodium was placed in a glass autoclave which had been flushed with inert gas. While stirring the reaction solution vigorously with a sparging stirrer, the autoclave was pressurized with 2 bar of ethene at room temperature. During the reaction, the pressure in the autoclave was maintained by introduction of further ethene via a pressure regulator. After a reaction time of 12 hours, the autoclave was depressurized and flushed with inert gas. A solution of 2.08 g (5.47 mmol) of 2,6-bis(2,4-dimethyl-phenyl)-4-phenylphosphabenzene in 100 ml of cyclohexane was then added via a lock. The reaction mixture was stirred at 80° C. for 20 hours, subsequently admixed with 50 ml of methanol and also diluted with 120 ml of toluene. The reaction solution was then washed three times with 50 ml each time of water. All volatile constituents were then removed in an oil pump vacuum. The residue which remained was dissolved in 100 ml of methanol and 60 ml of dichloromethane. The solution was evaporated in a high vacuum until a white solid precipitated. The precipitated solid was filtered off, washed with a little methanol and dried in a high vacuum. To remove unreacted polyethylene, the solid was once again stirred in 100 ml of toluene and 60 ml of dichloromethane and then filtered off on kieselguhr. The orange solution obtained was evaporated to dryness in a high vacuum, and subsequently dissolved in 80 ml of methanol and 80 ml of dichloromethane. The solution was evaporated in a high vacuum until a white solid precipitated. The precipitated white solid was filtered off, washed with a little methanol and dried in a high vacuum. 1.42 g of the product in the form of a pale yellow solid could be isolated. $^{31}$P-NMR spectroscopy ($\delta$=–40, –50) indicates the selective formation of isomeric 1-polyethylene-2,6-bis(2,4-dimethylphenyl)-4-phenylphosphacyclohexadienes. GPC analysis (calibration using polybutadiene standard from Polymer Laboratories) gave a number average molecular weight $M_n$ of about 830.

Example 101

Preparation of a rhodium/1-polybutylene-2,6-bis(2,4-dimethylphenyl)-4-phenylphosphacyclohexane Solution from 2,6-bis(2,4-dimethylphenyl)-4-phenylphosphabenzene 2 400 g of cyclohexane, 12 ml of THF and 180 g (3.33 mol) of butadiene were placed in a 10 1 vessel and subsequently admixed with 11.4 ml (16 mmol) of a 1.4 M solution of sec-butyllithium in cyclohexane. The solution was stirred at about 40° C. for 4 hours and subsequently admixed with 4.0 g (10.5 mmol) of 2,6-bis(2,4-dimethylphenyl)-4-phenylphosphabenzene. The reaction mixture was stirred at 60° C. for 24 hours and then admixed with an ethanol/water mixture. $^{31}$P-NMR spectroscopy of the reaction mixture obtained indicates the selective formation of isomeric 1-polybutadiene-2,6-bis(2,4-dimethylphenyl)-4-phenylphosphacyclohexadienes in a yield of about 94%. Analysis of the solution indicated a phosphorus content of 135 ppm. GPC analysis (calibration using a polystyrene calibration kit from Polymer Laboratories and conversion to polybutadiene using Mark-Houwink constants) gave a number average molecular weight $M_n$ of about 12 000.

299 g of the solution obtained were evaporated to about 50 ml in an oil pump vacuum. The remaining solution was transferred together with 34 mg (130 mmol) of dicarbonyl-rhodium acetylacetonate, 35 ml of 1-octene and 75 ml of toluene to a 300 ml altoclave which had been flushed with hydrogen. The autoclave was pressurized with 10 bar of hydrogen at room temperature. While stirring vigorously with a sparging stirrer, the reaction mixture was heated to 80° C. over a period of 30 minutes. A reaction pressure of 80 bar was then set by means of hydrogen. During the reaction, the pressure in the autoclave was maintained by introduction of further hydrogen via a pressure regulator. After a reaction time of 24 hours, the reaction temperatrure was increased to 160° C. while maintaining the reaction pressure. After a further reaction time of 24 hours, the autoclave was cooled, depressurized and emptied. The solution obtained was admixed with 65 g of Oxool 9N, and then freed of low boilers at about 150° C. in an oil pump vacuum. $^{31}$P-NMR spectroscopy ($\delta$=–30) of the solution indicates the selective formation of isomeric 1-polybutylene-2,6-bis(2,4-dimethylphenyl)-4-phenyl-phosphacyclohexanes. Analysis of the solution indicated a rhodium content of 155 ppm and a phosphorus content of 380 ppm (P/Rh molar ratio=8).

What is claimed is:

1. A process for the hydroformylation of olefins by reacting olefins with CO and $H_2$ in the presence of a rhodium complex as catalyst at from 20 to 250° C. and pressures of from 1 to 600 bar, where the catalyst comprises at least one ligand having at least one unbridged phosphacyclohexane and/or phosphacy-clohexene structural element selected from among phosphacyclohexanes of the formulae I and II

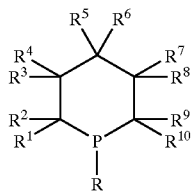

(I)

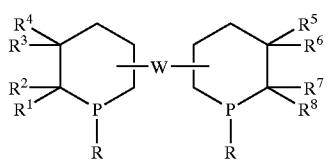

(II)

where
R
is hydrogen, $C_{1-100}$-alkyl, cycloalky, heterocycloalkyl, $C_{7-20}$-aralkyl, $C_{7-20}$-alkaryl, $C_{6-12}$-aryl, hetaryl, W'COO$^-$M$^+$, W'SO$_3^-$M$^+$, W'PO$_3^{2-}$M$^+_2$, W'NR'$_3^+$X$^-$, W'OR', W'NR'$_2$, W'COOR', W'SR', W'(CHR'CH$_2$O)$_x$R', W'(CH$_2$NR')$_x$R', W'(CH$_2$CH$_2$NR')$_x$R', W'((CH$_2$)$_4$O)$_x$R', or W'COR', where the radicals R in the formula II may also, in place of or in addition to the group W, together form a bridge having from 1 to 20 carbon atoms which may be part of a cyclic or aromatic group and may be interrupted by heteroatoms, where the radicals R in the formula II may also, in place of or in addition to the group W, together be a polyoxyalkylene or polyalkylenimine bridge having at least 21 carbon atoms, $R^1$ to $R^{10}$ are each, independently of one another, hydrogen, $C_{1-20}$-alkyl, $C_{7-20}$-aralkyl, $C_{7-20}$-alkaryl, $C_{6-12}$-aryl, where one or more carbon atoms may be replaced by heteroatoms, W'COO$^-$M$^+$, W'SO$_3^-$M$^+$, W'PO$_3^{2-}$M$^+_2$, W'NR'$_3^+$X$^-$, W'OR', W'NR'$_2$, W'COOR', W'SR', W'(CHR'CH$_2$O)$_x$R', W'(CH$_2$NR')$_x$R', W'(CH$_2$CH$_2$NR')$_x$R', W'((CH$_2$)$_4$O)$_x$R', W'halogen, W'NO$_2$, W'COR' or W'CN, where at least two of the radicals $R^1$ to $R^{10}$ are different from hydrogen, where one or more hydrogen atoms in the radicals R and $R^1$ to $R^{10}$ may be replaced by fluorine, W and W' are, independently of one another, single bonds or bridges having from 1 to 20 carbon atoms which may be part of a cyclic or aromatic group and may be interrupted by heteroatoms, where W may also be a polyoxyalkylene or polyalkylenimine bridge having at least 21 carbon atoms, R' is hydrogen, $C_{1-20}$-alkyl, carbonylalkyl, cycloalkyl or aryl, M+ is a cation equivalent, X$^-$ is an anion equivalent, x is from 1 to 240, where two gem nal radicals $R^1$ to $R^{10}$ may form an oxo group and one or more of the radicals R and $R^1$ to $R^{10}$ may bear an additional trivalent phosphorus or nitrogen group capable of coordination, where in each case two vicinal radicals may be joined to form fused aliphatic or aromatic rings, where two vicinal radicals $R^1$ to $R^{10}$ may also be a chemical bond, where two or more bridges W may be present in the compounds of the formula II and the atoms of the phosphacyclohexane rings which are not bound to the bridge(s) W may also bear substituents defined as for $R^1$ to $R^{10}$, where one of the radicals R or $R^1$ to $R^{10}$ in the compounds of the formula I and one of the radicals R or $R^1$ to $R^8$ or both radicals R together or a group W in the compounds of the formula II may also be a polymer radical having a number average molecular weight in the range from 500 to 50 000 and made up of repeating units derived from monomers selected from among monoolefins and diolefins, vinylaromatics, esters of α,β-ethylenically unsaturated monocarboxylic and dicarboxylic acids with $C_1$–$C_{30}$-alkanols, N-vinyl amides, N-vinyllactams, heterocyclic compounds which can be polymerized with ring opening and mixtures thereof.

2. A process as claimed in claim 1, wherein the compound of the formula I is selected from among compounds of the formula III

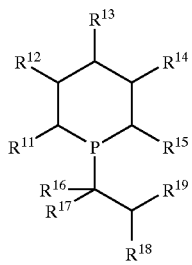

(III)

where:

$R^{11}$ to $R^{19}$ are each, independently of one another, hydrogen, $C_{1-20}$-alkyl, $C_{7-20}$-aralkyl, $C_{7-20}$-alkaryl, $C_{6-12}$-aryl, where one or more carbon atoms may be replaced by heteroatoms, W'COO$^-$M$^+$, W'SO$_3^-$M$^+$, W'PO$_3^{2-}$M$^+_2$, W'NR'$_3^+$X$^-$, W'OR', W'NR'$_2$, W'COOR', W'SR', W'(CHR'CH$_2$O)$_x$R', W'(CH$_2$NR')$_x$R', W'(CH$_2$CH$_2$NR')$_x$R', where in each case two vicinal radicals $R^{11}$ to $R^{15}$ and/or $R^{17}$ and $R^{18}$ and/or $R^{16}$ and $R^{17}$ and/or $R^{16}$ and $R^{19}$ and/or $R^{18}$ and $R^{19}$ may be joined to form rings, W' is a single bond or a bridge having from 1 to 20 carbon atoms which may be part of a cyclic or aromatic group, R' is hydrogen or $C_{1-6}$-alkyl, M+ is a cation, X$^-$ is an anion, x is from 1 to 240, where one or more of the radicals $R^{11}$ to $R^{19}$ may bear an additional trivalent phosphorus or nitrogen group capable of coordination, and $R^{18}$ may also be —W'—CR$^{20}$=CR$^{21}$R$^{22}$, where $R^{20}$, $R^{21}$, $R^{22}$ are as defined above for $R^{11}$ to $R^{19}$.

3. A process as claimed in claim 1, wherein the compounds of the formulae I and II are selected from among compounds of the formulae

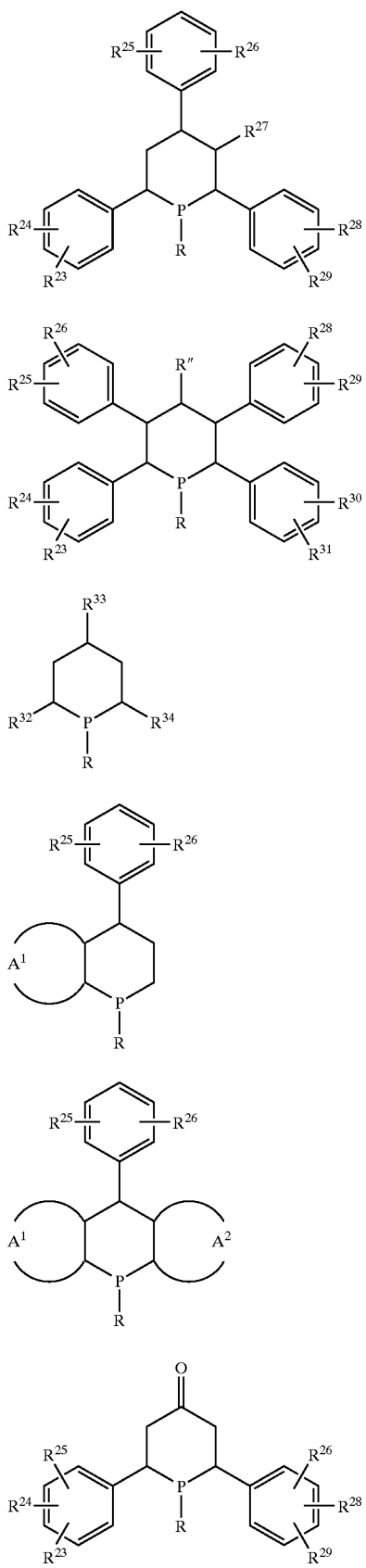

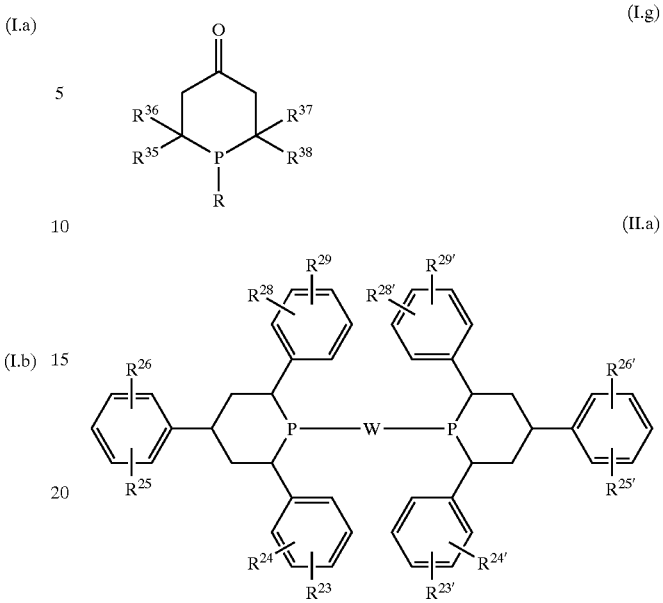

where

R is $C_{1-20}$-alkyl, cycloalkyl, $C_{6-12}$-aryl, W'(CHR'CH$_2$O)$_x$R', W'((CH$_2$)$_4$O)$_x$R' or a polymer radical having a number average molecular weight in the range from 500 to 50 000 and made up of ethylene and/or butadiene, W' is a single bond or $C_{1-4}$-alkylene, R' is hydrogen or $C_{1-20}$-alkyl, x is an integer from 1 to 240, $R^{23}$, $R^{23'}$, $R^{24}$, $R^{24'}$, $R^{25}$, $R^{25'}$, $R^{26}$, $R^{26'}$, $R^{28}$, $R^{28'}$, $R^{29}$, $R^{29'}$, $R^{30}$ and $R^{31}$ are each, independently of one another, hydrogen, alkyl, alkoxy, carboxyl, carboxylate, trifluoromethyl, -SO$_3$H, sulfonate, NE$^1$E$^2$ or alkylene -NE$^1$E$^2$, where E$^1$ and E$^2$ are each, independently of one another, hydrogen, alkyl or cycloalkyl, $R^{27}$ is hydrogen, alkyl, cycloalkyl, aryl or aralkyl, $R^{32}$, $R^{33}$, $R^{34}$, $R^{35}$, $R^{36}$, $R^{37}$ and $R^{38}$ are each, independently of one another, alkyl or cycloalkyl, R" is hydrogen or phenyl, A$^1$ and A$^2$ together with the adjacent carbon atoms of the phosphacyclohexane to which they are bound form a fused-on ring system having in each case 1 or 2 further rings, W is a bridge having from 1 to 20 carbon atoms which may be interrupted by heteroatoms.

4. A process as claimed in claim 1, wherein the radical R is a polyalkylene or polyalkylenimine radical.

5. A process as claimed in claim 1, wherein one of the radicals R or R$^1$ to R$^{10}$ in the compounds of the formula I and one of the radicals R or R$^1$ to R$^8$ or the two radicals R together or the group W in the compounds of the formula II is a polymer radical having a number average molecular weight in the range from 500 to 50 000, where the repeating units of these polymer radicals are derived from monomers selected from among monoolefins and diolefins, vinylaromatics, esters of α,β-ethylenically unsaturated monocarboxylic and dicarboxylic acids with $C_1$–$C_{30}$-alkanols, N-vinyl amides, N-vinyl lactams, heterocyclic compounds which can be polymerized with ring opening and mixtures thereof.

6. A process as claimed in claim 1, wherein one of the radicals R or $R^1$ to $R^{10}$ in the compounds of the formula I and one of the radicals R or $R^1$ to $R^8$ or the two radicals R together or a group W in the compounds of the formula II is a polyolefin radical.

7. A process as claimed in claim 1, wherein the catalyst complex and excess ligands are recirculated from the distillation bottoms of the reaction mixture, with the catalyst and excess ligand being recovered from the distillation bottoms by ultrafiltration and the retentate being recirculated.

8. A process as claimed in claim 1, wherein the work-up of the reaction mixture is carried out directly via an ultrafiltration.

9. A phosphacyclohexane of the formula I or II

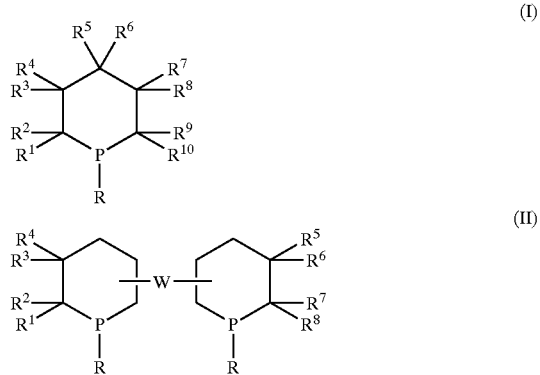

where

R is hydrogen, $C_{1-100}$-alkyl, cycloalkyl, heterocycloalkyl, $C_{7-20}$-aralkyl, $C_{7-20}$-alkaryl, $C_{6-12}$-aryl, hetaryl, W'COO$^-$W$^+$, W'SO$_3^-$M$^+$, W'PO$_3^{2-}$M$^+_2$, W'NR'$_3^+$X$^-$, W'OR', W'NR'$_2$, W'COOR', W'SR', W'(CHR'CH$_2$O)$_x$R', W'(CH$_2$NR')$_x$R', W'(CH$_2$CH$_2$NR')$_x$R', W'((CH$_2$)$_4$O)$_x$R', or W'COR', where the radicals R in the formula II may also, in place of or in addition to the group W, together form a bridge having from 1 to 20 carbon atoms which may be part of a cyclic or aromatic group and may be interrupted by heteroatoms, where the radicals R in the formula II may also, in place of or in addition to the group W, together be a polyoxyalkylene or polyalkylenimine bridge having at least 21 carbon atoms, $R^1$ to $R^{10}$ are each, independently of one another, hydrogen, $C_{1-20}$-alkyl, $C_{7-20}$-aralkyl, $C_{7-20}$-alkaryl, $C_{6-12}$-aryl, where one or more carbon atoms may be replaced by heteroatoms, W'COO$^-$M$^+$, W'SO$_3^-$M$^+$, W'PO$_3^{2-}$M$^+_2$, W'NR'$_3^+$X$^-$, W'OR', W'NR'$_2$, W'COOR', W'SR', W'(CHR'CH$_2$O)$_x$R', W'(CH$_2$NR')$_x$R', W'(CH$_2$CH$_2$NR')$_x$R', W'((CH$_2$)$_4$O)$_x$R', W'halogen, W'NO$_2$, W'COR' or W'CN, where at least three of the radicals $R^1$ to $R^{10}$ are different from hydrogen, where at least two of the radicals R and $R^1$ to $R^{10}$ comprise cyclic structures, and where one or more hydrogen atoms in the radicals R and $R^1$ to $R^{10}$ may be replaced by fluorine, W and W' are, independently of one another, single bonds or bridges having from 1 to 20 carbon atoms which may be part of a cyclic or aromatic group and may be interrupted by heteroatoms, where W may also be a polyoxyalkylene or polyalkylenimine bridge having at least 21 carbon atoms, R' is hydrogen, $C_{1-20}$-alkyl, carbonylalkyl, cycloalkyl or aryl, M+ is a cation equivalent, X$^-$ is an anion equivalent, x is from 1 to 240, where two geminal radicals $R^1$ to $R^{10}$ may form an oxo group and one or more of the radicals R and $R^1$ to $R^{10}$ may bear an additional trivalent phosphorus or nitrogen group capable of coordination, where in each case two vicinal radicals may be joined to form fused aliphatic or aromatic rings, where two vicinal radicals $R^1$ to $R^{10}$ may also be a chemical bond, where two or more bridges W may be present in the compounds of the formula II and the atoms of the phosphacyclohexane rings which are not bound to the bridge(s) W may also bear substituents defined as for $R^1$ to $R^{10}$, where one of the radicals R or $R^1$ to $R^{10}$ in the compounds of the formula I and one of the radicals R or $R^1$ to $R^8$ or both radicals R together or a group W in the compounds of the formula II may also be a polymer radical having a number average molecular weight in the range from 500 to 50 000 and made up of repeating units derived from monomers selected from among monoolefins and diolefins, vinylaromatics, esters of α,β-ethylenically unsaturated monocarboxylic and dicarboxylic acids with $C_1$–$C_{30}$-alkanols, N-vinyl amides, N-vinyllactams, heterocyclic compounds which can be polymerized with ring opening and mixtures thereof, with the exception of:

compounds of the formula I in which $R^1$ to $R^{10}$ are each hydrogen and R is selected from among hydrogen, ethyl, cyclohexyl and phenyl and compounds of the formula I in which $R^5$ and $R^6$ together form an oxo group or one of the radicals $R^5$ or $R^6$ is hydroxyl and the other is hydrogen.

10. A complex of a transition metal of transition group VIII of the Periodic Table of the Elements comprising a phosphacyclohexane ligand of formula I or II

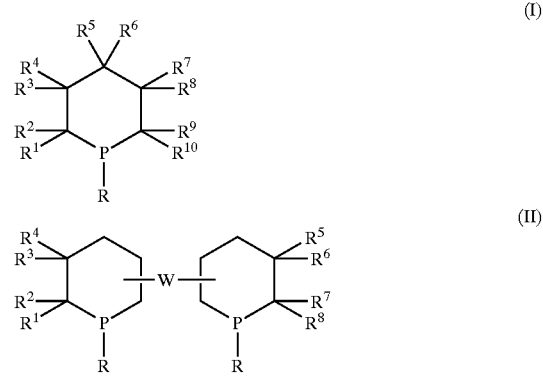

where

R is hydrogen, $C_{1-100}$-alkyl, cycloalkyl, heterocycloalkyl, $C_{7-20}$-aralkyl, $C_{7-20}$-alkaryl, $C_{6-12}$-aryl, hetaryl, W'COO$^-$M$^+$, W'SO$_3^-$M$^+$, W'PO$_3^{2-}$M$^+_2$, W'NR'$_3^+$X$^-$, W'OR', W'NR'$_2$, W'COOR', W'SR', W'(CHR'CH$_2$O)$_x$R', W'(CH$_2$NR')$_x$R', W'(CH$_2$CH$_2$NR')$_x$R', W'((CH$_2$)$_4$O)$_x$R', or W'COR', where the radicals R in the formula II may also, in place of or in addition to the group W, together form a bridge having from 1 to 20 carbon atoms which may be part of a cyclic or aromatic group and may be interrupted by heteroatoms, where the radicals R in the formula II may also, in place of or in addition to the group W, together be a polyoxyalkylene or polyalkylenimine bridge having at least 21 carbon atoms, $R^1$ to $R^{10}$ are each, independently of one another, hydrogen, $C_{1-20}$-alkyl, $C_{7-20}$-aralkyl, $C_{7-20}$-alkaryl, $C_{6-12}$-aryl, where one or more carbon atoms may be replaced by heteroatoms, W'COO$^-$M$^+$, W'SO$_3^-$M$^+$, W'PO$_3^{2-}$M$^+_2$, W'NR'$_3^+$X$^-$, W'OR', W'NR'$_2$, W'COOR', W'SR', W'(CHR'CH$_2$O)$_x$R', W'(CH$_2$NR')$_x$R', W'(CH$_2$CH$_2$HR')$_x$R', W'((CH$_2$)$_4$O)$_x$R', W'halogen, W'NO$_2$, W'COR' or W'CN, where at least two of the radicals $R^1$ to $R^{10}$ are different from hydrogen, where one or more hydrogen atoms in the radicals R and $R^1$ to $R^{10}$ may be replaced by fluorine, W and W'are, independently of one another, single bonds or bridges having from 1 to 20 carbon atoms which may be part of a cyclic or aromatic group and may be interrupted by heteroatoms, where W may also be a polyoxyalkylene or polyalkylenimine bridge having at least 21 carbon atoms, R' is hydrogen, $C_{1-20}$-alkyl, carbonylalkyl, cycloalkyl or aryl, M+ is a cation equivalent, X$^-$ is an anion equivalent, x is from 1 to 240, where two geminal radicals $R^1$ to $R^{10}$ may form an oxo group and one or more of the radicals R and $R^1$ to $R^{10}$ may bear an additional trivalent phosphorus or nitrogen group capable of coordination, where in each case two vicinal radicals may be joined to form fused aliphatic or aromatic rings, where two vicinal radicals $R^1$ to $R^{10}$ may also be a chemical bond, where two or more bridges W may be present in the compounds of the formula II and the atoms of the phosphacyclohexane rings which are not bound to the bridge(s) W may also bear substituents defined as for $R^1$ to $R^{10}$, where one of the radicals R or $R^1$ to $R^{10}$ in the compounds of the formula I and one of the radicals R or $R^1$ to $R^8$ or both radicals R together or a group W in the compounds of the formula II may also be a polymer radical having a number average molecular weight in the range from 500 to 50 000 and made up of repeating units derived from monomers selected from among monoolefins and diolefins, vinylaromatics, esters of α,β-ethylenically unsaturated monocarboxylic and dicarboxylic acids with $C_1$–$C_{30}$-alkanols, N-vinyl amides, N-vinyllactams, heterocyclic compounds which can be polymerized with ring opening and mixtures thereof.

11. The complex defined in claim 10 which is of formula X $$ML_n(CO)_m \qquad \qquad X$$

where

M is the transition metal of transition group VIII of the Periodic Table of the Elements, L is the phosphacyclohexane ligand of formula I or II, and n and m are, independently of one another, integers from 1 to 3.

12. A catalyst comprising the complex defined in claim 10.

13. A catalyst as claimed in claim 12 which further comprises at least one additional ligand selected from among halides, amines, carboxylates, acetylacetonate, arylsulfonates and alkylsulfonates, hydride, CO, olefins, dienes, cycloolefins, nitriles, N-containing heterocycles, aromatics and heteroaromatics, ethers, PF$_3$, phospholes, phosphabenzenes and monodentate, bidentate and polydentate phosphine, phosphinite, phosphonite, phosphoramidite and phosphite ligands.

14. A catalyst as claimed in claim 12, wherein the metal of transition group VIII is selected from among ruthenium, iridium, rhodium, nickel and palladium.

15. A process for preparing complexes as claimed in claim 11 by reacting a precursor complex of the metal M with the ligands L in the presence of a CO-containing gas.

16. The complex defined in claim 11 wherein M is rhodium.

17. The phosphacyclohexane defined in claim 9, which is of formula III

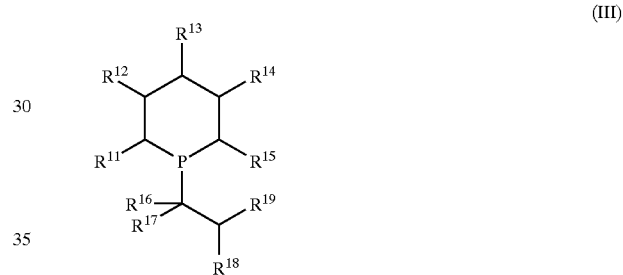

(III)

wherein $R^{11}$ to $R^{19}$ are each, independently of one another, hydrogen, $C_{1-20}$-alkyl, $C_{7-20}$-aralkyl, $C_{7-20}$-alkaryl, $C_{6-12}$-aryl, where one or more carbon atoms may be replaced by heteroatoms, W'COO$^-$M$^+$, W'SO$_3^-$M$^+$, W'PO$_3^{2-}$M$^+_2$, W'NR'$_3^+$X$^-$, W'OR', W'NR'$_2$, W'COOR', W'SR', W'(CHR'CH$_2$O)$_x$R', W'(CH$_2$NR')$_x$R', W'(CH$_2$CH$_2$NR')$_x$R', where in each case two vicinal radicals $R^{11}$ to $R^{15}$ and/or $R^{17}$ and $R^{18}$ and/or $R^{16}$ and $R^{17}$ and/or $R^{16}$ and $R^{19}$ and/or $R^{18}$ and $R^{19}$ may be joined to form rings, W' is a single bond or a bridge having from 1 to 20 carbon atoms which may be part of a cyclic or aromatic group, R' is hydrogen or $C_{1-6}$-alkyl, M$^+$ is a cation, X$^-$ is an anion, x is from 1 to 240, where one or more of the radicals $R^{11}$ to $R^{19}$ may bear an additional trivalent phosphorus or nitrogen group capable of coordination, and $R^{18}$ may also be —W'—CR$^{20}$=CR$^{21}$R$^{22}$, where R$^{20}$, R$^{21}$, R$^{22}$ are as defined above for $R^{11}$ to $R^{19}$.

* * * * *

UNITED STATES PATENT AND TRADEMARK OFFICE
CERTIFICATE OF CORRECTION

PATENT NO.         : 7,012,162 B2
APPLICATION NO. : 10/311584
DATED              : March 14, 2006
INVENTOR(S)        : Thomas Mackewitz et al.

Page 1 of 1

It is certified that error appears in the above-identified patent and that said Letters Patent is hereby corrected as shown below:

<u>Column 81,</u>
Line 60, "gem nal" should read -- geminal --.

<u>Column 82,</u>
Line 51, "abridge" should read -- a bridge --.

<u>Column 87,</u>
Line 16, "W'(CH$_2$CH$_2$HR')$_x$ R'" should read -- W'(CH$_2$CH$_2$NR')$_x$ R' --.

Signed and Sealed this

Fourth Day of July, 2006

JON W. DUDAS
*Director of the United States Patent and Trademark Office*